United States Patent
Agrawal et al.

(10) Patent No.: US 12,064,427 B2
(45) Date of Patent: Aug. 20, 2024

(54) PHARMACEUTICAL COMPOSITIONS COMPRISING (S)-4-(4-(4-(((2-(2,6-DIOXOPIPERIDIN-3-YL)-1-OXOISOINDOLIN-4-YL)OXY)METHYL) BENZYL)PIPERAZIN-1-YL)-3-FLUOROBENZONITRILE AND METHODS OF USING THE SAME

(71) Applicant: Celgene Corporation, Summit, NJ (US)

(72) Inventors: Anjali Agrawal, Basking Ridge, NJ (US); Ming J. Chen, West Windsor, NJ (US); Shyam Babu Karki, Hillsborough, NJ (US); Prajwal Gunwanth Thool, Short Hills, NJ (US); Dora Visky, Flemington, NJ (US); Ruimin Xie, Livingston, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 18/240,076

(22) Filed: Aug. 30, 2023

(65) Prior Publication Data
US 2024/0066026 A1    Feb. 29, 2024

Related U.S. Application Data

(62) Division of application No. 16/737,721, filed on Jan. 8, 2020, now Pat. No. 11,779,580.

(60) Provisional application No. 62/790,229, filed on Jan. 9, 2019.

(51) Int. Cl.
| | |
|---|---|
| A61K 31/496 | (2006.01) |
| A61K 47/02 | (2006.01) |
| A61K 47/26 | (2006.01) |
| A61K 47/36 | (2006.01) |

(52) U.S. Cl.
CPC ............ *A61K 31/496* (2013.01); *A61K 47/02* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | |
|---|---|---|
| 8,518,972 B2 | 8/2013 | Man et al. |
| 10,357,489 B2 | 7/2019 | Alexander et al. |
| 2004/0229930 A1 | 11/2004 | Gatti et al. |
| 2011/0196150 A1* | 8/2011 | Man .............. C07D 471/04 544/131 |
| 2015/0099745 A1 | 4/2015 | Parikh et al. |
| 2015/0224039 A1 | 8/2015 | Graham et al. |
| 2019/0008852 A1 | 1/2019 | Alexander et al. |
| 2020/0215060 A1 | 7/2020 | Wong |
| 2020/0216418 A1 | 7/2020 | Artman et al. |

FOREIGN PATENT DOCUMENTS

| | | |
|---|---|---|
| WO | WO 2014/191806 A2 | 12/2014 |
| WO | WO 2019/226761 A1 | 11/2019 |
| WO | WO 2019/226770 A1 | 11/2019 |

OTHER PUBLICATIONS

Ullmann, "Excipient selection for compounded pharmaceutical capsules: they're only fillers, right?," *Australian J. Pharmacy*, 98(1164):78-83 (2017).

* cited by examiner

*Primary Examiner* — Bong-Sook Baek
(74) *Attorney, Agent, or Firm* — Jones Day

(57) ABSTRACT

Provided herein are pharmaceutical compositions (e.g., oral dosage formulations) comprising (S)-4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, mixture of enantiomers, tautomer, isotopolog, or pharmaceutically acceptable salt thereof, and a carrier or diluent. Also provided herein are methods of preparing and methods of using the pharmaceutical compositions.

23 Claims, 20 Drawing Sheets

Compound 1 Crystal without Aerosil R-972

Compound 1 Crystal Coated with 2% Aerosil R-972

Compound 1 Crystal Coated with 5% Aerosil R-972

Compound 1 Crystal Coated with 5% Aerosil 300

Compound 1 Crystal Coated with 5% Aerosil 200

Control Without Aerosil

PHARMACEUTICAL COMPOSITIONS COMPRISING (S)-4-(4-(4-(((2-(2,6-DIOXOPIPERIDIN-3-YL)-1-OXOISOINDOLIN-4-YL)OXY)METHYL) BENZYL)PIPERAZIN-1-YL)-3-FLUOROBENZONITRILE AND METHODS OF USING THE SAME

This application is a divisional application of U.S. patent application Ser. No. 16/737,721, filed on Jan. 8, 2020, which claims priority to U.S. Provisional Application No. 62/790,229, filed on Jan. 9, 2019, the entirety of each of which is incorporated herein by reference.

1. FIELD

Provided herein are pharmaceutical compositions comprising (S)-4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, mixture of enantiomers, tautomer, isotopolog, or pharmaceutically acceptable salt thereof, and a carrier or diluent. Methods of use of such pharmaceutical compositions for treating, preventing, and managing various disorders are also provided herein.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. (Rawstron et al., *Blood* 2015; 125(12):1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

The variety of possible pharmaceutical compositions (e.g., oral dosage formulations comprising different excipients) creates potential diversity in physical and chemical properties for a given pharmaceutical compound. The discovery and selection of pharmaceutical compositions are of great importance in the development of an effective, stable and marketable pharmaceutical product.

3. SUMMARY

Provided herein are pharmaceutical compositions (e.g., oral dosage formulations) comprising Compound 1:

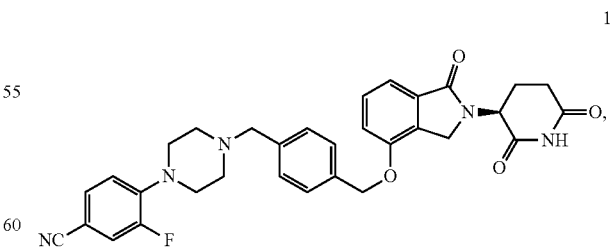

1 or an enantiomer, mixture of enantiomers, tautomer, isotopolog, or pharmaceutically acceptable salt thereof, and a carrier or diluent. Compound 1 has the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Also provided herein are methods of preparing the pharmaceutical compositions.

In one embodiment, the carrier or diluent is mannitol. In one embodiment, the carrier or diluent is a mixture of starch and lactose.

The pharmaceutical compositions provided herein are useful formulations for use in animals or humans. Thus, embodiments herein encompass the use of these pharmaceutical compositions as a final drug product. Certain embodiments provide pharmaceutical compositions useful in making final dosage forms with improved properties, e.g., powder flow properties, compaction properties, tableting properties, stability properties, and excipient compatibility properties, among others, that are needed for manufacturing, processing, formulation and/or storage of final drug products.

Also provided are pharmaceutical compositions formulated for administration by an appropriate route and means containing effective concentrations of Compound 1 provided herein. In one embodiment, the pharmaceutical compositions are oral dosage formulations. In one embodiment, the pharmaceutical compositions are immediate-release (IR) oral dosage formulations.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

In one embodiment, provided herein are methods of treating multiple myeloma comprising administering the pharmaceutical compositions provided herein. Also provided herein are combination therapies using the pharmaceutical compositions provided herein, in combination with a therapy, e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

Further provided processes for preparing the pharmaceutical compositions provided herein. In one embodiment, the process comprises coating the active ingredient with a hydrophobic silica.

These and other aspects of the subject matter described herein will become evident upon reference to the following detailed description.

4. BRIEF DESCRIPTION OF THE DRAWINGS

FIG. 1 provides a representative X-ray powder diffraction (XRPD) pattern of Form K of free base of Compound 1.

FIG. 2 provides a representative XRPD pattern of Form K' of free base of Compound 1.

FIG. 5A, FIG. 5B, FIG. 5C, and FIG. 5D shows stability profiles of different capsules with regard to degradation products at relative retention time (RRT) 4.2 minutes, 7.1 minutes, 7.6 minutes, and 11.3 minutes, respectively.

Figure 6:
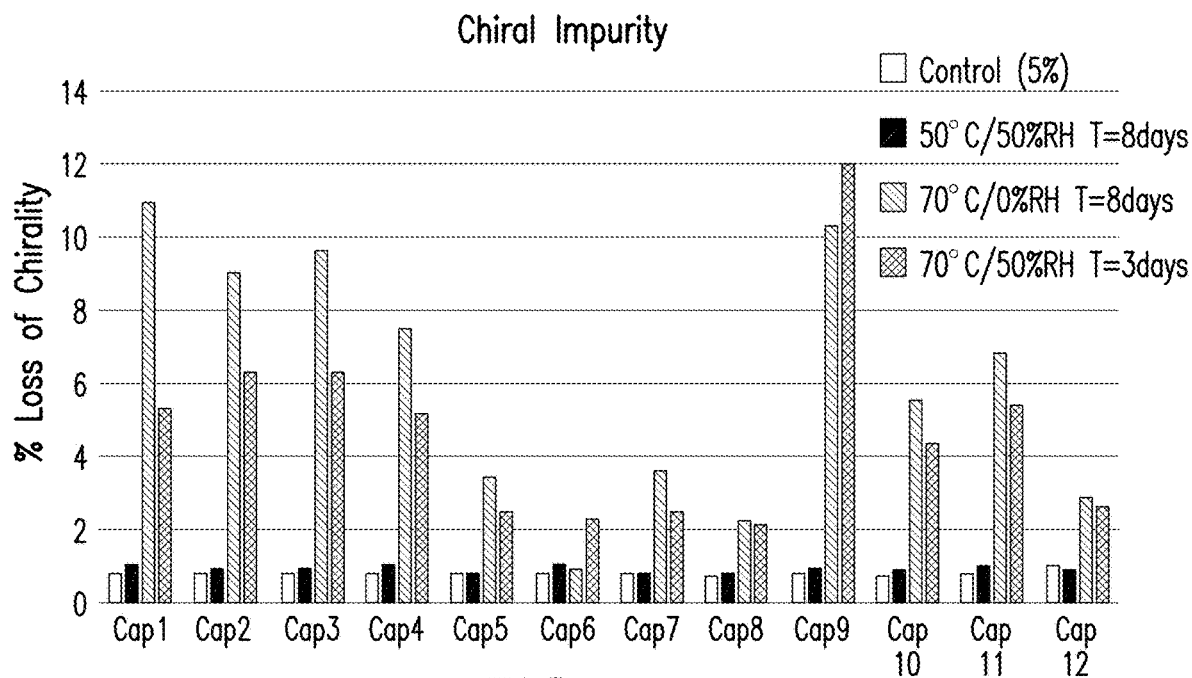

FIG. 6 shows chiral impurity profiles of different capsules.

Figure 7:
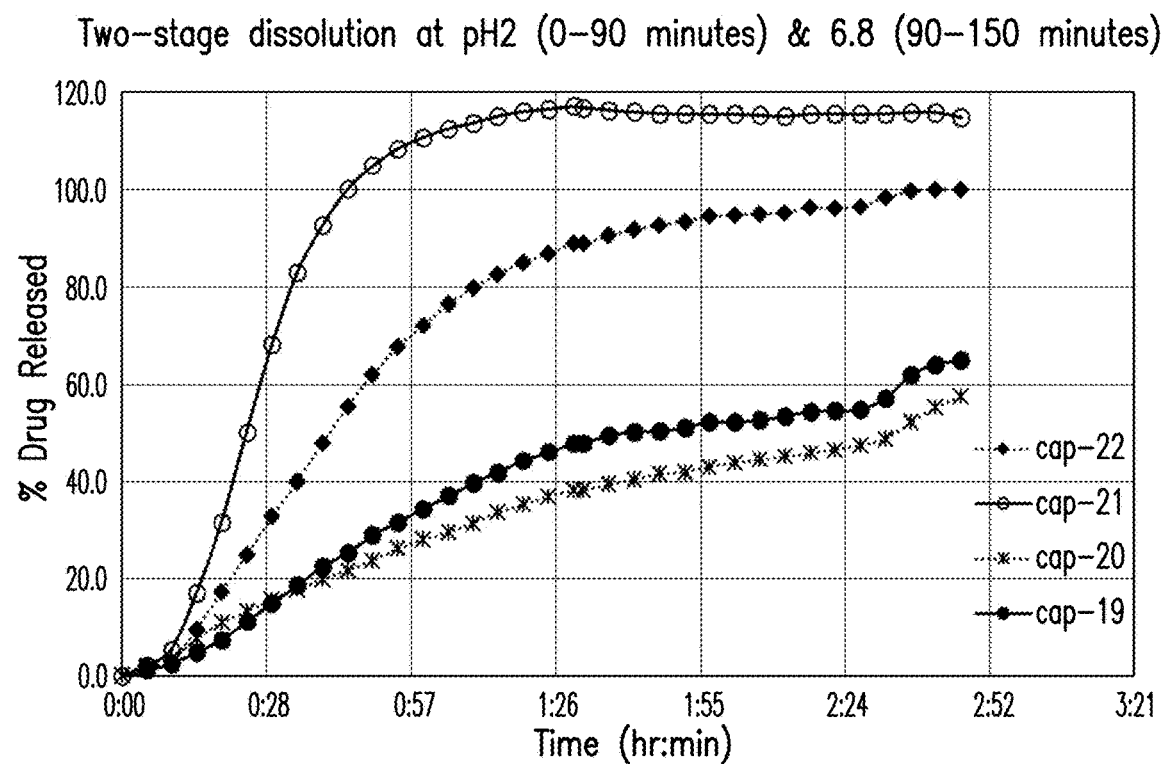

FIG. 7 shows two-stage dissolution of 2 mg formulations at pH 2 (0-90 minutes) and 6.8 (90-150 minutes).

Figure 8:
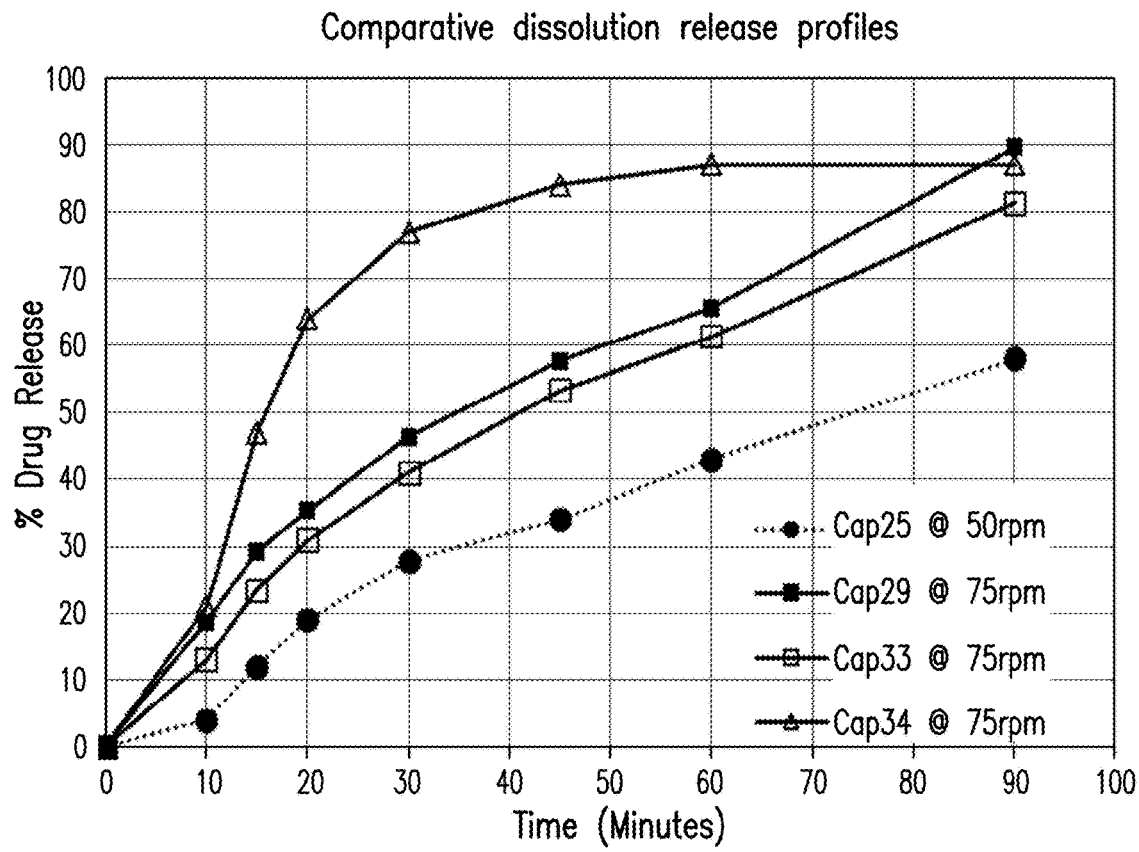

FIG. 8 shows comparative dissolution release profiles of Cap-25, Cap-29, Cap-33, and Cap-34.

Figure 9:
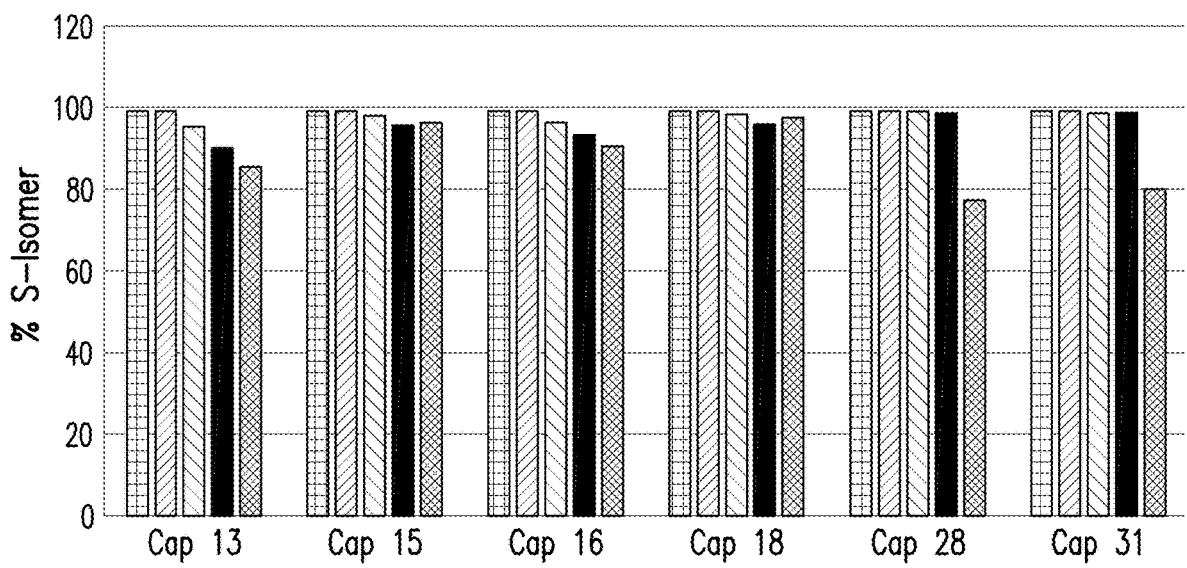

FIG. 9 shows accelerated stability assessment of mannitol and starch-lactose based blend-in-capsule (BIC) formulations.

Figure 10:
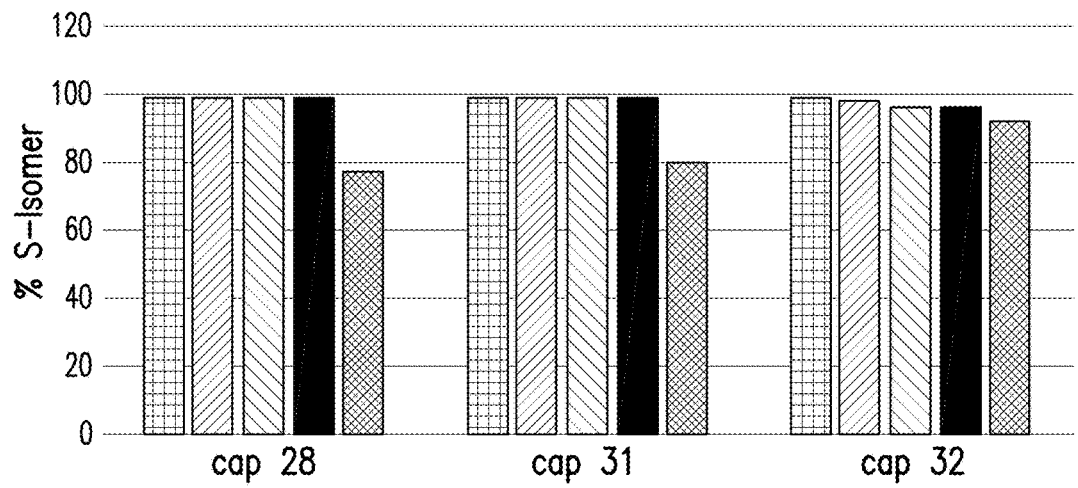

FIG. 10 shows comparative accelerated stability assessment of mannitol BIC formulations with fumaric acid and maleic acid.

Figure 11:
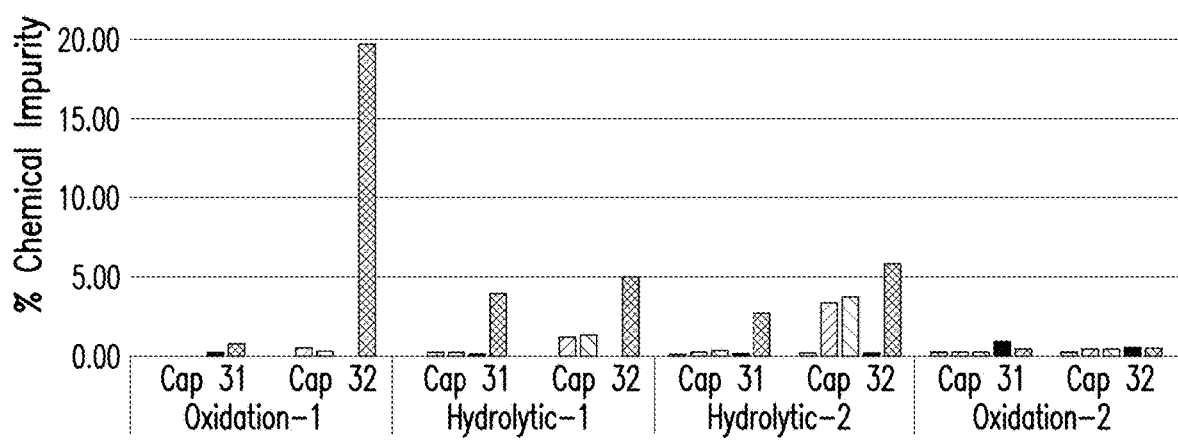

FIG. 11 shows comparative chemical degradation profiles of mannitol based BIC formulations with fumaric acid and maleic acid.

Figure 12:
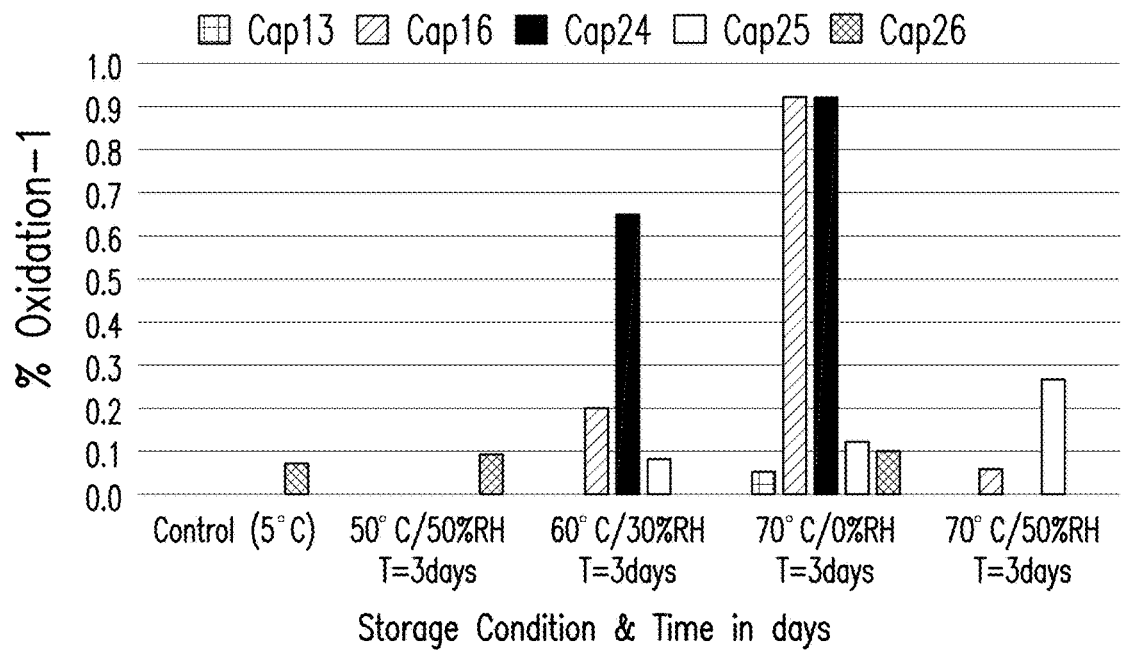

FIG. 12 shows comparative oxidative degradation (oxidation-1) profiles of starch-lactose based BIC formulations with disintegrants versus without disintegrant, and mannitol based BIC formulations.

Figure 13:
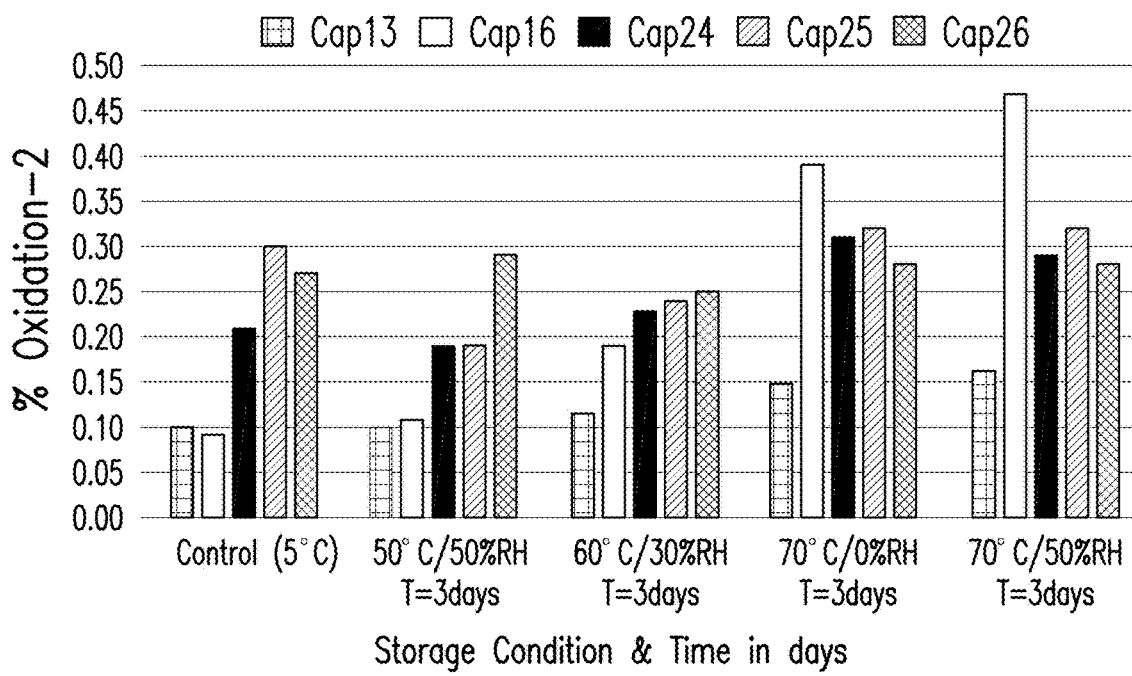

FIG. 13 shows comparative oxidative degradation (oxidation-2) profiles of starch-lactose based BIC formulations with disintegrants versus without disintegrant, and mannitol based BIC formulations.

Figure 14:
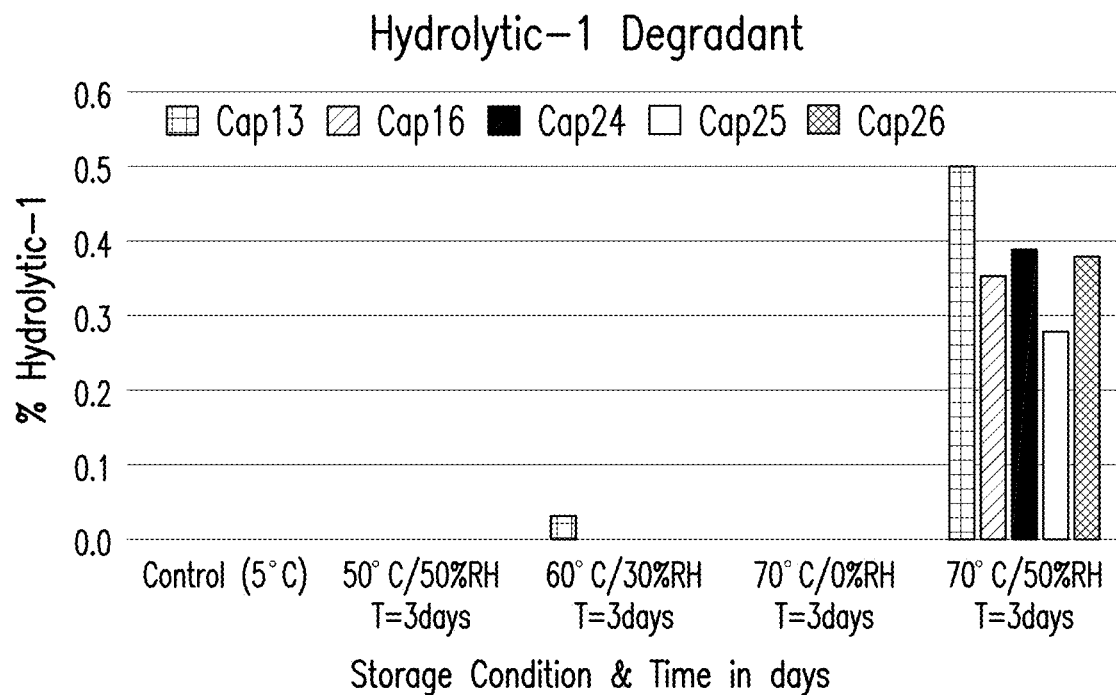

FIG. 14 shows comparative hydrolytic degradation (hydrolytic-1) profiles of starch-lactose based BIC formulations with disintegrants versus without disintegrant, and mannitol based BIC formulations.

Figure 15:
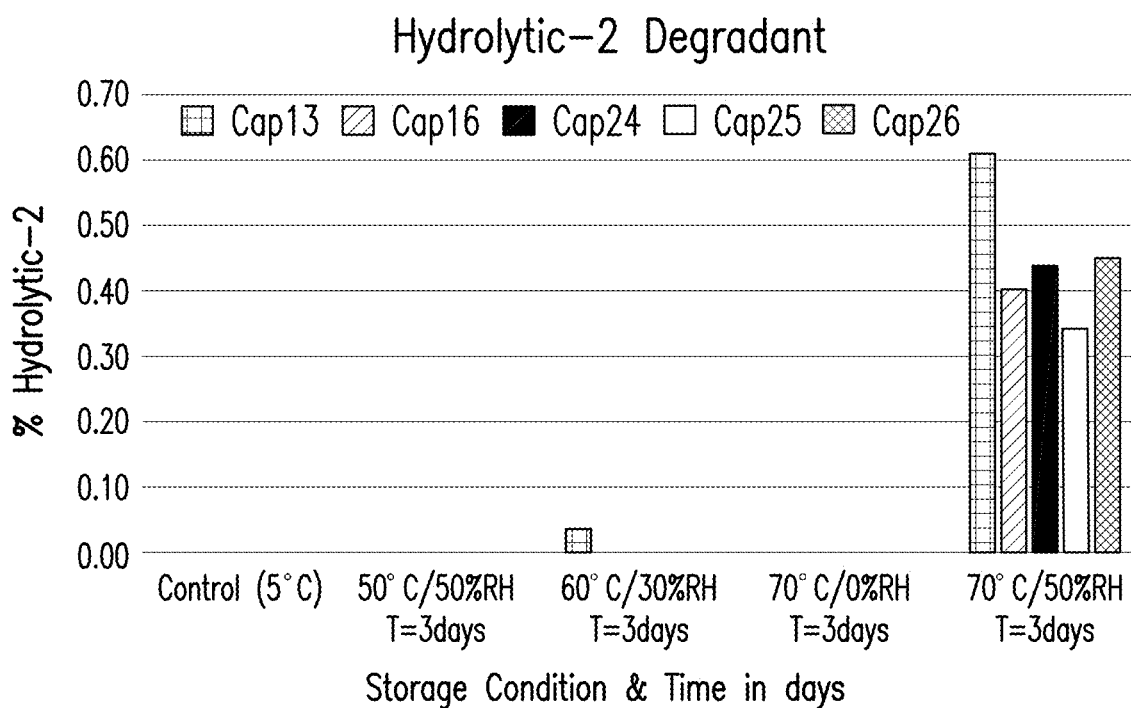

FIG. 15 shows comparative hydrolytic degradation (hydrolytic-2) profiles of starch-lactose based BIC formulations with disintegrants versus without disintegrant, and mannitol based BIC formulations.

Figure 16:
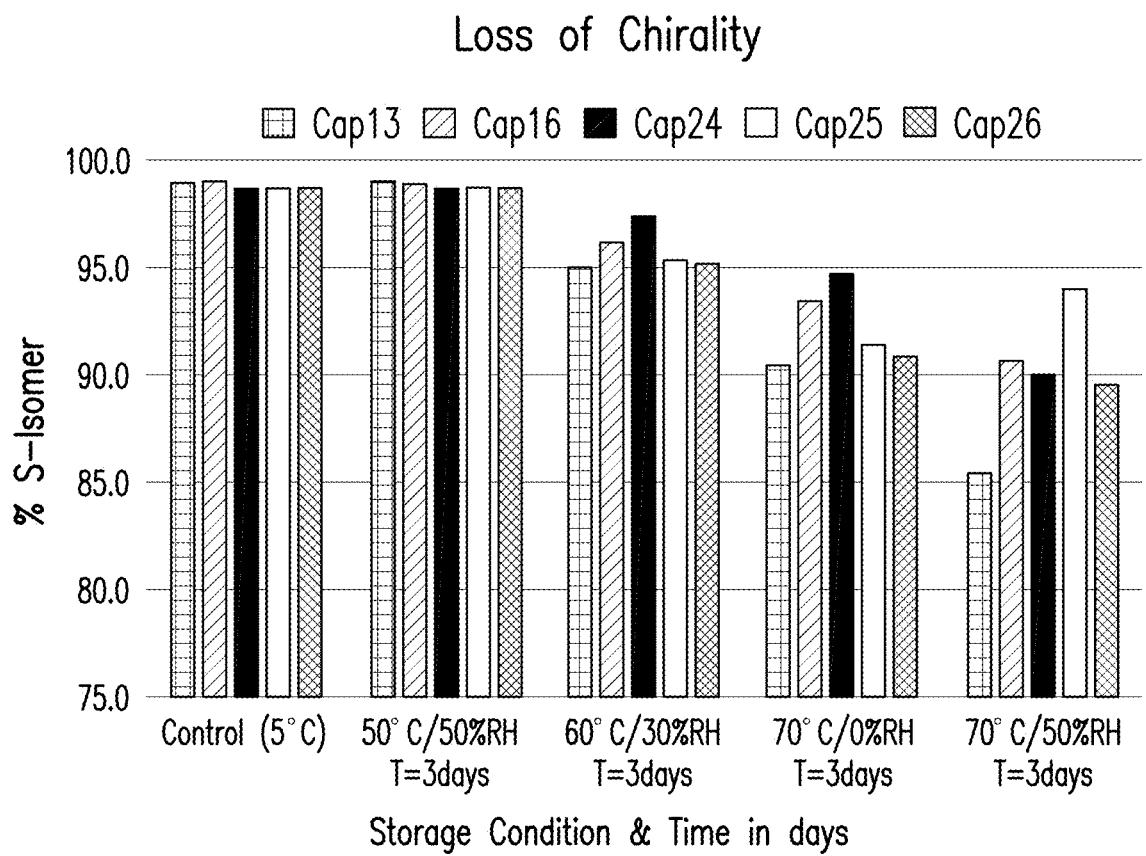

FIG. 16 shows comparative chiral impurity profiles of starch-lactose based BIC formulations with disintegrants versus without disintegrant, and mannitol based BIC formulations.

Figure 17A:
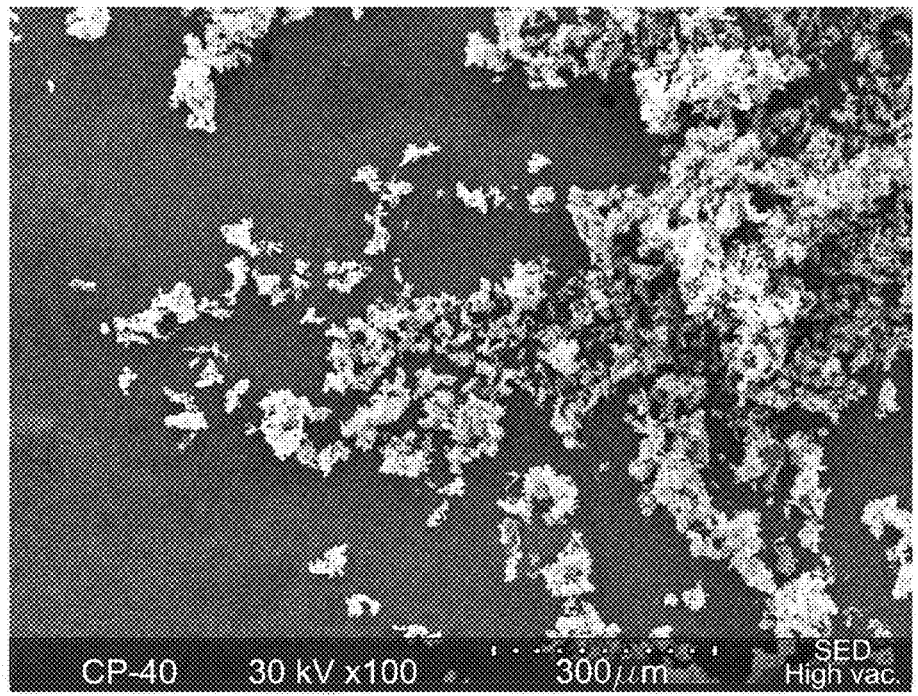
Figure 17B:
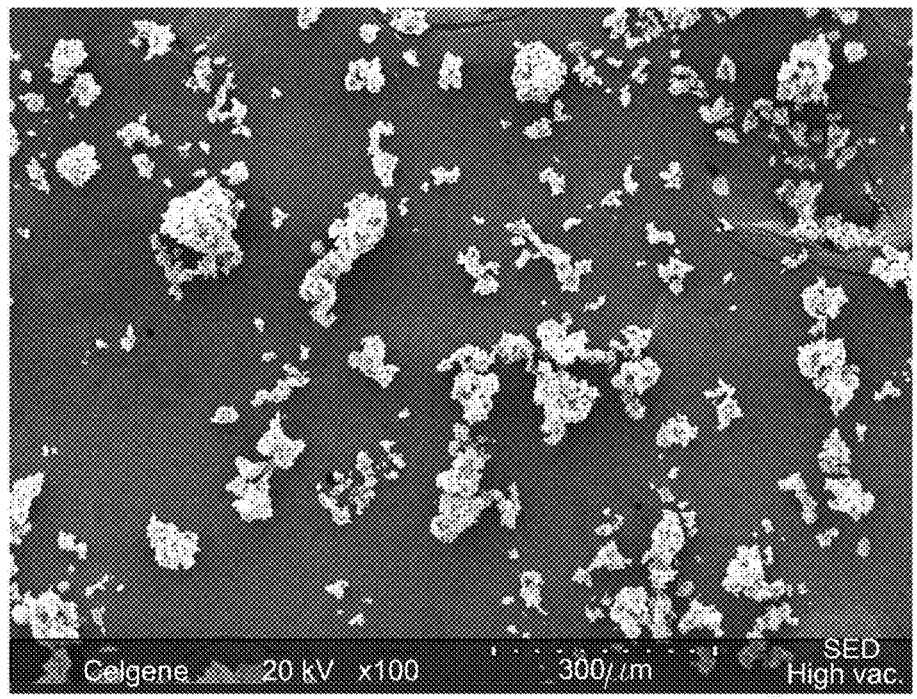
Figure 18A:
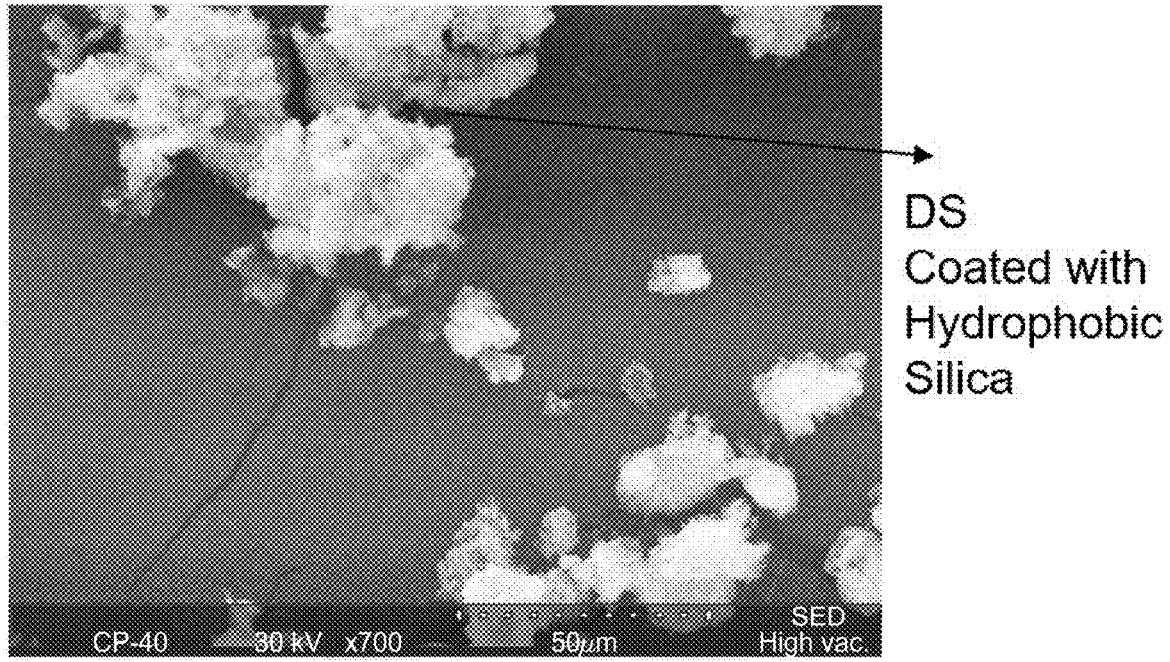
Figure 18B:
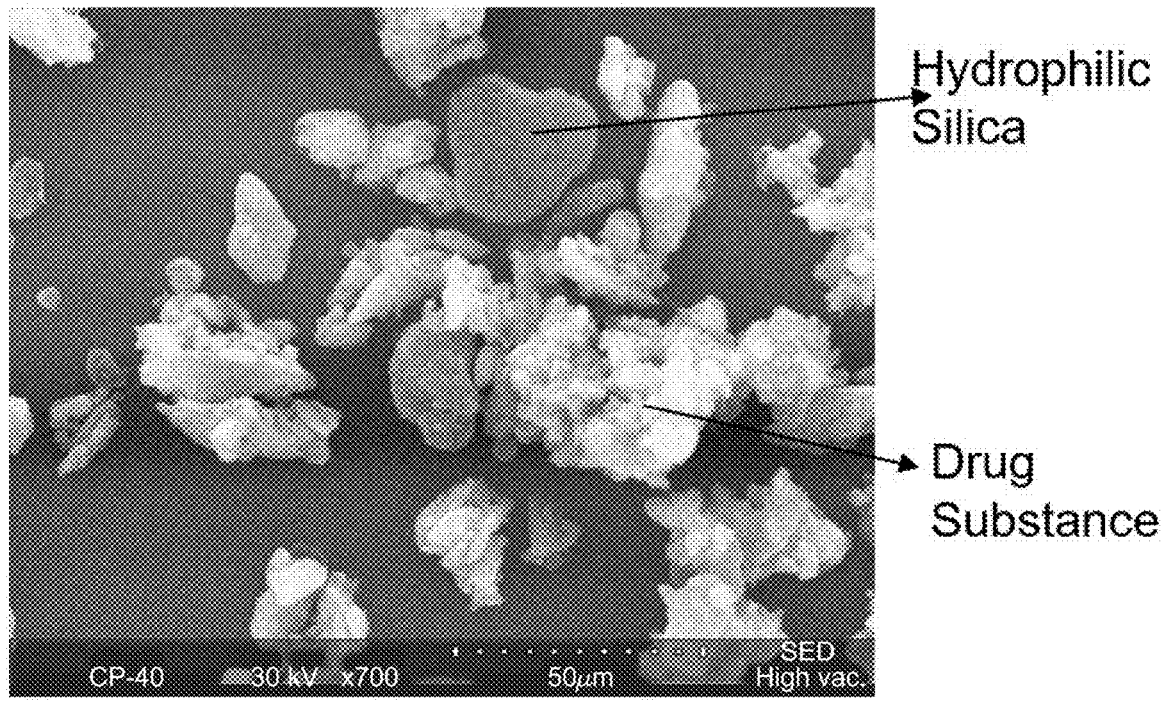
Figure 18C:
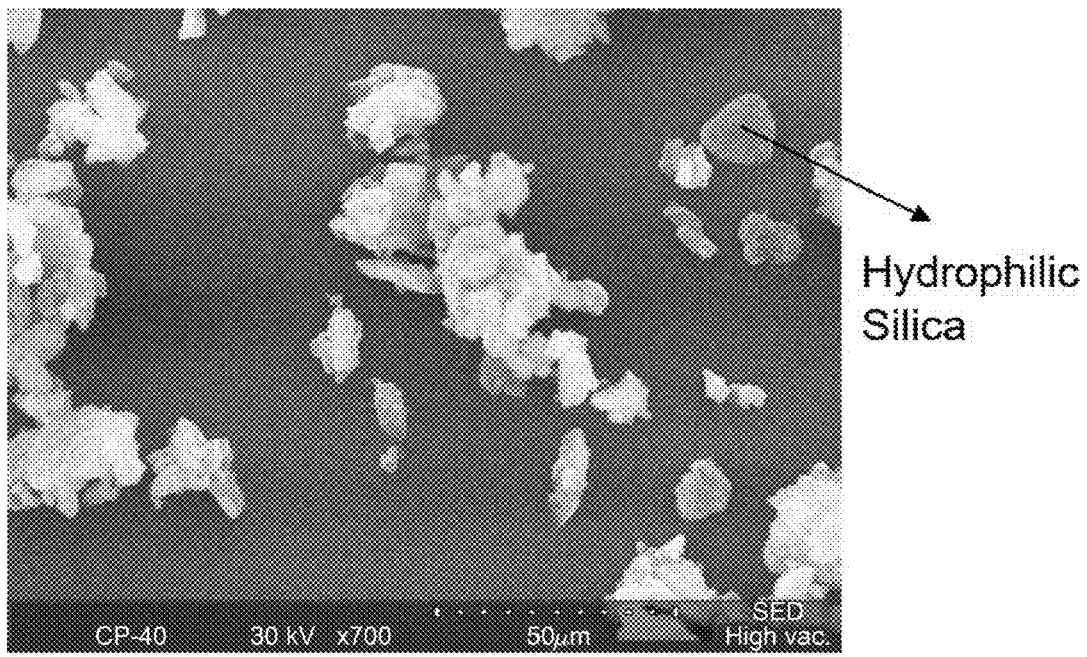
Figure 18D:
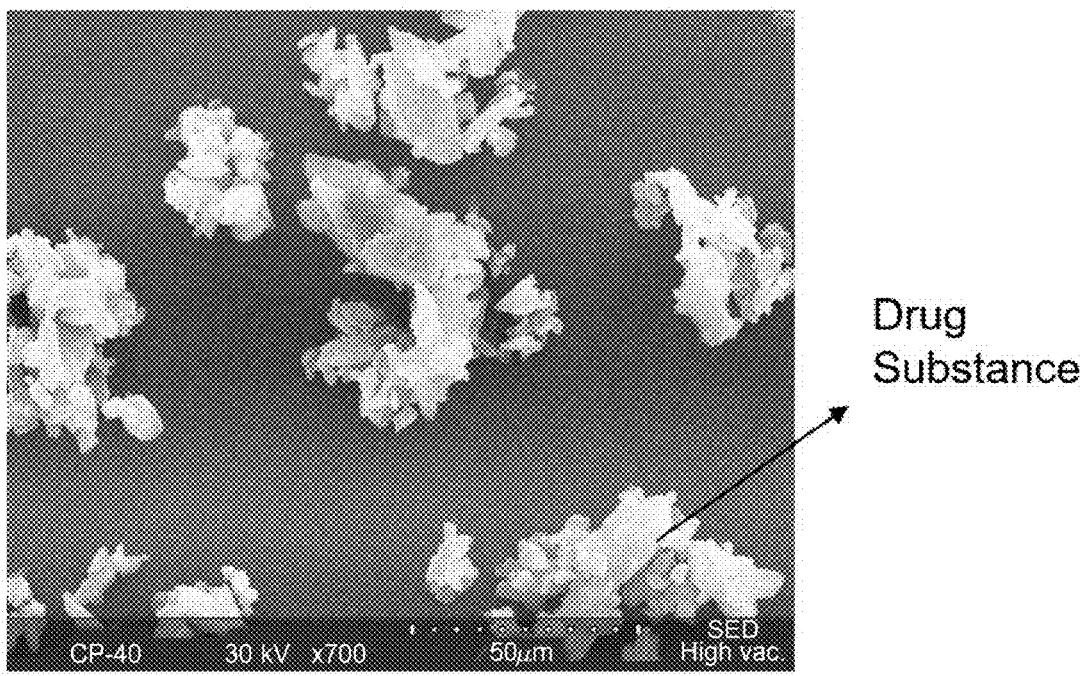

FIG. 17A and FIG. 17B provide SEM images for Compound 1 crystal not coated and coated with 2% Aerosil R-972, respectively.

FIG. 18A, FIG. 18B, FIG. 18C, and FIG. 18D provide SEM images for Compound 1 crystal coated with 5% Aerosil R-972, coated with 5% Aerosil 300, coated with 5% Aerosil 200, and not coated with silica, respectively.

Figure 19:
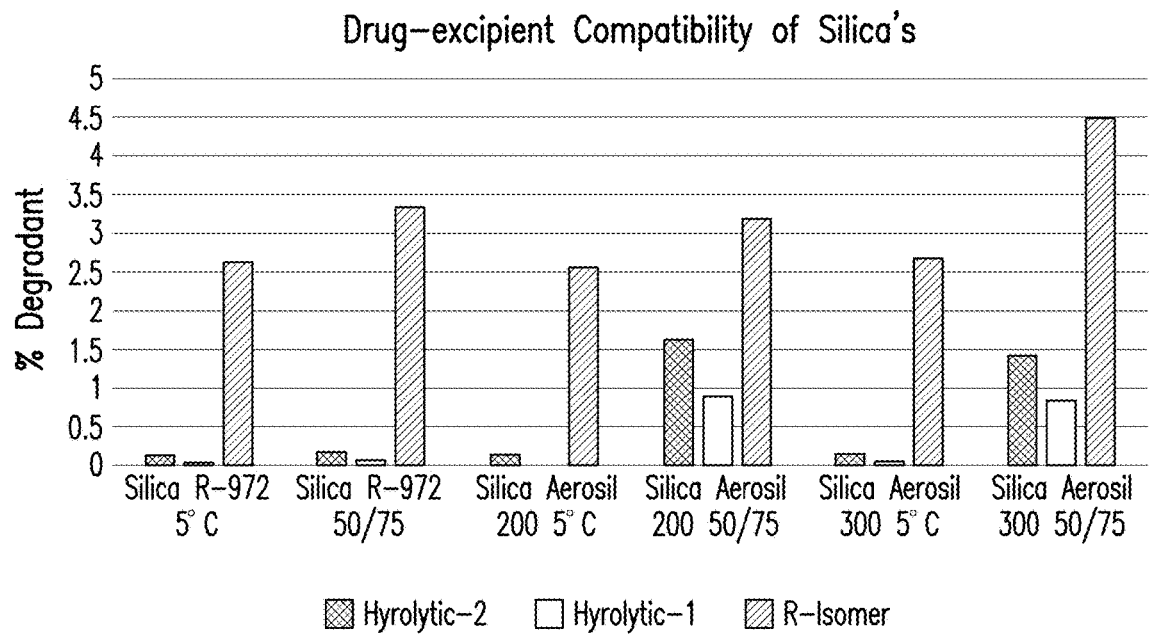

FIG. 19 shows comparative drug-excipient compatibility of different grades of silica.

Figure 20:
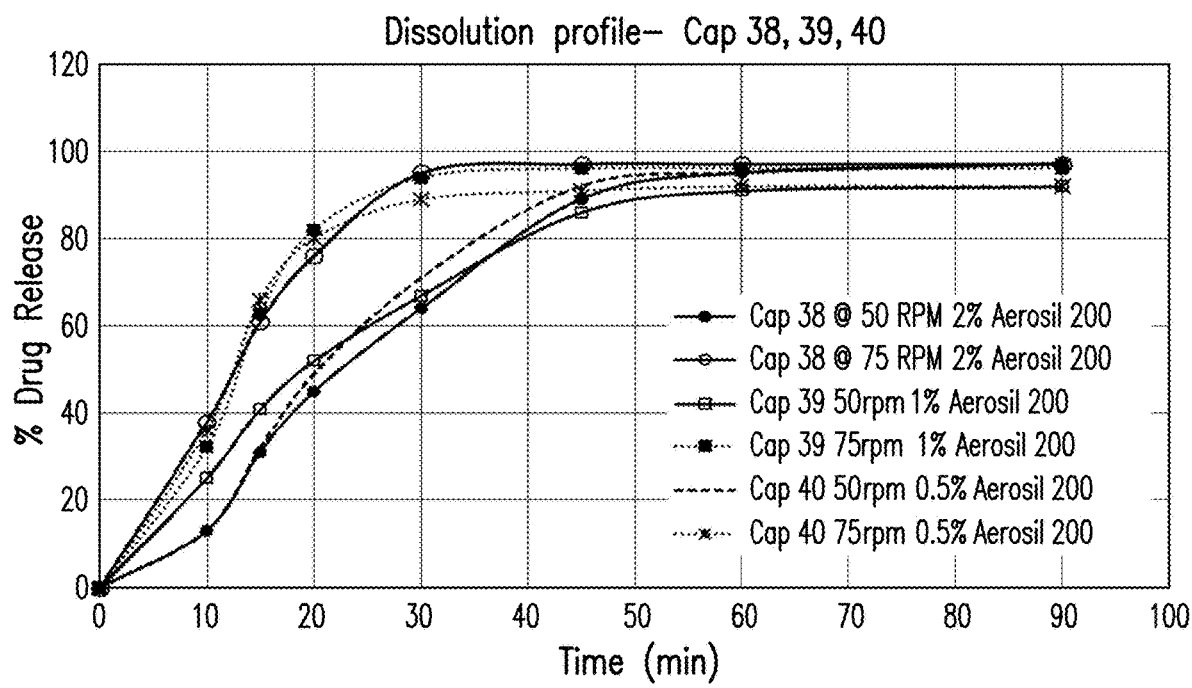

FIG. 20 shows impact of varying levels of Aerosil 200 Pharma on dissolution release profile of 2 mg starch-lactose BIC formulation.

Figure 21:
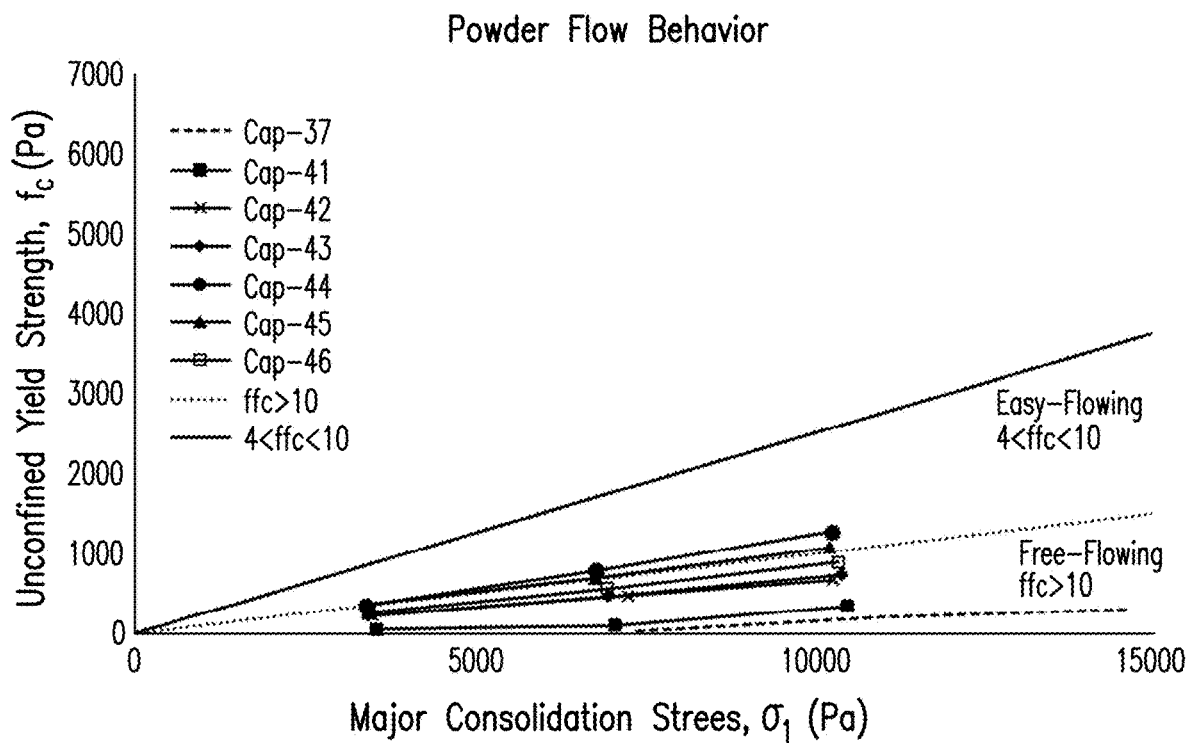

FIG. 21 shows powder flow behavior of 0.1 mg, 0.5 mg, and 2 mg mannitol and starch-lactose BIC formulations.

Figure 22:
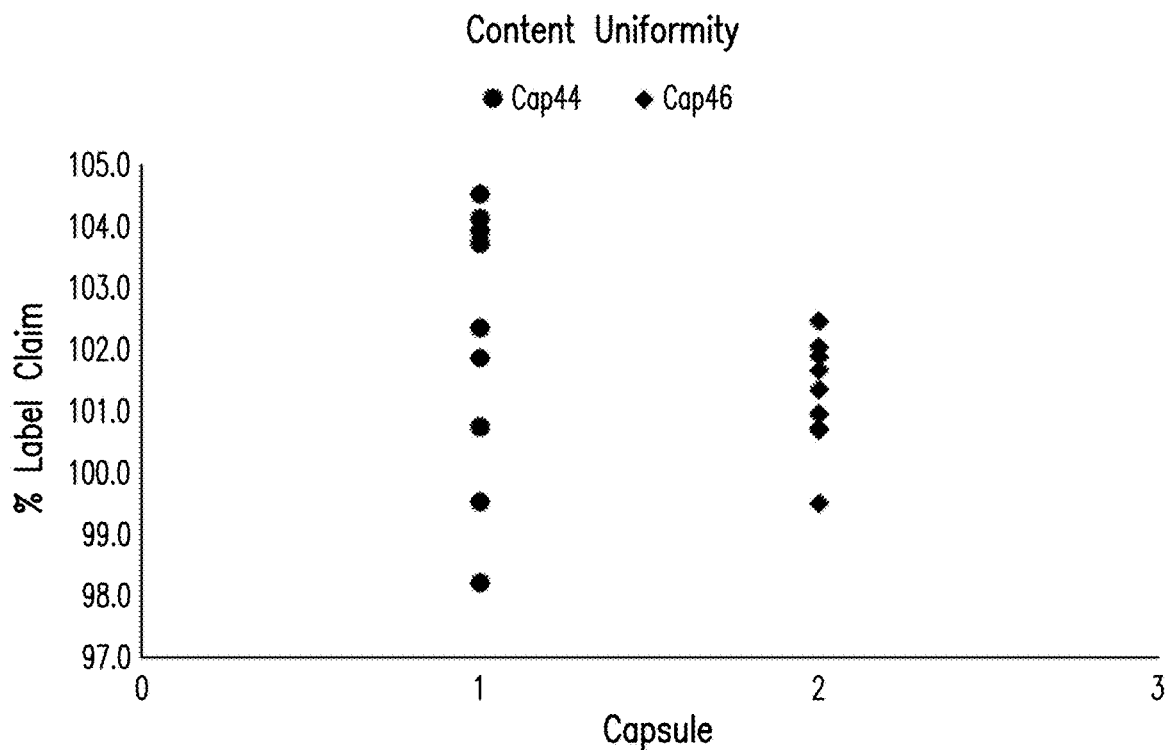

FIG. 22 shows comparative evaluation of content uniformity (CU) for 2 mg starch-lactose BIC formulations using 2% Aerosil 200 and 1% Aerosil 200.

Figure 23:
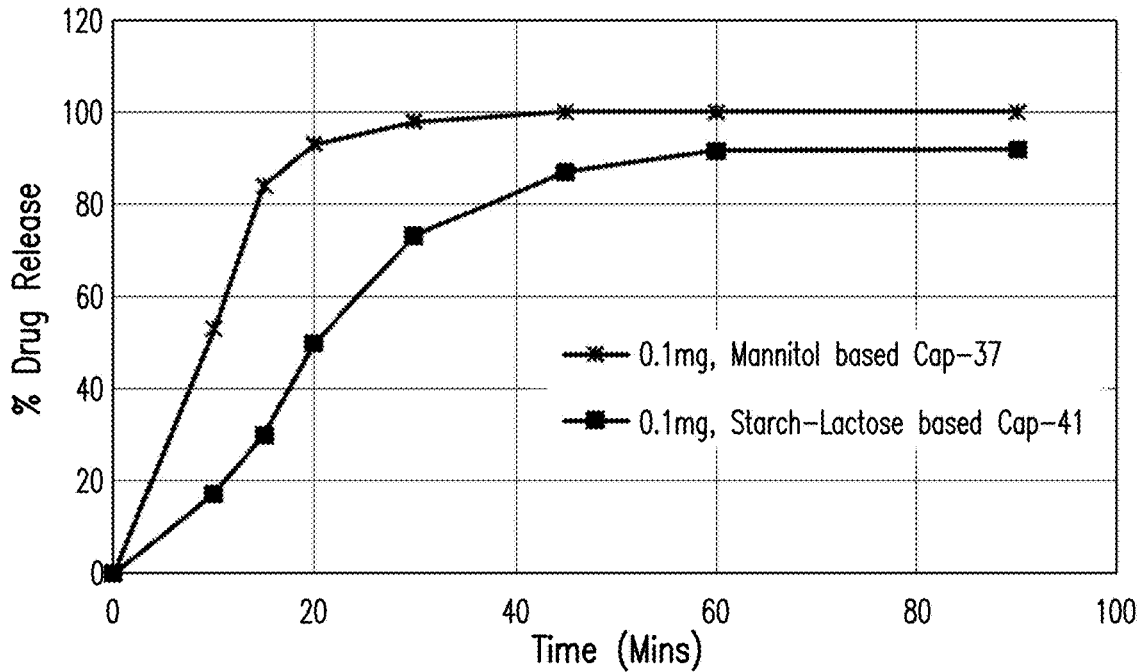

FIG. 23 shows comparative dissolution profiles of 0.1 mg mannitol BIC formulations and starch-lactose BIC formulations.

Figure 24:
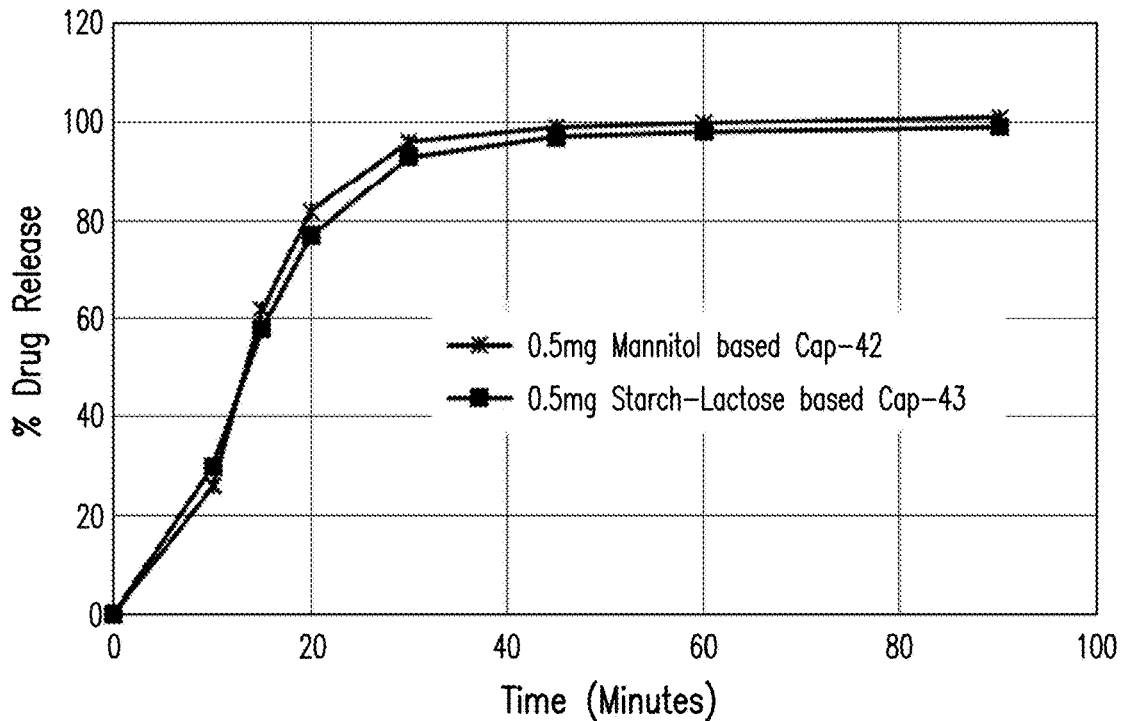

FIG. 24 shows comparative dissolution profiles of 0.5 mg mannitol BIC formulations and starch-lactose BIC formulations.

Figure 25:
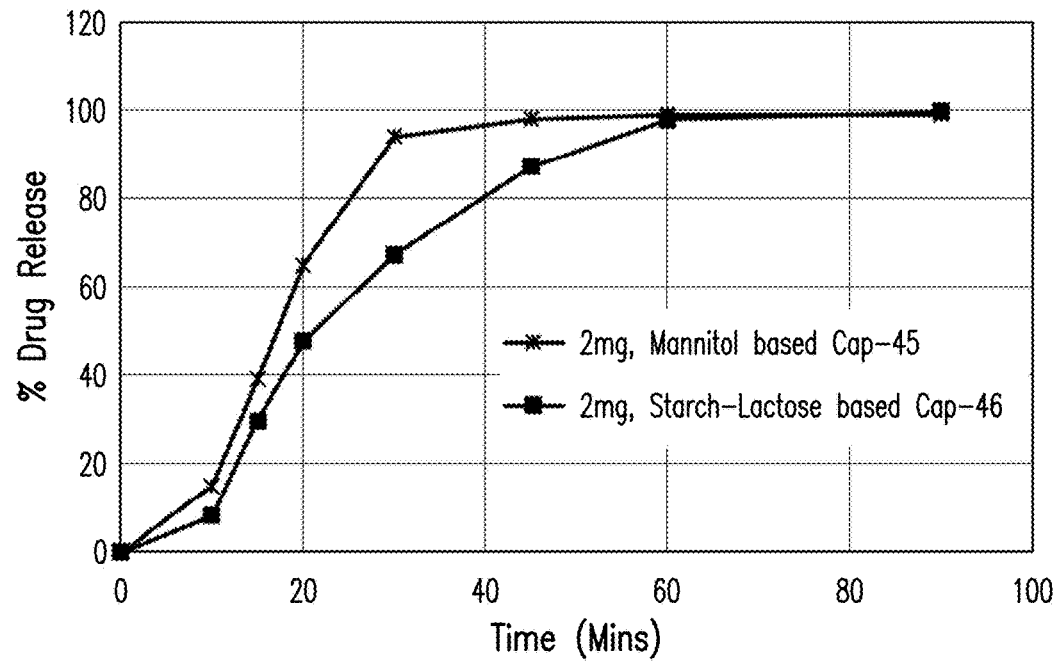

FIG. 25 shows comparative dissolution profiles of 2 mg mannitol BIC and starch-lactose BIC formulations.

Figure 26:
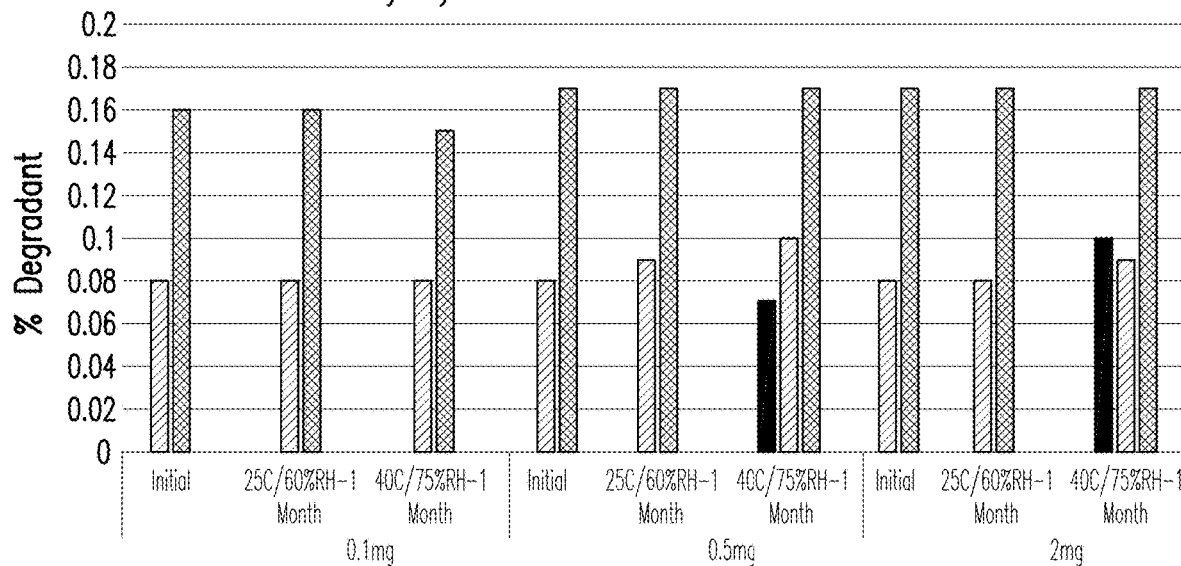

FIG. 26 shows stability data (chemical degradants) of 0.1 mg. 0.5 mg, and 2 mg mannitol BIC formulations in HDPE bottle without desiccant.

Figure 27:
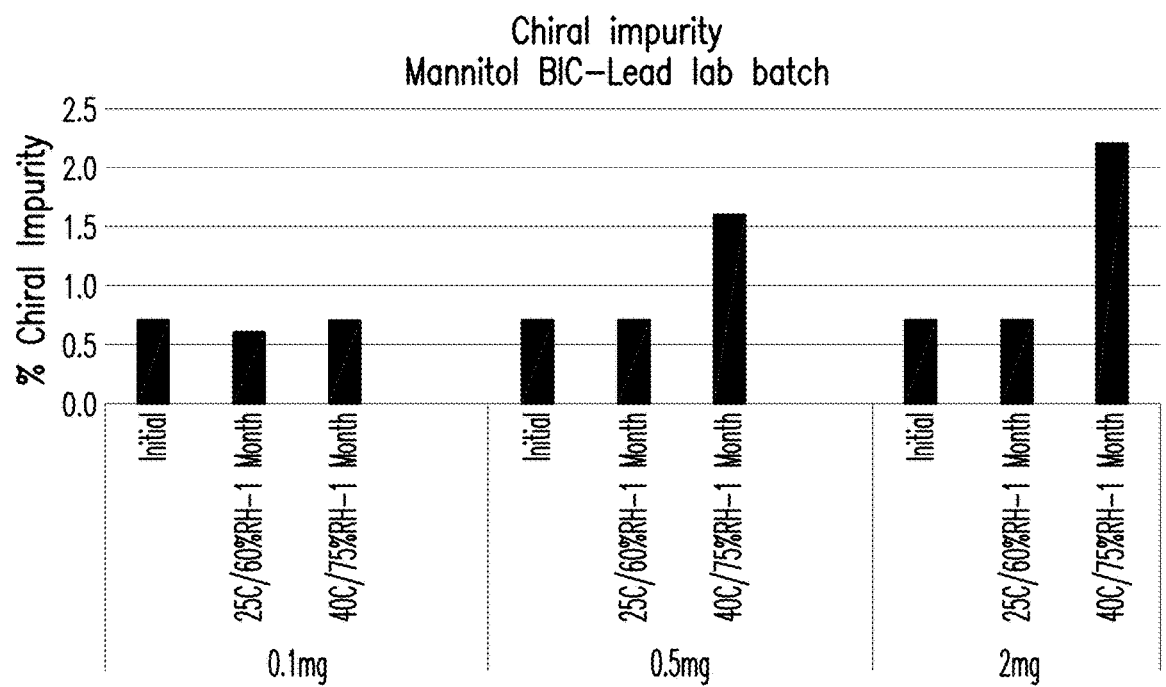

FIG. 27 shows chiral impurity profiles of 0.1 mg. 0.5 mg, and 2 mg mannitol BIC formulations.

Figure 28:
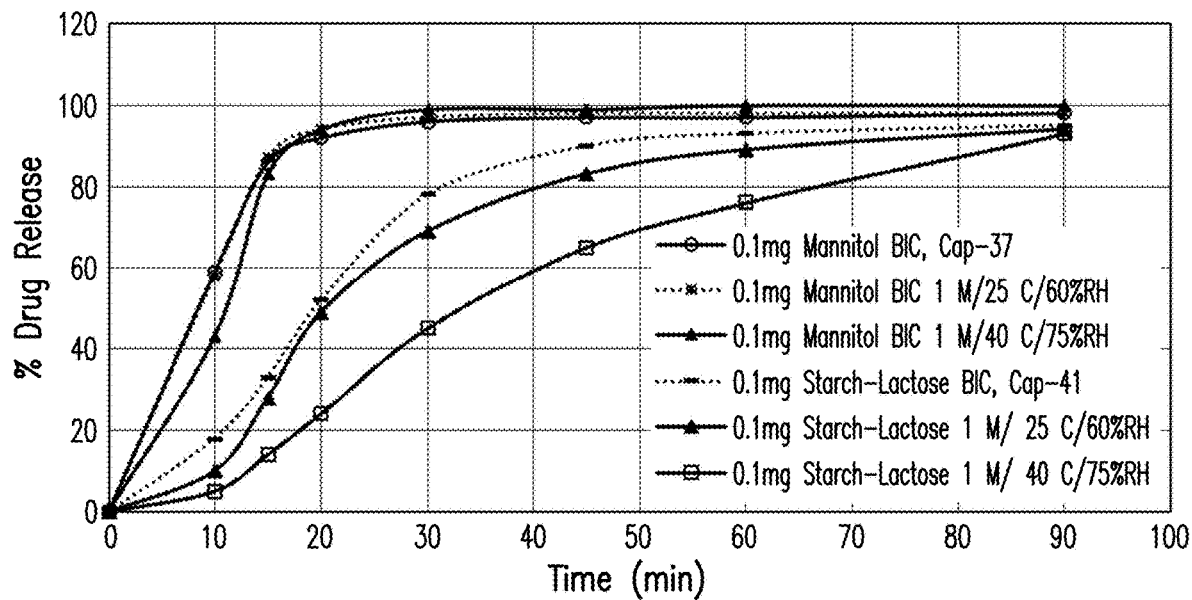

FIG. 28 shows comparative dissolution stability data of 0.1 mg mannitol BIC and starch-lactose BIC formulations.

Figure 29:
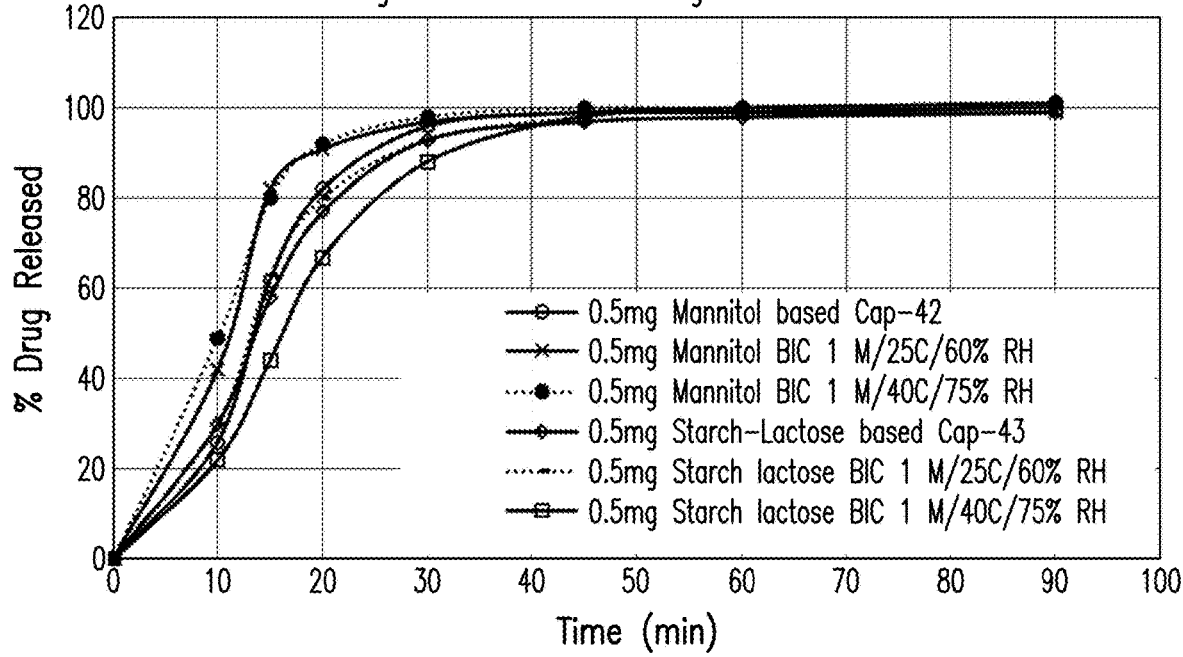

FIG. 29 shows comparative dissolution stability data of 0.5 mg mannitol BIC formulations and starch-lactose BIC formulations.

Figure 30:
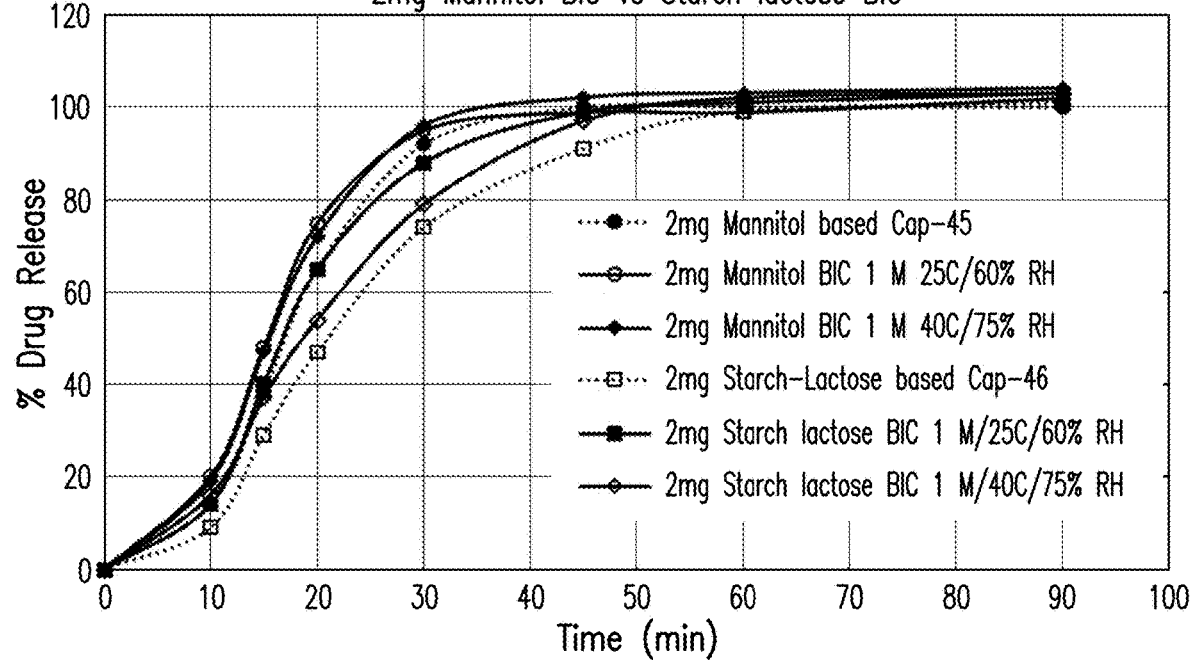

FIG. 30 shows comparative dissolution stability data of 2 mg mannitol BIC formulations and starch-lactose BIC formulations.

5. DETAILED DESCRIPTION

5.1 Definitions

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. As used herein, a tilde (i.e., "~") preceding a numerical value or range of values indicates "about" or "approximately."

Unless otherwise specified, the terms "X-ray powder diffraction", "powder X-ray diffraction", "PXRD", and "XRPD" are used interchangeably in this application.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy*, 21$^{st}$ edition, Lippincott, Williams and Wilkins, Baltimore, M D (2005); *The United States Pharmacopeia*, 23$^{rd}$ edition, 1843-1844 (1995).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, benzenesulfonic, benzoic, camphorsulfonic, carbonic, citric, dihydrogenphosphoric, ethenesulfonic, fumaric, galactunoric, gluconic, glucuronic, glutamic, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, nitric, pamoic, pantothenic, phosphoric, phthalic, propionic, suberic, succinic, sulfuric, tartaric, toluenesulfonic acid, and the like (see, e.g., S. M. Berge et al., J. Pharm. Sci., 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridine-sulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smoldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11; 14)(q13; q32); t(6; 14)(p21;32); t(12; 14)(p13; q32); or t(6;20); MMSET translocations (for example, t(4; 14)(p16; q32)); MAF translocations (for example, t(14; 16)(q32; q32); t(20;22); t(16; 22)(q11; q13); or t(14;20)(q32; q11)); or other chromosome factors (for example, deletion of 17p13, or chromosome 13; del(17/17p), nonhyperdiploidy, and gain(1 q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients, who have had a remission of multiple myeloma after therapy, have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

"Remission" as used herein, is a decrease in or disappearance of signs and symptoms of a cancer, for example, multiple myeloma. In partial remission, some, but not all, signs and symptoms of the cancer have disappeared. In complete remission, all signs and symptoms of the cancer have disappeared, although the cancer still may be in the body.

As used herein "transplant" refers to high-dose therapy with stem cell rescue. Hematopoietic (blood) or bone marrow stem cells are used not as treatment but to rescue the patient after the high-dose therapy, for example high dose chemotherapy and/or radiation. Transplant includes "autologous" stem cell transplant (ASCT), which refers to use of the patients' own stem cells being harvested and used as the replacement cells. In some embodiments, transplant also includes tandem transplant or multiple transplants.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, such as multiple myeloma, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP, as used herein, means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR), according to the IMWG Uniform Response Criteria. In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. *Leukemia*, 2006; (10) 10: 1-7), using the response and endpoint definitions shown below:

| Response Subcategory | Response Criteria[a] |
|---|---|
| SCR | CR as defined below plus |
| | Normal FLC ratio and |
| | Absence of clonal cells in bone marrow[b] by |
| | immunohistochemistry or immunofluorescence[c] |
| CR | Negative immunofixation on the serum and urine and |
| | Disappearance of any soft tissue plasmacytomas and |
| | <5% plasma cells in bone marrow[b] |
| VGPR | Serum and urine M-protein detectable by immunofixation but |
| | not on electrophoresis or 90% or greater reduction in serum |
| | M-protein plus urine M-protein level <100 mg per 24 h |
| PR | ≥50% reduction of serum M-protein and reduction in 24-h |
| | urinary M-protein by ≥90% or to <200 mg per 24 h |
| | If the serum and urine M-protein are unmeasurable,[d] a ≥50% |
| | decrease in the difference between involved and uninvolved |
| | FLC levels is required in place of the M-protein criteria |
| | If serum and urine M-protein are unmeasurable, and serum free |
| | light assay is also unmeasurable, ≥50% reduction in plasma |
| | cells is required in place of M-protein, provided baseline bone |
| | marrow plasma cell percentage was ≥30% |
| | In addition to the above listed criteria, if present at baseline, a |
| | ≥50% reduction in the size of soft tissue plasmacytomas is also |
| | required |

| Response Subcategory | Response Criteria[a] |
|---|---|
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response.

[a]All response categories require two consecutive assessments made at any time before the institution of any new therapy; all categories also require no known evidence of progressive or new bone lesions if radiographic studies were performed. Radiographic studies are not required to satisfy these response requirements.
[b]Confirmation with repeat bone marrow biopsy not needed.
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, e.g., light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

Unless otherwise specified, to the extent that there is a discrepancy between a depicted chemical structure of a compound provided herein and a chemical name of a compound provided herein, the chemical structure shall control.

5.2 Pharmaceutical Compositions Comprising Compound 1

In certain embodiment, provided herein are pharmaceutical compositions (e.g., oral dosage formulations) comprising Compound 1:

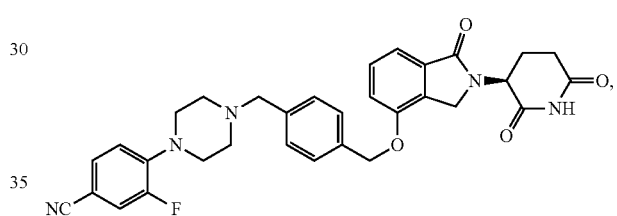

or an enantiomer, mixture of enantiomers, tautomer, isotopolog, or pharmaceutically acceptable salt thereof, and a carrier or diluent.

In some embodiments, the pharmaceutical compositions provided herein are suitable for oral administration to a patient. In one embodiment, the pharmaceutical compositions provided herein exhibit advantageous physical and/or pharmacological properties. Such properties include, but are not limited to, ease of assay, content uniformity, flow properties for manufacture, dissolution and bioavailability, and stability. In one embodiment, the pharmaceutical compositions provided herein have a shelf life of at least about 6 months, at least about 12 months, at least about 18 months, at least about 24 months, at least about 30 months, or at least about 36 months without refrigeration. In certain embodiments, "without refrigeration" refers to a temperature at or above 20° C. In one embodiment, the pharmaceutical compositions provided herein is stored under refrigerated condition. In one embodiment, the pharmaceutical compositions provided herein have a shelf life of at least about 6 months, at least about 12 months, at least about 18 months, at least about 24 months, at least about 30 months, or at least about 36 months when stored under refrigerated condition. In one embodiment, the properties of the pharmaceutical compositions provided herein make them suitable for immediate-release (IR).

Pharmaceutical compositions provided herein can be formulated into suitable pharmaceutical formulations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999). In one embodiment, the pharmaceutical compositions provided herein are oral dosage forms. In one embodiment, the oral dosage unit form is a tablet. In one embodiment, the oral dosage unit form is a caplet. In one embodiment, the oral dosage unit form is a capsule. In one embodiment, the pharmaceutical compositions provided herein are immediate-release capsules. In one embodiment, the pharmaceutical compositions provided herein are immediate-release (IR) blend in capsules (BIC).

Tablets, caplets, and capsules typically contain from about 50 mg to about 500 mg of the pharmaceutical composition (i.e., active ingredient and excipient(s)). Capsules can be of any size. Examples of standard sizes include #000, #00, #0, #1, #2, #3, #4, and #5. See, e.g., Remington's Pharmaceutical Sciences, page 1658-1659 (Alfonso Gennaro ed., Mack Publishing Company, Easton Pennsylvania, 18th ed., 1990), which is incorporated by reference. In some embodiments, capsules provided herein are of size #1 or larger, #2 or larger, #3 or larger, or #4 or larger.

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

(a) Forms of Compound 1

Compound 1 has the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Method of preparing Compound 1 has been described in U.S. application Ser. No. 16/030,695, which is incorporated herein by reference in its entirety.

In one embodiment, Compound 1, or an enantiomer, mixture of enantiomers, tautomer, isotopolog, or pharmaceutically acceptable salt thereof, is provided in the pharmaceutical composition in a solid form. In one embodiment, the solid form is amorphous. In one embodiment, the solid form is crystalline. In one embodiment, the solid form is a hydrate. In one embodiment, the solid form is an anhydrate. In one embodiment, the solid form is a solvate. In one embodiment, the solid form is non-solvated.

The solid forms may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

In one embodiment, the pharmaceutical composition comprises free base of Compound 1. In one embodiment, the free base of Compound 1 is amorphous. In one embodiment, the free base of Compound 1 is crystalline. In one embodiment, the free base of Compound 1 is a mixture of one or more of amorphous form and crystalline forms.

In one embodiment, the pharmaceutical composition comprises a salt of Compound 1. In one embodiment, the salt is a hydrochloride salt, a mesylate salt, a hydrobromide salt, a besylate salt, a glycolate salt, a L-malate salt, a napadisylate salt, a sulfate salt, a tosylate salt, an oxalate salt, an isethionate salt, a maleate salt, a phosphate salt, a malonate salt, a gentisate salt, a L-tartrate salt, a fumarate salt, a citrate salt, a R-mandelate salt, a L-ascorbate salt, a succinate salt, a nitrate salt, a salicylate salt, an edisylate salt, a cyclamate salt, an esylate salt, a D-glucuronate salt, an 4-aminosalicylate salt, a caproate salt, a cinnamate salt, a caprylate salt, a camphorate salt, a D-aspartate salt, or a D-glutamate salt. In one embodiment, the salt of Compound 1 is amorphous. In one embodiment, the salt of Compound 1 is crystalline. In one embodiment, the salt of Compound 1 is a mixture of one or more of amorphous form and crystalline forms.

In one embodiment, the pharmaceutical composition comprises a hydrochloride salt of Compound 1. In one embodiment, the pharmaceutical composition comprises a mesylate salt of Compound 1. In one embodiment, the pharmaceutical composition comprises a hydrobromide salt of Compound 1. In one embodiment, the pharmaceutical composition comprises a besylate salt of Compound 1. In one embodiment, the pharmaceutical composition comprises a glycolate salt of Compound 1. In one embodiment, the pharmaceutical composition comprises a L-malate salt of Compound 1.

In one embodiment, the pharmaceutical composition comprises Form K of free base of Compound 1, Form K' of free base of Compound 1, or an intermediate form between Form K and Form K', or a mixture thereof.

In one embodiment, Form K is a channel hydrate of free base of Compound 1. In one embodiment, Form K is a monohydrate of free base of Compound 1. In one embodiment, Form K' is a dehydrated hydrate of Form K. In one embodiment, without being limited by a particular theory, Form K' converts to Form K with increasing humidity, and Form K converts to Form K' with decreasing humidity. Accordingly, intermediate forms between Form K and Form K' exist depending on the degree of humidity. In one embodiment, From K converts to Form K' when water activity is not higher than about 0.11. In one embodiment, From K' converts to Form K when water activity is not lower than about 0.17.

In one embodiment, the pharmaceutical composition provided herein comprises Form K, Form K', or an intermediate form between Form K and Form K', or a mixture thereof, of free base of Compound 1, characterized by an XRPD pattern comprising peaks at approximately 14.6, 18.2, and 18.3° 2θ. In one embodiment, the XRPD pattern further comprises peaks at approximately 22.3 and 23.1° θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.5, 20.9, 22.3, and 23.1° 2θ. In one embodiment, the pharmaceutical composition provided herein comprises Form K of free base of Compound 1, characterized by an XRPD pattern further comprising at least a peak at approximately 14.2, 18.6, or 20.3° 2θ. In one embodiment, the pharmaceutical composition provided herein comprises Form K' of free base of Compound 1, characterized by an XRPD pattern further comprising at least a peak at approximately 18.0 or 18.8° 2θ.

Figure 1:
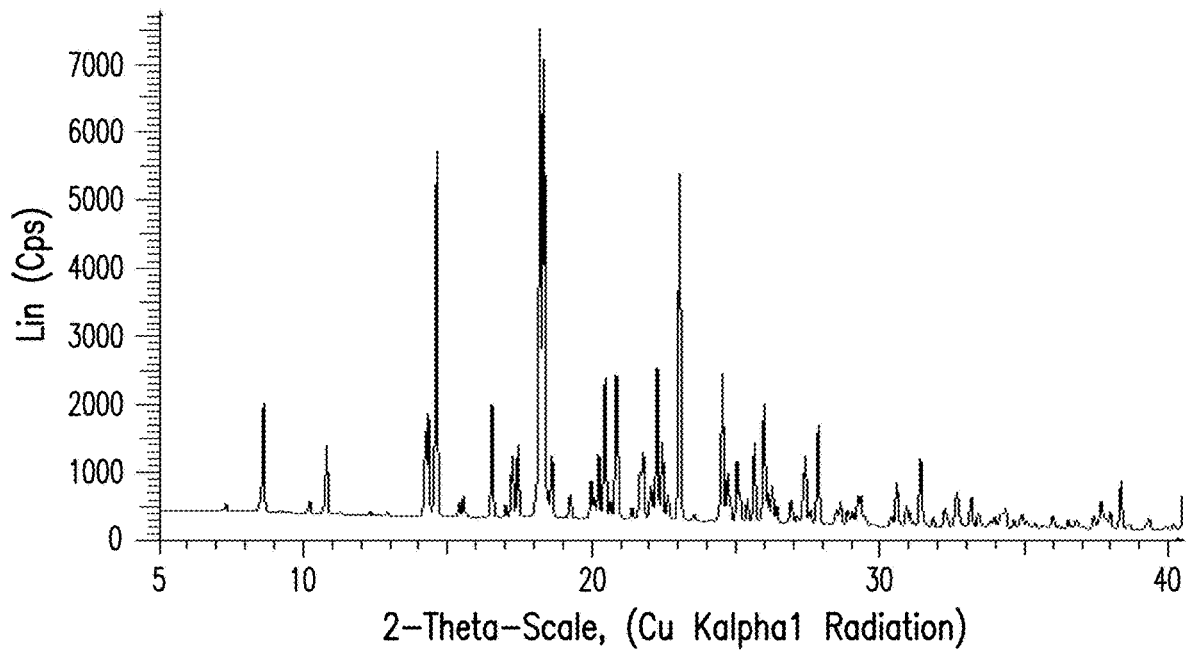

A representative XRPD pattern of Form K is provided in FIG. 1.

In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.6, 10.8, 14.2, 14.3, 14.6, 16.6, 17.3, 17.5, 18.2, 18.3, 18.6, 20.3, 20.5, 20.9, 21.8, 22.3, 22.5, 23.1, 24.5, 25.1, 25.7, 26.0, 27.4, 27.9, and 31.4° 2θ. In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.59, 10.78, 14.21, 14.32, 14.60, 16.55, 17.26, 17.45, 18.21, 18.34, 18.62, 20.25, 20.47, 20.87, 21.79, 22.28, 22.45, 23.05, 24.54, 25.05, 25.67, 26.01, 27.43, 27.89, and 31.44° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises free base of Compound 1, which is a solid form characterized by an XRPD pattern comprising peaks at approximately 14.2, 14.6, 18.2, and 18.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.04° 2θ. In one embodiment, the XRPD pattern does not contain a peak at 18.0° 2θ 0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.21, 14.60, 18.21, and 18.34° 2θ+0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ±0.02° 2θ. In one embodiment, the XRPD pattern further comprises peaks at 22.3, 23.1, and 24.5° 2θ0.02° 2θ. In one embodiment, the XRPD pattern further comprises peaks at 20.5 and 20.9° 2θ±0.02° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.02° 2θ. In one embodiment, the XRPD pattern does not contain a peak at 18.0° 2θ0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.21, 14.60, 18.21, and 18.34° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.02° 2θ.

In one embodiment, the pharmaceutical composition provided herein comprises free base of Compound 1, which is a solid form characterized by an XRPD pattern comprising peaks at 14.2, 14.6, 18.2, and 18.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.21, 14.60, 18.21, and 18.34° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern comprising peaks at approximately 14.6, 18.2, 18.3, and 18.6° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.6, 18.2, 18.3, and 18.6° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.60, 18.21, 18.34, and 18.62° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.6, 18.2, 18.3, and 18.6° 2θ±0.02° 2θ. In one embodiment, the XRPD pattern further comprises peaks at 22.3, 23.1, and 24.5° 2θ0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.60, 18.21, 18.34, and 18.62° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.020 2θ.

In one embodiment, the pharmaceutical composition provided herein comprises free base of Compound 1, which is a solid form characterized by an XRPD pattern comprising peaks at 14.6, 18.2, 18.3, and 18.6° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.60, 18.21, 18.34, and 18.62° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern comprising peaks at approximately 14.6, 18.2, 18.3, and 20.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, the pharmaceutical composition provided herein comprises free base of Compound 1, which is a solid form characterized by an XRPD pattern comprising peaks at 14.60, 18.21, 18.34, and 20.25° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ±0.02° 2θ. In one embodiment, the XRPD pattern further comprises peaks at 22.3, 23.1, and 24.5° 2θ0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, the pharmaceutical composition provided herein comprises free base of Compound 1, which is a solid form characterized by an XRPD pattern comprising peaks at 14.60, 18.21, 18.34, and 20.25° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.02° 2θ.

In one embodiment, the pharmaceutical composition provided herein comprises free base of Compound 1, which is a solid form characterized by an XRPD pattern comprising peaks at 14.6, 18.2, 18.3, and 20.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, the pharmaceutical composition provided herein comprises free base of Compound 1, which is a solid form characterized by an XRPD pattern comprising peaks at 14.60, 18.21, 18.34, and 20.25° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, the pharmaceutical composition provided herein comprises free base of Compound 1, which is a solid form characterized by an XRPD pattern that matches the XRPD pattern presented in FIG. 1.

Figure 2:
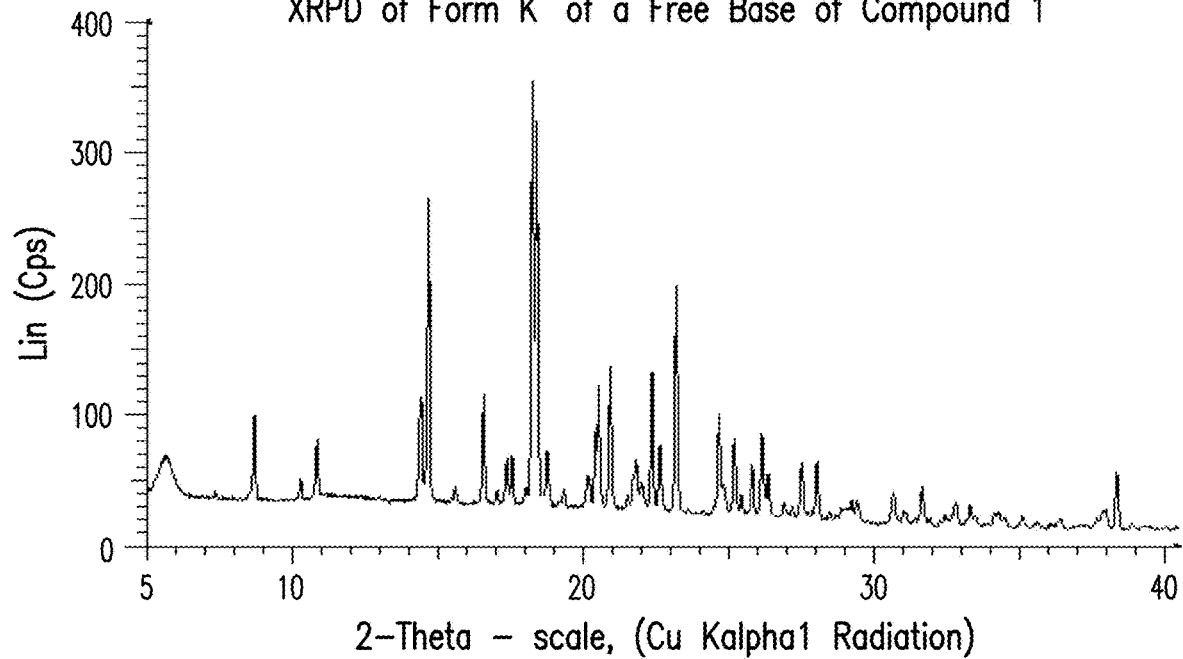

A representative XRPD pattern of Form K' is provided in FIG. 2.

In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.7, 10.8, 14.4, 14.6, 16.6, 17.4, 17.5, 18.0, 18.3, 18.4, 18.8, 20.5, 20.9, 21.8, 22.4, 22.6, 23.2, 24.7, 25.2, 25.8, 26.2, 26.4, 27.5, 28.1, 31.7, and 38.4° 2θ. In one embodiment, the pharmaceutical composition provided herein comprises free base of Compound 1, which is a solid form characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.65, 10.79, 14.36, 14.63, 16.55, 17.35, 17.53, 18.02, 18.25, 18.40, 18.75, 20.52, 20.92, 21.81, 22.36, 22.64, 23.19, 24.68, 25.20, 25.82, 26.17, 26.39, 27.54, 28.08, 31.69, and 38.41° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, the pharmaceutical composition provided herein comprises free base of Compound 1, which is a solid form characterized by an XRPD pattern comprising peaks at approximately 14.6, 18.0, 18.3, and 18.4° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.0, 18.3, 18.4, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, the pharmaceutical composition provided herein comprises free base of Compound 1, which is a solid form characterized by an XRPD pattern comprising peaks at 14.63, 18.02, 18.25, and 18.40° 2θ±0.04° 2θ. In one embodiment, the XRPD pattern further comprises peaks at 20.92, 22.36, and 23.19° 2θ0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.04° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, the pharmaceutical composition provided herein comprises free base of Compound 1, which is a solid form characterized by an XRPD pattern comprising peaks at 14.63, 18.02, 18.25, and 18.40° 2θ±0.02° 2θ. In one embodiment, the XRPD pattern further comprises peaks at 20.92, 22.36, and 23.19° 2θ0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ0.02° 2θ. In one embodiment, the XRPD pattern does not contain a peak at 14.21° 2θ±0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, the pharmaceutical composition provided herein comprises free base of Compound 1, which is a solid form characterized by an XRPD pattern comprising peaks at 14.6, 18.0, 18.3, and 18.4° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, the pharmaceutical composition provided herein comprises free base of Compound 1, which is a solid form characterized by an XRPD pattern comprising peaks at 14.63, 18.02, 18.25, and 18.40° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, the pharmaceutical composition provided herein comprises free base of Compound 1, which is a solid form characterized by an XRPD pattern comprising peaks at approximately 14.6, 18.3, 18.4, and 18.8° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.3, 18.4, 18.8, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, the pharmaceutical composition provided herein comprises free base of Compound 1, which is a solid form characterized by an XRPD pattern comprising peaks at 14.6, 18.3, 18.4, and 18.8° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, the pharmaceutical composition provided herein comprises free base of Compound 1, which is a solid form characterized by an XRPD pattern comprising peaks at 14.63, 18.25, 18.40, and 18.75° 2θ±0.04° 2θ. In one embodiment, the XRPD pattern further comprises peaks at 20.92, 22.36, and 23.190 2θ 0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.040 2θ.

In one embodiment, the pharmaceutical composition provided herein comprises free base of Compound 1, which is a solid form characterized by an XRPD pattern comprising peaks at 14.6, 18.3, 18.4, and 18.8° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, the pharmaceutical composition provided herein comprises free base of Compound 1, which is a solid form characterized by an XRPD pattern comprising peaks at 14.63, 18.25, 18.40, and 18.75° 2θ±0.02° 2θ. In one embodiment, the XRPD pattern further comprises peaks at 20.92, 22.36, and 23.19° 2θ0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ0.02° 2θ. In one embodiment, the XRPD pattern does not contain a peak at 14.21° 2θ±0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, the pharmaceutical composition provided herein comprises free base of Compound 1, which is a solid form characterized by an XRPD pattern comprising peaks at 14.6, 18.3, 18.4, and 18.8° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, the pharmaceutical composition provided herein comprises free base of Compound 1, which is a solid form characterized by an XRPD pattern comprising peaks at 14.63, 18.25, 18.40, and 18.75° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, the pharmaceutical composition provided herein comprises free base of Compound 1, which is a solid form characterized by an XRPD pattern that matches the XRPD pattern presented in FIG. 2.

In one embodiment, without being limited to any particular theory, compared to Form K, the XRPD peaks in Form K' shift slightly to higher ° 2θ values, suggesting Form K' has slightly contracted lattice.

In one embodiment, the XRPD patterns are obtained using Cu Kα radiation.

(b) Mannitol Based Pharmaceutical Composition

In one embodiment, the carrier or diluent in the pharmaceutical composition provided herein is mannitol.

In one embodiment, the pharmaceutical composition further comprises a glidant, an acidifier, a lubricant, or a mixture thereof.

In one embodiment, provided herein is a pharmaceutical composition, comprising: 1) Compound 1, or an enantiomer, mixture of enantiomers, tautomer, isotopolog, or pharmaceutically acceptable salt thereof, at an amount of from about 0.05 to about 3% w/w; 2) mannitol at an amount of from about 80 to about 98% w/w; 3) a glidant at an amount of from about 0 to about 10% w/w; 4) an acidifier at an amount of from about 0 to about 6% w/w; and 5) a lubricant at an amount of from about 0 to about 8% w/w.

In one embodiment, Compound 1, or an enantiomer, mixture of enantiomers, tautomer, isotopolog, or pharmaceutically acceptable salt thereof, is free base of Compound 1. In one embodiment, the free base of Compound 1 is a crystalline free base of Compound 1. In one embodiment, the free base of Compound 1 is characterized by an XRPD pattern comprising peaks at approximately 14.6, 18.2, and 18.3° 2θ.

In one embodiment, the amount of Compound 1, or an enantiomer, mixture of enantiomers, tautomer, isotopolog, or pharmaceutically acceptable salt thereof, is from about 0.05 to about 3% w/w (of the total weight of the pharmaceutical composition). In one embodiment, the amount is from about 0.05 to about 2% w/w. In one embodiment, the amount is from about 0.1 to about 1.5% w/w. In one embodiment, the amount is from about 0.13 to about 1% w/w. In one embodiment, the amount is from about 0.13 to about 0.5% w/w. In one embodiment, the amount is from about 0.5 to about 1% w/w.

In one embodiment, the amount of Compound 1, or an enantiomer, mixture of enantiomers, tautomer, isotopolog, or pharmaceutically acceptable salt thereof, is about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3% w/w. In one embodiment, the amount is about 0.13% w/w. In one embodiment, the amount is about 0.5% w/w. In one embodiment, the amount is about 1% w/w.

In one embodiment, the mannitol is spray dried. In one embodiment, the mannitol has a crystalline grade of 200 SD (e.g., pearlitol 200 SD). In one embodiment, the mannitol has a crystalline grade of 100 SD (e.g., pearlitol 100 SD).

In one embodiment, the amount of mannitol is from about 80 to about 98% w/w (of the total weight of the pharmaceutical composition). In one embodiment, the amount of mannitol is from about 85 to about 95% w/w. In one embodiment, the amount of mannitol is from about 90 to about 93% w/w.

In one embodiment, the amount of mannitol is about 80, about 81, about 82, about 83, about 84, about 85, about 86, about 87, about 88, about 88.5, about 89, about 89.5, about 90, about 90.5, about 91, about 91.5, about 92, about 92.5, about 93, about 94, about 95, about 96, about 97, or about 98% w/w. In one embodiment, the amount of mannitol is about 90% w/w. In one embodiment, the amount of mannitol is about 91.5% w/w. In one embodiment, the amount of mannitol is about 92.4% w/w.

In one embodiment, the glidant is silica dimethyl silylate or colloidal silicon dioxide. In one embodiment, the glidant is silica dimethyl silylate. In one embodiment, the glidant is colloidal silicon dioxide.

In one embodiment, the glidant is a hydrophobic glidant. In one embodiment, the glidant is Aerosil R972.

In one embodiment, the glidant is a hydrophilic glidant. In one embodiment, the glidant has a surface area of about 200 m$^2$/g. In one embodiment, the glidant has a surface area of about 300 m$^2$/g. In one embodiment, the glidant is Aerosil 200. In one embodiment, the glidant is Aerosil 300.

In one embodiment, the amount of the glidant is from about 0 to about 10% w/w (of the total weight of the pharmaceutical composition). In one embodiment, the amount of the glidant is from about 0 to about 4% w/w. In one embodiment, the amount of the glidant is from about 0.25 to about 3% w/w. In one embodiment, the amount of the glidant is from about 0.5 to about 2% w/w.

In one embodiment, the amount of the glidant is about 0, about 0.1, about 0.2, about 0.25, about 0.3, about 0.35, about 0.4, about 0.45, about 0.5, about 0.55, about 0.6, about 0.65, about 0.7, about 0.75, about 0.8, about 0.9, about 1, about 1.1, about 1.2, about 1.3, about 1.4, about 1.5, about 1.75, about 2, about 2.25, about 2.5, about 2.75, about 3, about 3.25, about 3.5, about 3.75, about 4, about 4.5, about 5, about 5.5, about 6, about 6.5, about 7, about 7.5, about 8, about 8.5, about 9, about 9.5, or about 10% w/w. In one embodiment, the amount of the glidant is about 0.5% w/w. In one embodiment, the amount of the glidant is about 1% w/w. In one embodiment, the amount of the glidant is about 2% w/w. In one embodiment, the amount of the glidant is from about 0.5 to about 1% w/w.

In one embodiment, the glidant is silica dimethyl silylate, at an amount of about 0.5% w/w. In one embodiment, the glidant is colloidal silicon dioxide, at an amount of about 1% w/w. In one embodiment, the glidant is colloidal silicon dioxide, at an amount of about 2% w/w.

In one embodiment, the pharmaceutical compositions provided herein comprise an acidifier at an amount that is sufficient to keep the pH of the pharmaceutical composition no higher than 5. In one embodiment, without being limited by a particular theory, Compound 1 may degrade above pH 5.

In one embodiment, the pharmaceutical compositions provided herein comprise an acidifier at an amount that is sufficient to keep the pH of the pharmaceutical composition no higher than 4. In one embodiment, the pharmaceutical compositions provided herein comprise an acidifier at an amount that is sufficient to keep the pH of the pharmaceutical composition from about 2 to about 3.

In one embodiment, the acidifier is fumaric acid. In one embodiment, the acidifier is maleic acid. In one embodiment, the acidifier is succinic acid.

In one embodiment, the amount of the acidifier is from about 0 to about 6% w/w (of the total weight of the pharmaceutical composition). In one embodiment, the amount of the acidifier is from about 2 to about 5% w/w. In one embodiment, the amount of the acidifier is from about 2 to about 4% w/w.

In one embodiment, the amount of the acidifier is about 0, about 0.5, about 1, about 1.5, about 2, about 2.5, about 3, about 3.5, about 4, about 4.5, about 5, about 5.5, or about 6% w/w. In one embodiment, the amount of the acidifier is about 3% w/w.

In one embodiment, the acidifier is fumaric acid at an amount of about 3% w/w.

In one embodiment, the lubricant is stearic acid. In one embodiment, the lubricant is magnesium stearate.

In one embodiment, the amount of the lubricant is from about 0 to about 8% w/w (of the total weight of the pharmaceutical composition). In one embodiment, the amount of the lubricant is from about 2 to about 6% w/w.

In one embodiment, the amount of the lubricant is about 0, about 0.5, about 1, about 1.5, about 2, about 2.5, about 3, about 3.5, about 4, about 4.5, about 5, about 5.5, about 6, about 6.5, about 7, about 7.5, or about 8% w/w. In one embodiment, the amount of the lubricant is about 4% w/w.

In one embodiment, the lubricant is stearic acid at an amount of about 4% w/w.

In one embodiment, provided herein is a pharmaceutical composition, comprising: 1) Compound 1 (e.g., Form K) at an amount of from about 0.1 to about 0.2% w/w; 2) mannitol at an amount of from about 91 to about 93% w/w; 3) silica dimethyl silylate at an amount of from about 0.4 to about 0.6% w/w; 4) fumaric acid at an amount of from about 2 to about 4% w/w; and 5) stearic acid at an amount of from about 3 to about 5% w/w. In one embodiment, provided herein is a pharmaceutical composition, comprising: 1) Compound 1 (e.g., Form K) at an amount of about 0.13% w/w; 2) mannitol at an amount of about 92.37% w/w; 3) silica dimethyl silylate at an amount of about 0.5% w/w; 4) fumaric acid at an amount of about 3% w/w; and 5) stearic acid at an amount of about 4% w/w. In one embodiment, the pharmaceutical composition has a total weight of about 75 mg. In one embodiment, the pharmaceutical composition is contained in a size 4 capsule.

In one embodiment, provided herein is a pharmaceutical composition, comprising: 1) Compound 1 (e.g., Form K) at an amount of from about 0.4 to about 0.6% w/w; 2) mannitol at an amount of from about 90.5 to about 92.5% w/w; 3) colloidal silicon dioxide at an amount of from about 0.8 to about 1.2% w/w; 4) fumaric acid at an amount of from about 2 to about 4% w/w; and 5) stearic acid at an amount of from about 3 to about 5% w/w. In one embodiment, provided herein is a pharmaceutical composition, comprising: 1) Compound 1 (e.g., Form K) at an amount of about 0.5% w/w; 2) mannitol at an amount of about 91.5% w/w; 3) colloidal silicon dioxide at an amount of about 1% w/w; 4) fumaric acid at an amount of about 3% w/w; and 5) stearic acid at an amount of about 4% w/w. In one embodiment, the pharmaceutical composition has a total weight of about 100 mg. In one embodiment, the pharmaceutical composition is contained in a size 3 capsule.

In one embodiment, provided herein is a pharmaceutical composition, comprising: 1) Compound 1 (e.g., Form K) at an amount of from about 0.8 to about 1.2% w/w; 2) mannitol at an amount of from about 89 to about 91% w/w; 3) colloidal silicon dioxide at an amount of from about 1.8 to about 2.2% w/w; 4) fumaric acid at an amount of from about 2 to about 4% w/w; and 5) stearic acid at an amount of from about 3 to about 5% w/w. In one embodiment, provided herein is a pharmaceutical composition, comprising: 1) Compound 1 (e.g., Form K) at an amount of about 1% w/w; 2) mannitol at an amount of about 90% w/w; 3) colloidal silicon dioxide at an amount of about 2% w/w; 4) fumaric acid at an amount of about 3% w/w; and 5) stearic acid at an amount of about 4% w/w. In one embodiment, the pharmaceutical composition has a total weight of about 200 mg. In one embodiment, the pharmaceutical composition is contained in a size 2 capsule.

(c) Starch-Lactose Based Pharmaceutical Composition

In one embodiment, the carrier or diluent in the pharmaceutical composition provided herein is a mixture of starch and lactose.

In one embodiment, the pharmaceutical composition further comprising a glidant, an acidifier, a lubricant, a disintegrant, or a mixture thereof.

In one embodiment, provided herein is a pharmaceutical composition, comprising: 1) Compound 1, or an enantiomer, mixture of enantiomers, tautomer, isotopolog, or pharmaceutically acceptable salt thereof, at an amount of from about 0.05 to about 3% w/w; 2) a mixture of starch and lactose at an amount of from about 70 to about 90% w/w; 3) a glidant at an amount of from about 0 to about 10% w/w; 4) an acidifier at an amount of from about 0 to about 8% w/w; 5) a lubricant at an amount of from about 0 to about 8% w/w; and 6) a disintegrant at an amount of from about 0 to about 20% w/w.

In one embodiment, Compound 1, or an enantiomer, mixture of enantiomers, tautomer, isotopolog, or pharmaceutically acceptable salt thereof, is free base of Compound 1. In one embodiment, the free base of Compound 1 is a crystalline free base of Compound 1. In one embodiment, the free base of Compound 1 is characterized by an XRPD pattern comprising peaks at approximately 14.6, 18.2, and 18.3° 2θ.

In one embodiment, the amount of Compound 1, or an enantiomer, mixture of enantiomers, tautomer, isotopolog, or pharmaceutically acceptable salt thereof, is from about 0.05 to about 3% w/w (of the total weight of the pharmaceutical composition). In one embodiment, the amount is from about 0.05 to about 2% w/w. In one embodiment, the amount is from about 0.1 to about 1.5% w/w. In one embodiment, the amount is from about 0.13 to about 1% w/w. In one embodiment, the amount is from about 0.13 to about 0.5% w/w. In one embodiment, the amount is from about 0.5 to about 1% w/w.

In one embodiment, the amount of Compound 1, or an enantiomer, mixture of enantiomers, tautomer, isotopolog, or pharmaceutically acceptable salt thereof, is about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3% w/w. In one embodiment, the amount is about 0.13% w/w. In one embodiment, the amount is about 0.5% w/w. In one embodiment, the amount is about 1% w/w.

In one embodiment, the starch is partially pregelatinized starch. In one embodiment, the starch is pregelatinized starch.

In one embodiment, the lactose is anhydrous lactose. In one embodiment, the lactose is lactose monohydrate. In one embodiment, the lactose is spray dried.

In one embodiment, the amount of the mixture of starch and lactose is from about 70 to about 90% w/w (of the total weight of the pharmaceutical composition). In one embodiment, the amount of the mixture of starch and lactose is from about 75 to about 85% w/w. In one embodiment, the amount of the mixture of starch and lactose is from about 80 to about 82% w/w.

In one embodiment, the amount of the mixture of starch and lactose is about 70, about 71, about 72, about 73, about 74, about 75, about 76, about 77, about 78, about 78.5, about 79, about 79.5, about 80, about 80.5, about 81, about 81.5, about 82, about 82.5, about 83, about 83.5, about 84, about 85, about 86, about 87, about 88, about 89, or about 90% w/w. In one embodiment, the amount of the mixture of starch and lactose is about 80% w/w. In one embodiment, the amount of the mixture of starch and lactose is about 80.5% w/w. In one embodiment, the amount of the mixture of starch and lactose is about 81.4% w/w.

In one embodiment, the amount of the starch is from about 17 to about 22% w/w, and the amount of the lactose is from about 53 to about 68% w/w. In one embodiment, the amount of the starch is from about 18 to about 21% w/w, and the amount of the lactose is from about 57 to about 64% w/w. In one embodiment, wherein the amount of the starch is from about 19 to about 20% w/w, and the amount of the lactose is from about 61 to about 62% w/w.

In one embodiment, the amount of the starch is about 17, about 17.5, about 18, about 18.5, about 19, about 19.5, about 20, about 20.5, about 21, about 21.5, or about 22% w/w. In one embodiment, the amount of the starch is about 19% w/w. In one embodiment, the amount of the starch is about 19.5% w/w. In one embodiment, the amount of the starch is about 20% w/w.

In one embodiment, the amount of the lactose is about 53, about 54, about 55, about 56, about 57, about 58, about 58.5, about 59, about 59.5, about 60, about 60.5, about 61, about 61.5, about 62, about 62.5, about 63, about 64, about 65, about 66, about 67, or about 68% w/w. In one embodiment, the amount of the lactose is about 61% w/w. In one embodiment, the amount of the lactose is about 61.4% w/w.

In one embodiment, the weight ratio of the starch to the lactose is from about 1:2 to about 1:4. In one embodiment, the weight ratio of the starch to the lactose is from about 1:2.5 to about 1:3.5. In one embodiment, the weight ratio of the starch to the lactose is from about 1:3 to about 1:3.3. In one embodiment, the weight ratio of the starch to the lactose is about 1:3. In one embodiment, the weight ratio of the starch to the lactose is about 1:3.1. In one embodiment, the weight ratio of the starch to the lactose is about 1:3.2. In one embodiment, the weight ratio of the starch to the lactose is about 1:3.3.

In one embodiment, the glidant is silica dimethyl silylate or colloidal silicon dioxide. In one embodiment, the glidant is silica dimethyl silylate. In one embodiment, the glidant is colloidal silicon dioxide.

In one embodiment, the glidant is a hydrophobic glidant. In one embodiment, the glidant is Aerosil R972.

In one embodiment, the glidant is a hydrophilic glidant. In one embodiment, the glidant has a surface area of about 200 $m^2/g$. In one embodiment, the glidant has a surface area of about 300 $m^2/g$. In one embodiment, the glidant is Aerosil 200. In one embodiment, the glidant is Aerosil 300.

In one embodiment, the amount of the glidant is from about 0 to about 10% w/w (of the total weight of the pharmaceutical composition). In one embodiment, the amount of the glidant is from about 0 to about 4% w/w. In one embodiment, the amount of the glidant is from about 0.25 to about 3% w/w. In one embodiment, the amount of the glidant is from about 0.5 to about 2% w/w. In one embodiment, the amount of the glidant is from about 0.5 to about 1% w/w.

In one embodiment, the amount of the glidant is about 0, about 0.1, about 0.2, about 0.25, about 0.3, about 0.35, about 0.4, about 0.45, about 0.5, about 0.55, about 0.6, about 0.65, about 0.7, about 0.75, about 0.8, about 0.9, about 1, about 1.1, about 1.2, about 1.3, about 1.4, about 1.5, about 1.75, about 2, about 2.25, about 2.5, about 2.75, about 3, about 3.25, about 3.5, about 3.75, about 4, about 4.5, about 5, about 5.5, about 6, about 6.5, about 7, about 7.5, about 8, about 8.5, about 9, about 9.5, or about 10% w/w. In one embodiment, the amount of the glidant is about 0.5% w/w. In one embodiment, the amount of the glidant is about 1% w/w. In one embodiment, the amount of the glidant is about 2% w/w.

In one embodiment, the glidant is silica dimethyl silylate, at an amount of about 0.5% w/w. In one embodiment, the glidant is colloidal silicon dioxide, at an amount of about 1% w/w. In one embodiment, the glidant is colloidal silicon dioxide, at an amount of about 2% w/w.

In one embodiment, the pharmaceutical compositions provided herein comprise an acidifier at an amount that is sufficient to keep the pH of the pharmaceutical composition no higher than 5. In one embodiment, without being limited by a particular theory, Compound 1 may degrade above pH 5.

In one embodiment, the pharmaceutical compositions provided herein comprise an acidifier at an amount that is sufficient to keep the pH of the pharmaceutical composition no higher than 4. In one embodiment, the pharmaceutical compositions provided herein comprise an acidifier at an amount that is sufficient to keep the pH of the pharmaceutical composition from about 2 to about 3.

In one embodiment, the acidifier is fumaric acid. In one embodiment, the acidifier is maleic acid. In one embodiment, the acidifier is succinic acid.

In one embodiment, the amount of the acidifier is from about 0 to about 8% w/w (of the total weight of the pharmaceutical composition). In one embodiment, the amount of the acidifier is from about 1 to about 7% w/w. In one embodiment, the amount of the acidifier is from about 2 to about 6% w/w. In one embodiment, the amount of the acidifier is from about 3 to about 5% w/w.

In one embodiment, the amount of the acidifier is about 0, about 0.5, about 1, about 1.5, about 2, about 2.5, about 3, about 3.5, about 4, about 4.5, about 5, about 5.5, about 6, about 6.5, about 7, about 7.5, or about 8% w/w. In one embodiment, the amount of the acidifier is about 4% w/w.

In one embodiment, the acidifier is fumaric acid at an amount of about 4% w/w.

In one embodiment, the lubricant is stearic acid. In one embodiment, the lubricant is magnesium stearate.

In one embodiment, the amount of the lubricant is from about 0 to about 8% w/w (of the total weight of the pharmaceutical composition). In one embodiment, the amount of the lubricant is from about 1 to about 7% w/w. In one embodiment, the amount of the lubricant is from about 2 to about 6% w/w. In one embodiment, the amount of the lubricant is from about 3 to about 5% w/w.

In one embodiment, the amount of the lubricant is about 0, about 0.5, about 1, about 1.5, about 2, about 2.5, about 3, about 3.5, about 4, about 4.5, about 5, about 5.5, about 6, about 6.5, about 7, about 7.5, or about 8% w/w. In one embodiment, the amount of the lubricant is about 4% w/w.

In one embodiment, the lubricant is stearic acid at an amount of about 4% w/w.

In one embodiment, the disintegrant is sodium starch glycolate. In one embodiment, the disintegrant is croscarmellose sodium. In one embodiment, the disintegrant is crospovidone.

In one embodiment, the amount of the disintegrant is from about 0 to about 20% w/w (of the total weight of the pharmaceutical composition). In one embodiment, the amount of the disintegrant is from about 5 to about 15% w/w. In one embodiment, the amount of the disintegrant is from about 8 to about 12% w/w.

In one embodiment, the amount of the disintegrant is about 0, about 2, about 4, about 5, about 6, about 7, about 8, about 9, about 10, about 11, about 12, about 13, about 14, about 15, about 16, about 18, or about 20% w/w. In one embodiment, the amount of the disintegrant is about 10% w/w.

In one embodiment, the disintegrant is sodium starch glycolate at an amount of about 10% w/w. In one embodiment, the disintegrant is croscarmellose sodium at an amount of about 10% w/w. In one embodiment, the disintegrant is crospovidone at an amount of about 10% w/w.

In one embodiment, provided herein is a pharmaceutical composition, comprising: 1) Compound 1 (e.g., Form K) at an amount of from about 0.1 to about 0.2% w/w; 2) partially pregelatinized starch at an amount of from about 19 to about 21% w/w and anhydrous lactose at an amount of from about 60 to about 62% w/w; 3) silica dimethyl silylate at an amount of from about 0.4 to about 0.6% w/w; 4) fumaric acid at an amount of from about 3 to about 5% w/w; 5) stearic acid at an amount of from about 3 to about 5% w/w; and 6) sodium starch glycolate at an amount of from about 9 to about 11% w/w. In one embodiment, provided herein is a pharmaceutical composition, comprising: 1) Compound 1 (e.g., Form K) at an amount of about 0.13% w/w; 2) partially pregelatinized starch at an amount of about 20% w/w and anhydrous lactose at an amount of about 61.4% w/w; 3) silica dimethyl silylate at an amount of about 0.5% w/w; 4) fumaric acid at an amount of about 4% w/w; 5) stearic acid at an amount of about 4% w/w; and 6) sodium starch glycolate at an amount of about 10% w/w. In one embodiment, the pharmaceutical composition has a total weight of about 75 mg. In one embodiment, the pharmaceutical composition is contained in a size 4 capsule.

In one embodiment, provided herein is a pharmaceutical composition, comprising: 1) Compound 1 (e.g., Form K) at an amount of from about 0.4 to about 0.6% w/w; 2) partially pregelatinized starch at an amount of from about 19 to about 20% w/w and anhydrous lactose at an amount of from about 60 to about 62% w/w; 3) colloidal silicon dioxide at an amount of from about 0.8 to about 1.2% w/w; 4) fumaric acid at an amount of from about 3 to about 5% w/w; 5) stearic acid at an amount of from about 3 to about 5% w/w; and 6) sodium starch glycolate at an amount of from about 9 to about 11% w/w. In one embodiment, provided herein is a pharmaceutical composition, comprising: 1) Compound 1 (e.g., Form K) at an amount of about 0.5% w/w; 2) partially pregelatinized starch at an amount of about 19.5% w/w and anhydrous lactose at an amount of about 61% w/w; 3) colloidal silicon dioxide at an amount of about 1% w/w; 4) fumaric acid at an amount of about 4% w/w; 5) stearic acid at an amount of about 4% w/w; and 6) sodium starch glycolate at an amount of about 10% w/w. In one embodiment, the pharmaceutical composition has a total weight of about 100 mg. In one embodiment, the pharmaceutical composition is contained in a size 3 capsule.

In one embodiment, provided herein is a pharmaceutical composition, comprising: 1) Compound 1 (e.g., Form K) at an amount of from about 0.8 to about 1.2% w/w; 2) partially pregelatinized starch at an amount of from about 18 to about 20% w/w and anhydrous lactose at an amount of from about 60 to about 62% w/w; 3) colloidal silicon dioxide at an amount of from about 0.8 to about 1.2% w/w; 4) fumaric acid at an amount of from about 3 to about 5% w/w; 5) stearic acid at an amount of from about 3 to about 5% w/w; and 6) sodium starch glycolate at an amount of from about 9 to about 11% w/w. In one embodiment, provided herein is a pharmaceutical composition, comprising: 1) Compound 1 (e.g., Form K) at an amount of about 1% w/w; 2) partially pregelatinized starch at an amount of about 19% w/w and anhydrous lactose at an amount of about 61% w/w; 3) colloidal silicon dioxide at an amount of about 1% w/w; 4) fumaric acid at an amount of about 4% w/w; 5) stearic acid at an amount of about 4% w/w; and 6) sodium starch glycolate at an amount of about 10% w/w. In one embodiment, the pharmaceutical composition has a total weight of about 200 mg. In one embodiment, the pharmaceutical composition is contained in a size 2 capsule.

(d) Additional Embodiments of the Pharmaceutical Compositions

In one embodiment, the pharmaceutical compositions provided herein can optionally further comprises one or more additional excipient. The additional excipients include, but are not limited to, wetting agent, solubilizer, crystallization stabilizer, anti-adherent, and precipitation inhibitor.

In one embodiment, the pharmaceutical compositions provided herein optionally further comprise one or more of Tween 80, Poloxamer 188, sodium lauryl sulfate (SLS), HPBCD, VitE-TPGS, HPMCAS-LF, HPMC E3, PVP VA64, PVP K30, HPC EXF, and Talc.

In one embodiment, the pharmaceutical compositions provided herein are formulated into a capsule. In one embodiment, the capsule is an HPMC capsule. In one embodiment, the capsule is a gelatin capsule.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

(e) Process for Making Dosage Forms

Pharmaceutical compositions (dosage forms) provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of hydroxypropyl methyl cellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process. In some embodiment, direct blending also helps minimizing degradation of the active ingredient.

Direct blending can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However, for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

In some embodiments, a dosage form or pharmaceutical composition provided is prepared by a process comprising one or more blending and delumping steps, followed by an encapsulation step. In some embodiments, the process further comprising preparing a pre-treatment mixture of one or more excipients and treating equipment used in the process with the pre-treatment mixture. In one embodiment, the pre-treatment mixture is prepared from one or more diluents and lubricants (e.g., a mannitol and stearic acid mixture, or an anhydrous lactose and stearic acid mixture). In one embodiment, the use of pre-treatment mixture helps minimizing sticking of the active ingredient to the equipment surfaces during the manufacturing process.

In some embodiments, a dosage form or pharmaceutical composition provided is prepared by a process comprising coating the active ingredient (e.g., Compound 1) with a hydrophobic silica. In one embodiment, the coating is conducted by blending the active ingredient and the hydrophobic silica to form a binary blend (before blending with additional excipients). In one embodiment, the coating is conducted by dispersing the active ingredient with the hydrophobic silica. In one embodiment, the hydrophobic silica is silica dimethyl silylate. In one embodiment, the hydrophobic silica is Aerosil R-972. In one embodiment, the dosage form or pharmaceutical composition has a relatively low active ingredient load, e.g., about 0.1 to about 0.2% w/w of the total weight, or about 0.1 mg active ingredient in an about 75 mg capsule.

5.3 Methods of Use

In one embodiment, provided herein is a method of treating multiple myeloma, which comprises administering to a patient a pharmaceutical composition provided herein. In one embodiment, provided herein is a pharmaceutical composition provided herein for use in a method of treating multiple myeloma, wherein the method comprises administering said pharmaceutical composition to a patient.

In one embodiment, provided herein is a method of preventing multiple myeloma, which comprises administering to a patient a pharmaceutical composition provided herein. In one embodiment, provided herein is a pharmaceutical composition provided herein for use in a method of preventing multiple myeloma, wherein the method comprises said compound to a patient.

In one embodiment, provided herein is a method of managing multiple myeloma, which comprises administering to a patient a pharmaceutical composition provided herein. In one embodiment, provided herein is a pharmaceutical composition provided herein for use in a method of managing multiple myeloma, wherein the method comprises administering said compound to a patient.

In one embodiment, also provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, comprising administering an effective amount of a pharmaceutical composition provided herein to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a pharmaceutical composition provided herein to patient having multiple myeloma. In another embodiment, provided herein are methods for achieving an increase in overall survival, progression-free survival, event-free survival, time to progression, or disease-free survival in a patient, comprising administering an effective amount of a pharmaceutical composition provided herein to patient having multiple myeloma. In another embodiment, provided herein are methods for achieving an increase in overall survival in a patient, comprising administering an effective amount of a pharmaceutical composition provided herein to patient having multiple myeloma. In another embodiment, provided herein are methods for achieving an increase in progression-free survival in a patient, comprising administering an effective amount of a pharmaceutical composition provided herein to patient having multiple myeloma. In another embodiment, provided herein are methods for achieving an increase in event-free survival in a patient, comprising administering an effective amount of a pharmaceutical composition provided herein to patient having multiple myeloma. In another embodiment, provided herein are methods for achieving an increase in time to progression in a patient, comprising administering an effective amount of a pharmaceutical composition provided herein to patient having multiple myeloma. In another embodiment, provided herein are methods for achieving an increase in disease-free survival in a patient, comprising administering an effective amount of a pharmaceutical composition provided herein to patient having multiple myeloma.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma.

In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smoldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a pharmaceutical composition provided herein. In another embodiment, methods provided herein encompass treating, preventing or managing multiple myeloma characterized by genetic abnormalities, such as Cyclin D translocations (for example, t(11; 14)(q13; q32); t(6; 14)(p21;32); t(12; 14)(p13; q32); or t(6;20); MMSET translocations (for example, t(4; 14)(p16; q32)); MAF translocations (for example, t(14; 16)(q32; q32); t(20;22); t(16; 22)(q11; q13); or t(14;20)(q32; q11)); or other chromosome factors (for example, deletion of 17p13, or chromosome 13; del(17/17p), nonhyperdiploidy, and gain(1 q)), by administering a therapeutically effective amount of a pharmaceutical composition provided herein.

In some embodiments, the methods comprise administering a therapeutically effective amount of a pharmaceutical composition provided herein as induction therapy. In some embodiments, the methods comprise administering a therapeutically effective amount of a pharmaceutical composition provided herein as consolidation therapy. In some embodiments, the methods comprise administering a therapeutically effective amount of a pharmaceutical composition provided herein as maintenance therapy.

In one particular embodiment of the methods described herein, the multiple myeloma is plasma cell leukemia.

In one embodiment of the methods described herein, the multiple myeloma is high risk multiple myeloma. In some such embodiments, the high risk multiple myeloma is relapsed or refractory. In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p) and t(14; 16)(q32; q32). In some such embodiments, the high risk multiple myeloma is relapsed or refractory to one, two or three previous treatments.

In one embodiment, the multiple myeloma is characterized by a p53 mutation. In one embodiment, the p53 mutation is a Q331 mutation. In one embodiment, the p53 mutation is an R273H mutation. In one embodiment, the p53 mutation is a K132 mutation. In one embodiment, the p53 mutation is a K132N mutation. In one embodiment, the p53 mutation is an R337 mutation. In one embodiment, the p53 mutation is an R337L mutation. In one embodiment, the p53 mutation is a W146 mutation. In one embodiment, the p53 mutation is an S261 mutation. In one embodiment, the p53 mutation is an S261T mutation. In one embodiment, the p53 mutation is an E286 mutation. In one embodiment, the p53 mutation is an E286K mutation. In one embodiment, the p53 mutation is an R175 mutation. In one embodiment, the p53 mutation is an R175H mutation. In one embodiment, the p53 mutation is an E258 mutation. In one embodiment, the p53 mutation is an E258K mutation. In one embodiment, the p53 mutation is an A161 mutation. In one embodiment, the p53 mutation is an A161T mutation.

In one embodiment, the multiple myeloma is characterized by homozygous deletion of p53. In one embodiment, the multiple myeloma is characterized by homozygous deletion of wild type p53.

In one embodiment, the multiple myeloma is characterized by wild type p53.

In one embodiment, the multiple myeloma is characterized by activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma is characterized by activation of C-MAF. In one embodiment, the multiple myeloma is characterized by activation of MAFB. In one embodiment, the multiple myeloma is characterized by activation of FGFR3 and MMset. In one embodiment, the multiple myeloma is characterized by activation of C-MAF, FGFR3, and MMset. In one embodiment, the multiple myeloma is characterized by activation of Cyclin D1. In one embodiment, the multiple myeloma is characterized by activation of MAFB and Cyclin D1. In one embodiment, the multiple myeloma is characterized by activation of Cyclin D.

In one embodiment, the multiple myeloma is characterized by one or more chromosomal translocations. In one embodiment, the chromosomal translocation is t(14; 16). In one embodiment, the chromosomal translocation is t(14;20). In one embodiment, the chromosomal translocation is t(4; 14). In one embodiment, the chromosomal translocations are t(4; 14) and t(14; 16). In one embodiment, the chromosomal translocation is t(11; 14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14; 16) and t(16;22). In one embodiment, the chromosomal translocations are t(14;20) and t(11; 14).

In one embodiment, the multiple myeloma is characterized by a Q331 p53 mutation, by activation of C-MAF, and by a chromosomal translocation at t(14; 16). In one embodiment, the multiple myeloma is characterized by homozygous deletion of p53, by activation of C-MAF, and by a chromosomal translocation at t(14; 16). In one embodiment, the multiple myeloma is characterized by a K132N p53 mutation, by activation of MAFB, and by a chromosomal translocation at t(14;20). In one embodiment, the multiple myeloma is characterized by wild type p53, by activation of FGFR3 and MMset, and by a chromosomal translocation at t(4; 14). In one embodiment, the multiple myeloma is characterized by wild type p53, by activation of C-MAF, and by a chromosomal translocation at t(14; 16). In one embodiment, the multiple myeloma is characterized by homozygous deletion of p53, by activation of FGFR3, MMset, and C-MAF, and by chromosomal translocations at t(4; 14) and t(14; 16). In one embodiment, the multiple myeloma is characterized by homozygous deletion of p53, by activation of Cyclin D1, and by a chromosomal translocation at t(11; 14). In one embodiment, the multiple myeloma is characterized by an R337L p53 mutation, by activation of Cyclin D1, and by a chromosomal translocation at t(11; 14). In one embodiment, the multiple myeloma is characterized by a W146 p53 mutation, by activation of FGFR3 and MMset, and by a chromosomal translocation at t(4; 14). In one embodiment, the multiple myeloma is characterized by an S261T p53 mutation, by activation of MAFB, and by chromosomal translocations at t(6;20) and t(20;22). In one embodiment, the multiple myeloma is characterized by an E286K p53 mutation, by activation of FGFR3 and MMset, and by a chromosomal translocation at t(4; 14). In one embodiment, the multiple myeloma is characterized by an R175H p53 mutation, by activation of FGFR3 and MMset, and by a chromosomal translocation at t(4; 14). In one embodiment, the multiple myeloma is characterized by an E258K p53 mutation, by activation of C-MAF, and by chromosomal translocations at t(14; 16) and t(16;22). In one embodiment, the multiple myeloma is characterized by wild type p53, by activation of MAFB and Cyclin D1, and by chromosomal translocations at t(14;20) and t(11; 14). In one embodiment, the multiple myeloma is characterized by an A161T p53 mutation, by activation of Cyclin D, and by a chromosomal translocation at t(11; 14).

In some embodiments of the methods described herein, the multiple myeloma is transplant eligible newly diagnosed multiple myeloma. In another embodiment, the multiple myeloma is transplant ineligible newly diagnosed multiple myeloma.

In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a pharmaceutical composition provided herein to a patient having relapsed/refractory multiple myeloma with impaired renal function.

In certain embodiments, provided herein are methods of treating, preventing, and/or managing multiple myeloma, including relapsed or refractory multiple myeloma in frail patients or a symptom thereof, comprising administering a therapeutically effective amount of a pharmaceutical composition provided herein to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, provided herein are methods of treating, preventing or managing multiple myeloma, comprising administering to a patient a therapeutically effective amount of a pharmaceutical composition provided herein wherein the multiple myeloma is fourth line relapsed/refractory multiple myeloma.

In certain embodiments, provided herein are methods of treating, preventing or managing multiple myeloma, comprising administering to a patient a therapeutically effective amount of a pharmaceutical composition provided herein as induction therapy, wherein the multiple myeloma is newly diagnosed, transplant-eligible multiple myeloma.

In certain embodiments, provided herein are methods of treating, preventing or managing multiple myeloma, comprising administering to a patient a therapeutically effective amount of a pharmaceutical composition provided herein as maintenance therapy after other therapy or transplant, wherein the multiple myeloma is newly diagnosed, transplant-eligible multiple myeloma prior to the other therapy or transplant.

In certain embodiments, provided herein are methods of treating, preventing or managing multiple myeloma, comprising administering to a patient a therapeutically effective amount of a pharmaceutical composition provided herein as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1.

In certain embodiments, provided herein are methods of treating, preventing or managing multiple myeloma, comprising administering to a patient a therapeutically effective amount of a pharmaceutical composition provided herein, wherein the multiple myeloma is high risk multiple myeloma, that is relapsed or refractory to one, two or three previous treatments.

In certain embodiments, provided herein are methods of treating, preventing or managing multiple myeloma, comprising administering to a patient a therapeutically effective amount of a pharmaceutical composition provided herein, wherein the multiple myeloma is newly diagnosed, transplant-ineligible multiple myeloma.

In certain embodiments, a therapeutically or prophylactically effective amount of the compound is from about from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1 for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the patient to be treated with one of the methods provided herein has not been treated with multiple myeloma therapy prior to the administration of a pharmaceutical composition provided herein. In certain embodiments, the patient to be treated with one of the methods provided herein has been treated with multiple myeloma therapy prior to the administration of a pharmaceutical composition provided herein. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

Depending on the state of the disease to be treated and the subject's condition, a pharmaceutical composition provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A pharmaceutical composition provided herein may be formulated, alone or together, in suitable dosage unit with pharmaceutically acceptable excipients, carriers, adjuvants and vehicles, appropriate for each route of administration.

In one embodiment, a pharmaceutical composition provided herein is administered orally. In another embodiment, a pharmaceutical composition provided herein is administered parenterally. In yet another embodiment, a pharmaceutical composition provided herein is administered intravenously.

A pharmaceutical composition provided herein can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A pharmaceutical composition provided herein can be administered once daily (QD or qd), or divided into multiple daily doses such as twice daily (BID or bid), three times daily (TID or tid), and four times daily (QID or qid). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 7 days to 52 weeks. The term "intermittent" or "intermittently" as used herein is intended to mean stopping and starting at either regular or irregular intervals. For example, intermittent administration of a pharmaceutical composition provided herein, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a pharmaceutical composition provided herein is administered once a day. In another embodiment, a pharmaceutical composition provided herein is administered twice a day. In yet another embodiment, a pharmaceutical composition provided herein is administered three times a day. In still another embodiment, a pharmaceutical composition provided herein is administered four times a day.

In one embodiment, a therapeutically effective amount of a pharmaceutical composition provided herein is administered in a treatment cycle which includes an administration period of up to 20 days followed by a rest period. In one embodiment, a therapeutically effective amount of a pharmaceutical composition provided herein is administered in a treatment cycle which includes an administration period of up to 15 days followed by a rest period. In one embodiment, a therapeutically effective amount of a pharmaceutical composition provided herein is administered in a treatment cycle which includes an administration period of up to 10 days followed by a rest period. In one embodiment, a therapeutically effective amount of a pharmaceutical composition provided herein is administered in a treatment cycle which includes an administration period of up to 7 days followed by a rest period. In one embodiment, a therapeutically effective amount of a pharmaceutical composition provided herein is administered in a treatment cycle which includes an administration period of up to 5 days followed by a rest period. In one embodiment, a therapeutically effective amount of a pharmaceutical composition provided herein is administered in a treatment cycle which includes an administration period of up to 4 days followed by a rest period. In one embodiment, a therapeutically effective amount of a pharmaceutical composition provided herein is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of a pharmaceutical composition provided herein on days 1 to 5 of a 28 day cycle. In another embodiment, the treatment cycle includes an administration of a pharmaceutical composition provided herein on days 1 to 10 of a 28 day cycle. In one embodiment, the treatment cycle includes an administration of a therapeutically effective amount of a pharmaceutical composition provided herein on days 1 to 21 of a 28 day cycle. In another embodiment, the treatment cycle includes an administration of a therapeutically effective amount of a pharmaceutical composition provided herein on days 1 to 5 of a 7 day cycle. In another embodiment, the treatment cycle includes an administration of a therapeutically effective amount of a pharmaceutical composition provided herein on days 1 to 7 of a 7 day cycle. In one embodiment, the treatment cycle includes an administration of a therapeutically effective amount of a pharmaceutical composition provided herein on days 1 to 10 and days 15 to 24 of a 28 day cycle (herein referred to as 20/28 dosing cycle). In one embodiment, the treatment cycle includes an administration of a therapeutically effective amount of a pharmaceutical composition provided herein on days 1 to 3 and days 15 to 18 of a 28 day cycle. In one embodiment, the treatment cycle includes an administration of a therapeutically effective amount of a pharmaceutical composition provided herein on days 1 to 7 and days 15 to 21 of a 28 day cycle (herein referred to as 14/28 dosing cycle). In one embodiment, the treatment cycle includes an administration of a therapeutically effective amount of a pharmaceutical composition provided herein on days 1 to 5 and days 15 to 19 of a 28 day cycle (herein referred to as 10/28 dosing cycle). In one embodiment, the treatment cycle includes an administration of a therapeutically effective amount of a pharmaceutical composition provided herein on days 1 to 3 and days 15 to 17 of a 28 day cycle (herein referred to as 6/28 dosing cycle).

In one embodiment, the treatment cycle includes an administration of a therapeutically effective amount of a pharmaceutical composition provided herein on days 1 to 14 of a 21 day cycle. In another embodiment, the treatment cycle includes an administration of a pharmaceutical composition provided herein on days 1 to 4 and 8 to 11 of a 21 day cycle. In one embodiment, the treatment cycle includes an administration of a therapeutically effective amount of a pharmaceutical composition provided herein on days 1 to 5 and 8 to 12 of a 21 day cycle. In another embodiment, the treatment cycle includes an administration of a therapeutically effective amount of a pharmaceutical composition provided herein on days 1 to 5 and 11 to 15 of a 21 day cycle. In another embodiment, the treatment cycle includes an administration of a therapeutically effective amount of a pharmaceutical composition provided herein on days 1 to 5, 8 to 12 and 15 to 19 of a 21 day cycle. In another embodiment, the treatment cycle includes an administration of a therapeutically effective amount of a pharmaceutical composition provided herein on days 1 to 4, 8 to 11 and 15 to 18 of a 21 day cycle. In another embodiment, the treatment cycle includes an administration of a therapeutically effective amount of a pharmaceutical composition provided herein on days 1 to 4, 8 to 10 and 15 to 17 of a 21 day cycle. In another embodiment, the treatment cycle includes an administration of a therapeutically effective amount of a pharmaceutical composition provided herein on days 1 to 3, and 8 to 11 of a 21 day cycle. In another embodiment, the treatment cycle includes an administration of a therapeutically effective amount of a pharmaceutical composition provided herein on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of a pharmaceutical composition provided herein is administered for 1 to 13 cycles of 28 days (e.g., about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering a pharmaceutical composition provided herein at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering a pharmaceutical composition provided herein at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering a pharmaceutical composition provided herein once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering a pharmaceutical composition provided herein once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering a pharmaceutical composition provided herein once a day at a dosage amount of about 0.1 mg on days 1 to 10 and 15 to 24 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering a pharmaceutical composition provided herein twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering a pharmaceutical composition provided herein twice a day at a dosage amount of about 0.2 mg on days 1 to 3 and 15 to 17 of a 28 day cycle. In one such embodiment, the pharmaceutical composition is administered on days 1 to 3 (morning and evening), day 14 (evening only), days 15 and 16 (morning and evening), and day 17 (morning only) of a 28 day cycle, for example in Cycle 1.

For clarity reasons, it is noted that, unless otherwise specified, the Compound 1 doses referred to herein refer to the amount of Compound 1 in its free base form. In case that for example a pharmaceutically acceptable salt of Compound 1 is used, the amounts given above will need to be adapted accordingly.

5.4 Combination Therapy with a Second Active Agent

A pharmaceutical composition provided herein can also be combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein and conventional therapy may provide a unique treatment regimen that is unexpectedly effective in certain patients. Without being limited by theory, it is believed that a pharmaceutical composition provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A pharmaceutical composition provided herein and other active ingredient can be administered to a patient prior to, during, or after the occurrence of the adverse effect associated with conventional therapy.

A pharmaceutical composition provided herein can also be combined or used in combination with other therapeutic agents useful in the treatment and/or prevention of multiple myeloma described herein.

In one embodiment, provided herein is a method of treating, preventing, or managing multiple myeloma, comprising administering to a patient a pharmaceutical composition provided herein in combination with one or more second active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a pharmaceutical composition provided herein can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein, as is quadruple therapy. In one embodiment, the second therapy is dexamethasone.

Administration of a pharmaceutical composition provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of a pharmaceutical composition provided herein is independent of the route of administration of a second therapy. In one embodiment, a pharmaceutical composition provided herein is administered orally. In another embodiment, a pharmaceutical composition provided herein is administered intravenously. Thus, in accordance with these embodiments, a pharmaceutical composition provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a pharmaceutical composition provided herein and a second therapy are administered by the same mode of administration, orally or by IV. In another embodiment, a pharmaceutical composition provided herein is administered by one mode of administration, e.g., by IV, whereas the second agent (an anti-multiple myeloma agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of multiple myeloma being treated or managed, the severity and stage of disease, and the amount of a pharmaceutical composition provided herein and any optional additional active agents concurrently administered to the patient.

One or more second active ingredients or agents can be used together with a pharmaceutical composition provided herein in the methods and compositions provided herein. Second active agents can be large molecules (e.g., proteins), small molecules (e.g., synthetic inorganic, organometallic, or organic molecules), or cell therapies (e.g., CAR cells).

Examples of second active agents that can be used in the methods and compositions described herein include one or more of melphalan, vincristine, cyclophosphamide, etoposide, doxorubicin, bendamustine, obinutuzmab, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336), a BCL2 inhibitor (for example, venetoclax or navitoclax), an MCL-1 inhibitor (for example, AZD5991, AMG176, MIK665, S64315, or S63845), an LSD-1 inhibitor (for example, ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile or a salt thereof), a corticosteroid (for example, prednisone), dexamethasone; an antibody (for example, a CS1 antibody, such as elotuzumab; a CD38 antibody, such as daratumumab or isatuximab; or a BCMA antibody or antibody-conjugate, such as GSK2857916 or BI 836909), a checkpoint inhibitor (as described herein), or CAR cells (as described herein).

In one embodiment, the second active agent used together with a pharmaceutical composition provided herein in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at an 8 mg dose on days 1 and 8 of a 21 day cycle. In some other embodiments, the dexamethasone is administered at an 8 mg dose on days 1, 4, 8 and 11 of a 21 day cycle. In some embodiments, the dexamethasone is administered at an 8 mg dose on days 1, 8, and 15 of a 28 day cycle. In some other embodiments, the dexamethasone is administered at an 8 mg dose on days 1, 4, 8, 11, 15 and 18 of a 28 day cycle. In some embodiments, the dexamethasone is administered at an 8 mg dose on days 1, 8, 15, and 22 of a 28 day cycle. In one such embodiment, the dexamethasone is administered at an 8 mg dose on days 1, 10, 15, and 22 of Cycle 1. In some embodiments, the dexamethasone is administered at an 8 mg dose on days 1, 3, 15, and 17 of a 28 day cycle. In one such embodiment, the dexamethasone is administered at an 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15, and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15, and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the second active agent used together with a pharmaceutical composition provided herein in the methods and compositions described herein is bortezomib. In yet another embodiment, the second active agent used together with a pharmaceutical composition provided herein in the methods and compositions described herein is daratumumab. In some such embodiments, the methods additionally comprise administration of dexamethasone. In some embodiments, the methods comprise administration of a pharmaceutical composition provided herein with a proteasome inhibitor as described herein, a CD38 inhibitor as described herein and a corticosteroid as described herein.

In another embodiment, the second active agent used together with a pharmaceutical composition provided herein in the methods and compositions described herein is panobinostat. In some such embodiments, the methods additionally comprise administration of dexamethasone.

In another embodiment, the second active agent used together with a pharmaceutical composition provided herein in the methods and compositions described herein is ACY241. In some such embodiments, the methods additionally comprise administration of dexamethasone.

In another embodiment, the second active agent used together with a pharmaceutical composition provided herein in the methods and compositions described herein is vincristine. In some such embodiments, the methods additionally comprise administration of dexamethasone.

In another embodiment, the second active agent used together with a pharmaceutical composition provided herein in the methods and compositions described herein is cyclophosphamide. In some such embodiments, the methods additionally comprise administration of dexamethasone.

In another embodiment, the second active agent used together with a pharmaceutical composition provided herein in the methods and compositions described herein is etoposide. In some such embodiments, the methods additionally comprise administration of dexamethasone.

In another embodiment, the second active agent used together with a pharmaceutical composition provided herein in the methods and compositions described herein is doxorubicin. In some such embodiments, the methods additionally comprise administration of dexamethasone.

In another embodiment, the second active agent used together with a pharmaceutical composition provided herein in the methods and compositions described herein is venetoclax. In some such embodiments, the methods additionally comprise administration of dexamethasone.

In another embodiment, the second active agent used together with a pharmaceutical composition provided herein in the methods and compositions described herein is AMG176. In some such embodiments, the methods additionally comprise administration of dexamethasone.

In another embodiment, the second active agent used together with a pharmaceutical composition provided herein in the methods and compositions described herein is MIK665. In some such embodiments, the methods additionally comprise administration of dexamethasone.

In another embodiment, the second active agent used together with a pharmaceutical composition provided herein in the methods and compositions described herein is GSK525762A. In some such embodiments, the methods additionally comprise administration of dexamethasone.

In another embodiment, the second active agent used together with a pharmaceutical composition provided herein in the methods and compositions described herein is OTX015. In some such embodiments, the methods additionally comprise administration of dexamethasone.

In another embodiment, the second active agent used together with a pharmaceutical composition provided herein in the methods and compositions described herein is 4-[2-(cyclopropylmethoxy)-5-(methanesulfonyl)phenyl]-2-methylisoquinolin-1(2H)-one. In some such embodiments, the methods additionally comprise administration of dexamethasone.

In another embodiment, the second active agent used together with a pharmaceutical composition provided herein in the methods and compositions described herein is 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile, or a salt thereof (for example a besylate salt). In some such embodiments, the methods additionally comprise administration of dexamethasone.

In certain embodiments, a pharmaceutical composition provided herein is administered in combination with checkpoint inhibitors. In one embodiment, one checkpoint inhibitor is used in combination with a pharmaceutical composition provided herein in connection with the methods provided herein. In another embodiment, two checkpoint inhibitors are used in combination with a pharmaceutical composition provided herein in connection with the methods provided herein. In yet another embodiment, three or more checkpoint inhibitors are used in combination with a pharmaceutical composition provided herein in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer*, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, a pharmaceutical composition provided herein can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMIB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin avP3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3, 4, 5, 6, 7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 1 05(11):4247-4254 (2005).

In certain embodiments, a pharmaceutical composition provided herein is administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

6. EXAMPLES

Certain embodiments of the invention are illustrated by the following non-limiting examples.

6.1 Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1)

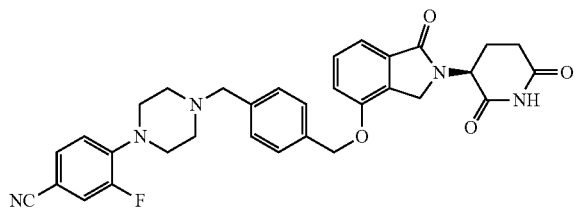 [SMILES: N#Cc1ccc(N2CCN(Cc3ccc(COc4cccc5c4CN([C@H]4CCC(=O)NC4=O)C5=O)cc3)CC2)c(F)c1]

tert-Butyl (4S)-5-amino-4-(benzyloxycarbonylamino)-5-oxo-pentanoate. To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude)

as a white solid, which was used in the next step without further purification. ¹H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

tert-Butyl (4S)-4,5-diamino-5-oxo-pentanoate. To a solution of tert-butyl (4S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. ¹H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate. Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) or until the filtrate had pH>3. The solid was dried under vacuum at 45° C. to give methyl 3-hydroxy-2-methyl-benzoate (700 g, 80.4% yield) as a gray solid. ¹H NMR: 400 MHz DMSO-$d_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate. Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl)silyl]oxy-benzoate. Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. ¹H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

tert-Butyl (4S)-5-amino-4-[4-[tert-butyl(dimethyl)silyl]oxy-1-oxo-isoindolin-2-yl]-5-oxo-pentanoate. To a solution of tert-butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

tert-Butyl (4S)-5-amino-4-(4-hydroxy-1-oxo-isoindolin-2-yl)-5-oxo-pentanoate. To a solution of tert-butyl (4S)-5-amino-4-[4-[tert-butyl(dimethyl)silyl]oxy-1-oxo-isoindolin-2-yl]-5-oxo-pentanoate (275 g, 613 mmol,) in methanol (2.0 L) was added tetrabutylammonium fluoride trihydrate (38.7 g, 123 mmol). The mixture was stirred at 18° C. for 16 h. The reaction mixture was concentrated to remove most of the methanol, and the residue was dissolved in dichloromethane/water (3 L/2 L). The organic layer was separated and washed with brine (1.0 L), dried over anhydrous sodium sulfate, filtered, and concentrated to give crude product, which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. ¹H NMR 400 MHz DMSO-$d_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(chloromethyl)benzyl)piperazin-1-yl)-3-fluorobenzonitrile. 1,4-bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-fluoro-4-(piperazin-1-yl)benzonitrile (20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acetate in hexanes over 800 mL followed by 20-80% ethyl acetate in hexanes over 4 L). Fractions containing desired product were combined and volatile organics were removed under reduced pressure to afford 4-(4-(4-(chloromethyl)benzyl)piperazin-1-yl)-3-fluorobenzonitrile (22.7 g, 66.0 mmol, 67.7% yield) as an off-white solid. ¹H NMR (400 MHz, CDCl$_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m z 344.2 [M+1]$^+$.

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate. (S)-tert-butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and washed with water (600 mL). The organic layer was dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some DMF remained. $^1$H NMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m z 642.4 [M+1]$^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile (Compound 1). (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The warm reaction mixture was poured directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

Recrystallization to Prepare Form K of Compound 1. (S)-4-(4-(4-(((2-(2,6-dioxopiperidin-3-yl)-1-oxoisoindolin-4-yl)oxy)methyl)benzyl)piperazin-1-yl)-3-fluorobenzonitrile was dissolved in acetone (35 L/Kg) and filtered to upgrade chiral purity. The filtrate was passed through a 0.45 μM filter into a clean reactor. After distillation (target volume 15 L/Kg), water (2 L/Kg) was charged to generate supersaturation. The batch was seeded with Form K and held at constant temperature with wet-milling through a recirculation loop at 40° C. Water (6 L/Kg) was charged at a constant rate of 1 (L/Kg)/h, with wet-milling at a reduced tip speed. The batch was cooled to 25° C. and then held for 3 h. The batch was filtered, washed and dried. Humid aging was performed followed by comilling to delump yielding (S)-4-(4-(4-(((2-(2,6-dioxopiperidin-3-yl)-1-oxoisoindolin-4-yl)oxy)methyl)benzyl)piperazin-1-yl)-3-fluorobenzonitrile as Form K. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

6.2 Antiproliferative Effects on Multiple Myeloma

Cell Culture Materials: Human multiple myeloma cell lines were purchased from the vendors and cultured at 37° C. with 5% CO$_2$ in the media as indicated in Table 1. Lenalidomide and pomalidomide resistant cell lines were obtained by methods as generally described previously (Lopez-Girona et al *Leukemia* 2012; 26(11): 2335). All cell lines were kept in log phase, and cell density and viability were monitored by trypan blue exclusion using the Vi-cell XR cell viability analyzer (Beckman Coulter, Brea, CA).

TABLE 1

Multiple Myeloma Cell Lines Tested

| MM Cell Line | Vendor/Source | Catalog Number | Culture Conditions |
| --- | --- | --- | --- |
| NCI-H929 | ATCC (Manassas, VA) | CRL-9068 | RPMI-1640, 10% FBS |
| NCI-H929-1051 | developed in-house, made resistant to lenalidomide | NA | RPMI-1640, 10% FBS |
| OPM2 | DSMZ (Braunschweig, Germany) | ACC-50 | RPMI-1640, 10% FBS |
| OPM2-P10 | developed in-house, made resistant to 10 μM pomalidomide | NA | RPMI-1640, 10% FBS |

Preparation of Solutions of Test Article: Compound 1 was plated into black 384-well plates (Corning Inc.) to a final DMSO volume of 0.1% assuming a maximal volume of 50 μL. A 10-point dose response starting at 10 μM with a 1:3 dilution was printed in duplicate by acoustic dispense using the EDC ATS-100 platform. Alternatively, the 10-point dose response starting at 10 μM with a 1:10 dilution, or starting at 100 nM with a 1:3 dilutions were used.

Cell Proliferation Assays: The effect of Compound 1 on the proliferation/viability of the hematological cell lines (Table 1), was assessed after 120 h incubation using CTG (Promega), according to manufacturer's instructions. Hematological cell lines were dispensed into compound plates by a Multidrop Combi Reagent Dispenser (Thermo Scientific, Waltham, MA) at a concentration of 0.1×10$^6$ cells per mL in a 50 μL total volume. At 120 h, 25 μL per well of CTG was dispensed by a Multidrop Combi Reagent Dispenser and adenosine triphosphate (ATP) release by viable cells was measured as relative luminescence units after 30 minutes using the Envision platform.

Results. Compound 1 Demonstrates Antiproliferative Activity Against MM Cell Lines. The MM cell lines selected for this study were lines sensitive and resistant to lenalidomide and/or pomalidomide (Table 1), two agents approved to treat myeloma patients. Proliferation was assessed using the CellTitre-Glo® assay. Results for cultures incubated with Compound 1 were normalized to results for control cultures for each cell line. The IC$_{50}$ for inhibition of cell growth by Compound 1 was determined for each cell line using ActivityBase software. Compound 1 potently inhibited cell proliferation in the four cell lines, as determined by the quantitative assessment of ATP levels present in the media after 120 h. The antiproliferative IC$_{50}$ values of Compound 1 ranged between 0.07 nM and 4.3 nM (Table 2). Compound 1 showed very potent multiple myeloma anti-proliferative activity even on cell lines that were lenalidomide- and/or pomalidomide-resistant.

TABLE 2

Inhibition of Cell Growth by Compound 1 in a MM Cell Lines in Liquid Culture

| Compd. No. | NCI-H929 120 h IC$_{50}$ | NCI-H929.1051 120 h IC$_{50}$ | OPM-2 120 h IC$_{50}$ | OPM-2.P10 120 h IC$_{50}$ |
|---|---|---|---|---|
| 1 | 0.07 nM | 1.0 nM | 0.07 nM | 4.3 nM |

6.3 Off-Target Effects of Compound 1

α1 Adrenergic and Dopamine D2 Receptors. Methods: Binding and functional assays for al adrenergic and dopamine D2 receptors were performed by Eurofins Cerep according to their methods.

α1 Adrenergic Receptor. Binding at 10 μM. The binding assay evaluated the affinity of test article for the non-selective al adrenergic receptor in rat cerebral cortex. Membrane homogenates of cerebral cortex were incubated in duplicate for 60 minutes at room temperature with 0.25 nM [$^3$H]prazosin in the absence or presence of test articles at 10 μM. After the incubation period, samples were filtered through glass fiber filters, the filters dried and then counted for radioactivity using a scintillation counter. Results are expressed as mean percent inhibition of control radioligand binding.

Binding IC$_{50}$. To determine the binding IC$_{50}$ for the non-selective al adrenergic receptor, varying concentrations of test article were incubated in duplicate with 0.25 nM [$^3$H]prazosin. Previously reported compound 3-(4-((4-((4-(2,4-difluorophenyl)piperazin-1-yl)methyl)benzyl)oxy)-1-oxoisoindolin-2-yl)piperidine-2,6-dione (Example 5.285 in U.S. Pat. No. 8,518,972) (Compound A) was tested at 0.01-30 μM. Compound B, the S-enantiomer of Compound A, was tested at 0.0003-10 μM. Compound 1 was assayed at 0.03-100 μM. Radioactivity was measured as described above. The IC$_{50}$ was defined as the concentration causing a half-maximum inhibition of control specific binding.

Antagonist activity. The antagonistic effects of test compounds on the α$_{1A}$ and α$_{1B}$ adrenergic receptors were measured using human receptor-transfected Chinese hamster ovary (CHO) cells. Antagonist activity was determined by measuring compound effect on agonist (epinephrine)-induced calcium mobilization in the α$_{1A}$ receptor assay or cAMP levels in the α$_{1B}$ receptor assay. In these experiments, CHO cells were incubated in duplicate at room temperature with test article and epinephrine at 3 nM in the α$_{1A}$ receptor assays or at 3000 nM in the α$_{1B}$ receptor assay. Compound A was tested in the α$_{1A}$ receptor assay at 0.01-30 μM. Compound B was tested in the α$_{1A}$ and α$_{1B}$ receptor assays at 0.0003-30 μM. Compound 1 was assayed at 0.03 to 30 μM in the α$_{1A}$ receptor assay and 0.03 to 100 μM in the α$_{1B}$ receptor assay. In the α$_{1A}$ receptor assay, cytosolic calcium levels were measured fluorometrically using the fluorescent probe, Fluo4 Direct. Intracellular cAMP levels in the α$_{1B}$ adrenergic receptor assay were measured by homogenous time-resolved fluorescence (HTRF). The antagonism IC$_{50}$ was defined as the concentration causing a half-maximum inhibition of control agonist response.

Dopamine D2 Receptor. Binding at 10 μM. The binding assay evaluated the affinity of test articles for the dopamine D2 receptor in transfected human embryonic kidney (HEK)-293 cells. For determining the binding in the D$_{2S}$ receptor assay, test article was incubated with 0.3 nM [$^3$H] methylspiperone or 1 nM [$^3$H] 7-hydroxy-2-N,N-dipropylaminotetralin (7-OH-DPAT). [$^3$H] Methylspiperone at 0.3 nM also was used as control ligand in the D$_{2L}$ binding assay. Cell membrane homogenates were incubated in duplicate at room temperature for 60 minutes with ligand in the absence or presence of test articles at 10 μM. After the incubation period, samples were filtered through glass fiber filters, the filters dried and then counted for radioactivity using a scintillation counter. Results are expressed as mean percent inhibition of control radioligand binding.

Binding IC$_{50}$. To determine the binding IC$_{50}$ in the D2 receptor assays, HEK-293 were tested as described above but with varying concentrations of test article. Compound A was tested at 0.01-30 μM in the D$_{2S}$ radioligand binding assay. Compound B was tested at 0.0003-10 μM in both the D$_{2S}$ and D$_{2L}$ binding assays. Compound 1 was tested at 0.03-100 μM in the D$_{2S}$ assay and 0.01-100 μM in the D$_{2L}$ assays. The IC$_{50}$ was defined as the concentration causing a half-maximum inhibition of control specific binding.

Agonist activity. The agonism of test compounds on the dopamine D$_{2S}$ receptor was assessed using human receptor-transfected HEK-293 cells. Agonist activity was determined by measuring compound effect on impedance modulation. In these experiments, HEK-293 cells were incubated in duplicate at 28° C. with test article. Compound A was tested at 0.01-30 μM. Compound B was tested at 0.0003-10 μM, while Compound 1 was assayed at 0.01-10 μM. Dopamine (3 μM) was used as an agonist control. Impedance measurements were monitored for 10 minutes after ligand addition using cellular dielectric spectroscopy. The EC$_{50}$ was defined as the concentration causing a half-maximum response, compared to the control agonist (dopamine) response.

Results. Binding at 10 μM at the al adrenergic and dopamine D2 receptors was evaluated for Compound 1, Compound A, Compound B and a number of compounds exemplified in U.S. Pat. No. 8,518,972 (as indicated by their example number Ex.) (Table 3). While the previously disclosed compounds fully inhibited binding of ligand at both receptors, surprisingly, Compound 1 showed greatly diminished ability to inhibit ligand binding, showing only 67/62% (al adrenergic receptor) and 55/52% (dopamine D$_{2S}$) inhibition of ligand binding, respectively.

TABLE 3

Effects of Compound A, Compound B, Compound 1 and previously reported compounds on α1 Adrenergic and Dopamine D2 Receptor

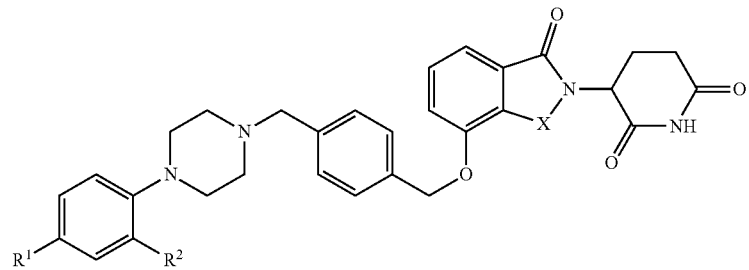

| Cmpd No. | R$^1$ | R$^2$ | X | Stereo | Adrenergic α1 % Inh. (@10 μM) | Dopamine D$_{2S}$ % Inh. (@10 μM) |
|---|---|---|---|---|---|---|
| 1 | CN | F | CH$_2$ | S | 62 | 52 |
| A | F | F | CH$_2$ | rac | 102 | 99 |
| B | F | F | CH$_2$ | S | 98 | 99 |
| Ex. 5.229 | H | H | CH$_2$ | rac | 98.3 | 98.7 |
| Ex. 5.273 | F | H | CH$_2$ | rac | 100.3 | 94.7 |
| Ex. 5.289 | F | H | CO | rac | 97.9 | 92.4 |

6.4 Drug-Excipient Compatibility Study

Figure 3:
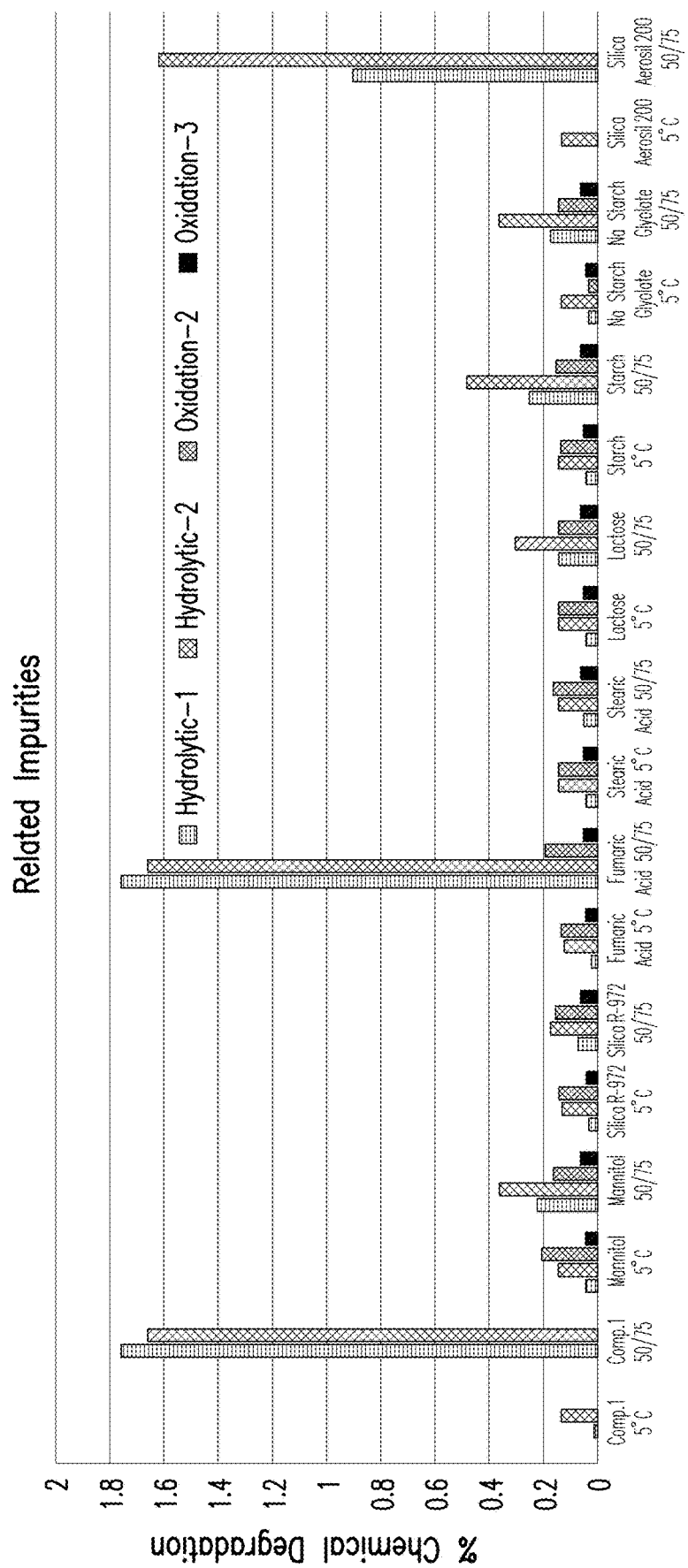
FIG. 3 shows hydrolysis and oxidation impurities results from a binary compatibility study.
Figure 4:
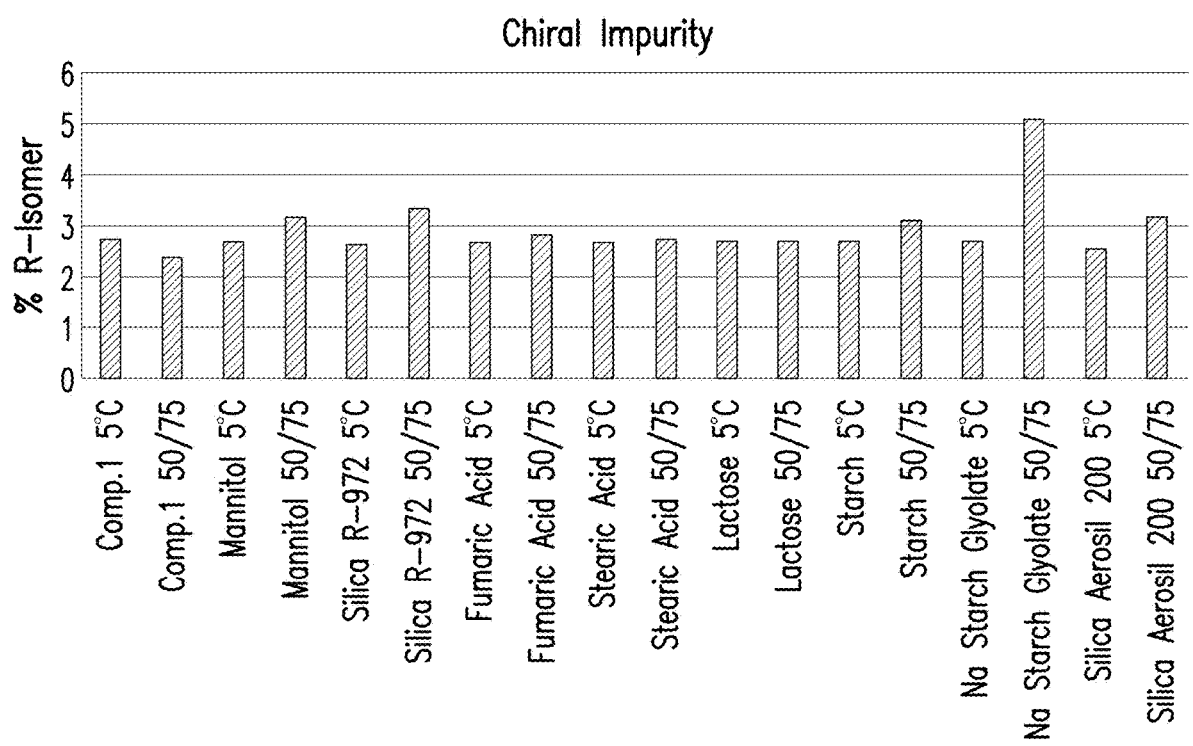
FIG. 4 shows chiral impurity results from a binary compatibility study.
Figure 5A:
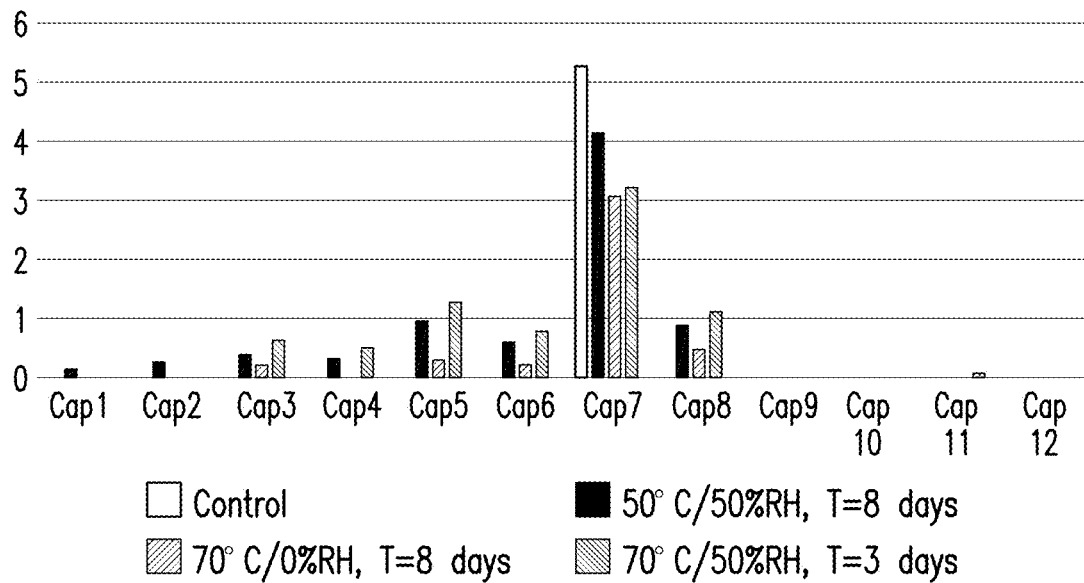
Figure 5B:
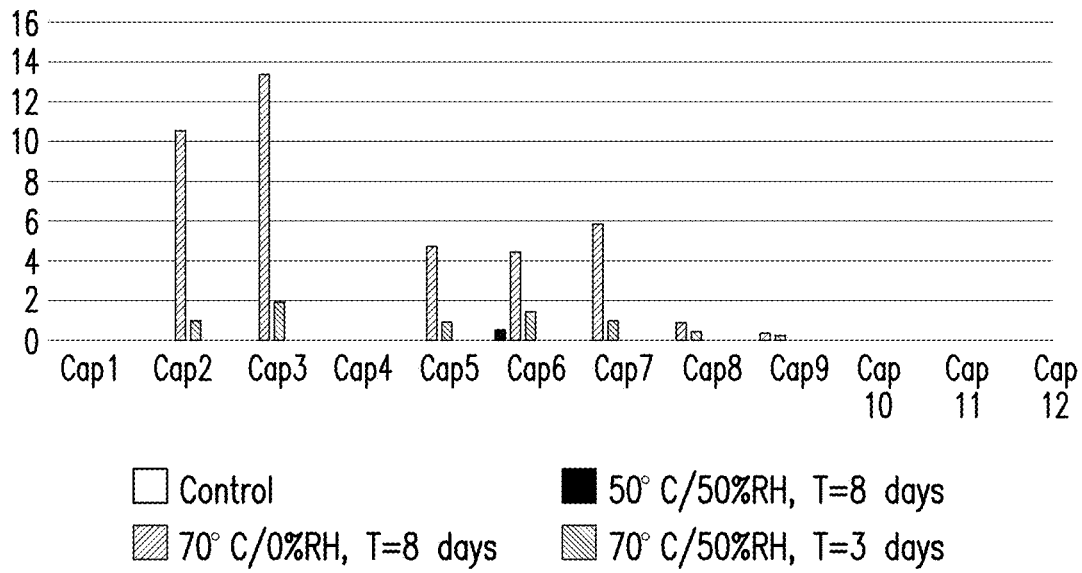
Figure 5C:
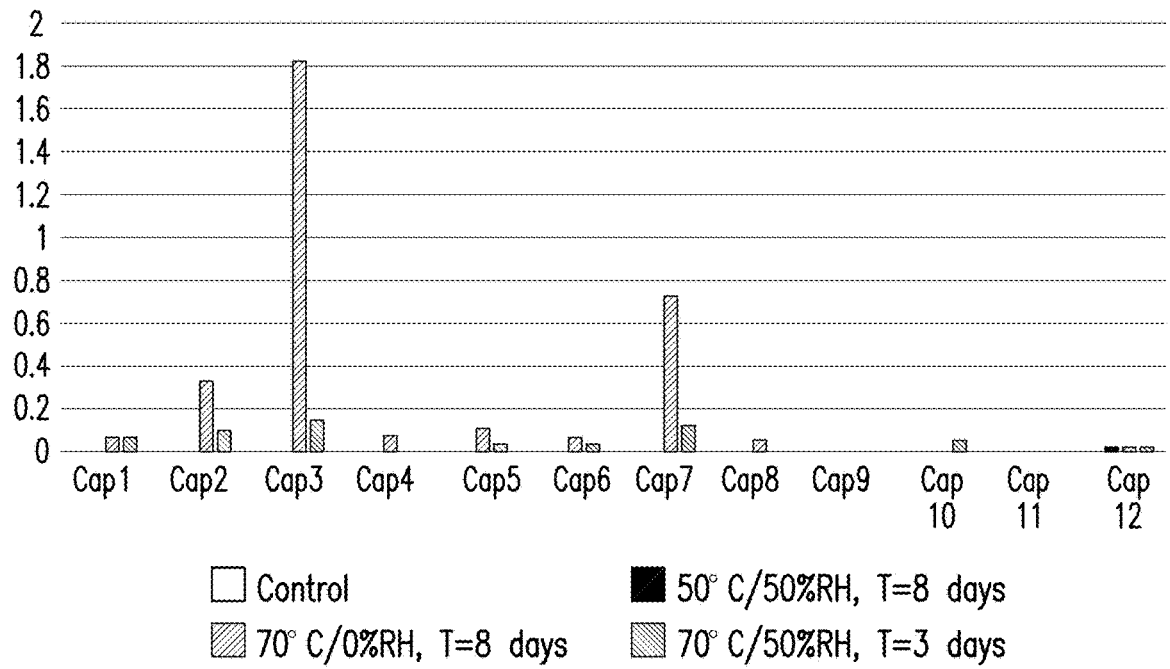
Figure 5D:
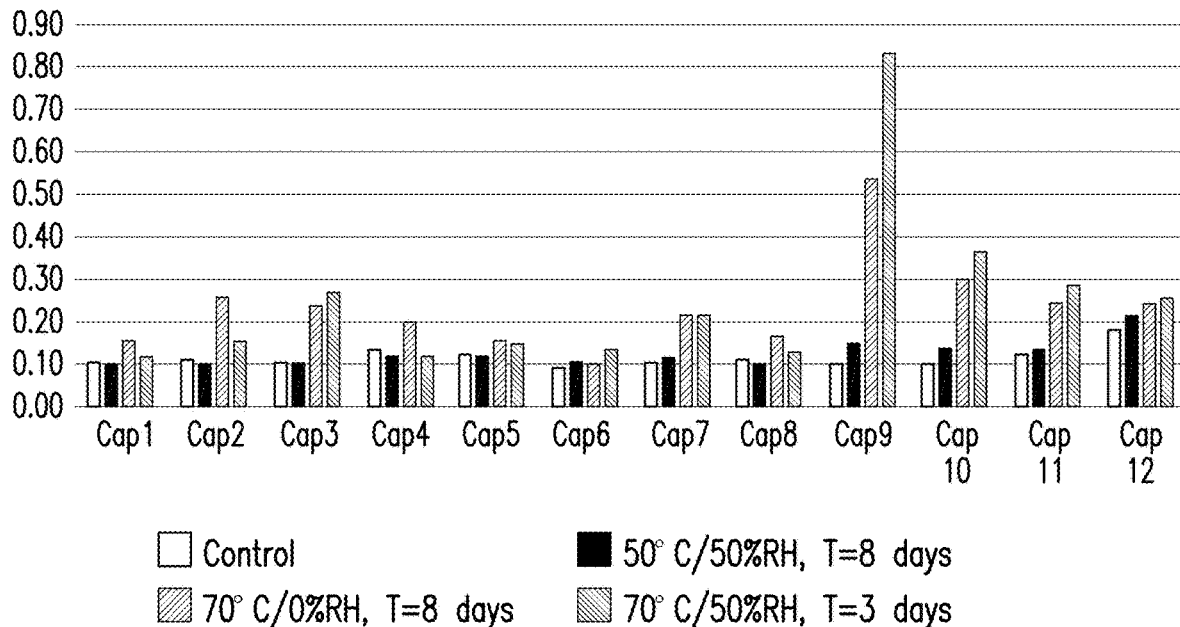

A binary drug-excipient compatibility study was conducted to identify suitable excipients for capsule formulation. The list of excipients and API to excipient ratios are tabulated in the following table. These binary mixtures were studied in open dish and subjected to 5° C. (control) and 50° C./75% RH conditions for 3 and 6 weeks respectively. Selective samples have been tested for chemical (impurities/degradants) and racemization (loss of chiral purity). The possible degradation pathways that could be shelf-life limiting for Compound 1 include hydrolysis, oxidation, and racemization (conversion of S-isomer to R-isomer). The hydrolysis and oxidation impurities results are shown in FIG. 3, and the chiral impurity results are shown in FIG. 4.

TABLE 4

List of Samples Evaluated for Compatibility with the Drug Substance

| Ingredients | Trade Name | Function | API to Excipient Ratio |
|---|---|---|---|
| Compound 1 | | API | 1 |
| Microcrystalline cellulose | Avicel 102 | Diluent | 1:200 |
| Spray dried lactose monohydrate | Fast Flo 316 | Diluent | |
| Mannitol spray dried | Pearlitol SD200 | Diluent | |
| Partially pregelatinized starch | Starch 1500 | Diluent | |
| Tween 80 | Tween 80 | Wetting agent/Solubilizer/Crystallization Stabilizer | |
| Poloxamer 188 | Lutrol F68 | Wetting agent/Solubilizer/Crystallization Stabilizer | |
| Sodium lauryl sulfate (SLS) | NA | Wetting agent/Solubilizer/Crystallization Stabilizer | |
| HPBCD | Kleptose | Solubilizer/Crystallization Stabilizer | |
| VitE-TPGS | NA | Solubilizer/Crystallization Stabilizer | |
| Croscarmellose sodium | Ac-di-Sol SD-711 | Disintegrant | |
| Crospovidone | Kollidon CL | Disintegrant | |
| Sodium starch glycolate (SSG) | Explotab | Disintegrant | |
| HPMCAS-LF | AQOAT AS | Crystallization Stabilizer | |
| HPMC E3 | Hypromellose | Binder/Crystallization Stabilizer | |
| PVP VA64 | Kollidon VA64 | Binder/Crystallization Stabilizer | |
| PVP K30 | Plasdone K30 | Binder/Crystallization Stabilizer | |
| HPC EXF | Klucel | Binder/Crystallization Stabilizer | |
| Succinic acid | NA | Acidifier | |
| Fumaric acid | Pharmaceutical grade | Acidifier | |

TABLE 4-continued

List of Samples Evaluated for Compatibility with the Drug Substance

| Ingredients | Trade Name | Function | API to Excipient Ratio |
|---|---|---|---|
| Silica dimethyl silylate | Aerosil R-972 | Glidant/De-agglomerant | |
| Silicon dioxide | Aerosil 200 | Glidant | |
| Silicon dioxide | Aerosil 300 | Glidant | |
| Talc | NA | Anti-adherent | |
| Stearic acid | Kolliwax | Lubricant | |
| Magnesium stearate | Hyqual | Lubricant | |
| HPMC capsule | Vcaps (Size #4) | Capsule shell | 1 |
| Gelatin Capsule | (Size #4) | Capsule shell | |

Compound 1 at elevated temperature and humidity levels (50° C./75% RH) undergoes hydrolysis. Diluents such as mannitol, starch, and lactose were evaluated as primary and secondary carriers. Lactose was found to be compatible with little decrease in chiral purity. Mannitol and starch were also found to be compatible, with some hydrolytic chemical degradation. Surfactant such as sodium lauryl sulfate (SLS) resulted in loss of chiral purity and increase in chemical degradation chiefly by hydrolysis. Of the evaluated disintegrants, sodium starch glycolate (SSG) was found to be compatible, whereas, crospovidone increased chemical degradation by oxidation and hydrolysis. Among the polymers evaluated as precipitation inhibitors, HPMC-E3 caused significant increase in unknown impurity (RRT 0.39), whereas, PVP-K30 and PVP-VA64 resulted in the formation of potential oxidation degradant (RRT 0.66). Also, PVP-K30 and PVP-VA64 not only caused chemical degradation by hydrolysis, but also loss of chiral purity. Both HPMC and gelatin based empty capsules exhibited good compatibility. From the shortlisted acidifiers, succinate acid was found to be chemically incompatible causing hydrolysis and also resulting in loss of chiral purity. Fumaric acid has been indicated as more compatible acidifier although at elevated ratio of 1:40 w/w it can cause chemical degradation by hydrolysis and loss of chiral purity. Glidants/de-agglomerants were also evaluated; Aerosil R972 was found to be most compatible, whereas, Aerosil 300 and Aerosil 200 were found to cause some chemical incompatibility by hydrolysis and loss of chiral purity. Of the hydrophilic Aerosil's (200 and 300), 200 was found to have better compatibility than Aerosil 300 due to the latter's high surface area-300 $m^2/g$ vs 200 $m^2/g$ catalyzing more hydrolysis. Stearic Acid was found to be chemically compatible, however, did cause some loss of chiral purity.

In summary, lactose, mannitol, pregelatinized starch, fumaric acid, stearic acid, Aerosil R972, Aerosil 300, HPBCD, sodium starch glycolate, and crospovidone were selected for further evaluation in blends. SLS, PVP-K30, PVP-VA64, and Aerosil 300 were found to be resulting in both losses of chiral purity and chemical degradation, whereas, Aerosil 200 was found to be affecting only chemical degradation.

6.5 Stability Screening of Mannitol & Starch-Lactose Based BIC Formulation

The stability of prototype blend in capsule (BIC) formulations based on mannitol, and starch-lactose as primary carriers was evaluated. Blends were prepared by dry mixing process using Turbula blender and filled into HPMC size #4 White Opaque capsules using Profill 100, and the components of the blends are provided in the following table. A rapid 3-day accelerated stability screening study was conducted for quick stability evaluation of BIC formulation.

TABLE 5

Prototype Mannitol, and starch-lactose based BIC formulations (Cap-1 to Cap-12)

| Batch Number Ingredients | Cap-1 | Cap-2 | Cap-3 | Cap-4 | Cap-5 | Cap-6 | Cap-7 | Cap-8 | Cap-9 | Cap-10 | Cap-11 | Cap-12 |
|---|---|---|---|---|---|---|---|---|---|---|---|---|
| | | | | | | % w/w | | | | | | |
| Compound 1 | 0.13 | 0.13 | 0.13 | 0.13 | 0.13 | 0.13 | 0.13 | 0.13 | 0.13 | 0.13 | 0.13 | 0.5 |
| Silica Dimethyl Silylate (Aerosil R972) | 0.2 | 0.2 | 0.2 | 0.2 | 0.2 | 0.2 | 0.2 | 0.2 | 0.2 | 0.2 | | 0.2 |
| Colloidal silicondioxide (Aerosil 300 Pharma) | | | | | | | | | | | 0.2 | |
| Partially pregelatinized Maize Starch (Starch 1500) | 30.0 | 30.0 | 64.67 | 64.67 | 44.0 | | | | | | | |
| Anhydrous Lactose (Supertab 24 AN) | 66.67 | 64.67 | 30.0 | 28.0 | 22.0 | | | | | | | |
| Mannitol (Pearlitol SD 200) | | | | | | 66.0 | 66.0 | 68.0 | 91.67 | 94.67 | 94.67 | 94.3 |
| Crospovidone (Kollidon CL) | | 2.0 | 2.0 | | 2.0 | 2.0 | 2.0 | | | | | |
| Sodium Starch Glycolate (Explotab) | | | | 2.0 | | | | | | | | |
| Polyvinylpyrrolidone (PVP-K30) | | | | | | | 26.67 | | | | | |

TABLE 5-continued

Prototype Mannitol, and starch-lactose based BIC formulations (Cap-1 to Cap-12)

| Batch Number Ingredients | Cap-1 | Cap-2 | Cap-3 | Cap-4 | Cap-5 | Cap-6 | Cap-7 | Cap-8 | Cap-9 | Cap-10 | Cap-11 | Cap-12 |
|---|---|---|---|---|---|---|---|---|---|---|---|---|
| | | | | | | % w/w | | | | | | |
| HPBCD (Kleptose) | | | | | 26.67 | | | 26.67 | | | | |
| Hypromellose (HPMC-E3) | | | | | | | 26.67 | | | | | |
| Sodium Lauryl Sulfate | | | | | | | | | 1.0 | | | |
| Fumaric Acid Pharmaceutical grade (Powder) | | | | 2.0 | 2.0 | 2.0 | 2.0 | 2.0 | 4.0 | 2.0 | 2.0 | 2.0 |
| Stearic Acid (Hystrene 5016 Veg) | 3.0 | 3.0 | 3.0 | 3.0 | 3.0 | 3.0 | 3.0 | 3.0 | 3.0 | 3.0 | 3.0 | 3.0 |
| Total (% w/w) | | | | | | 100.0 | | | | | | |
| Total Capsule Fill Weight (mg) | | | | | | 75.0 | | | | | | 100.0 |

The results from the accelerated stability screening are shown in FIG. 5A to FIG. 5D and FIG. 6.

RRT 4.2 minutes: Capsule-7 (mannitol BIC) containing HPMC-E3 was found to be least stable, followed by Capsule-5 (starch-lactose BIC) containing HPBCD and Capsule-8 (mannitol BIC) containing HPBCD. Polymers and complexing agents were found to enhance degradation product at RRT 4.2 minutes. Increase in humidity levels is catalyzing the RRT 4.2 minutes' degradation product.

The stability rank order for formulations exhibiting increase in 4.2 minutes' degradation product is as follows: Capsule-9 & 10>Cap-12>Cap-11>Cap-1>Cap-2>Cap-4>Cap-3>Cap-6>Cap-8>Cap-5>Cap-7.

In all, mannitol based batches containing fumaric acid were found to be most stable followed by starch-lactose based batches with or without fumaric acid.

RRT 7.6 minutes: Capsule-3 (starch-lactose BIC) was found to be least stable, followed by Cap-7 (mannitol BIC) containing HPMC-E3, and Cap-2 (starch-lactose BIC). Interestingly, Cap-2 and Cap-3 both contain the same excipients, except the proportions of starch-lactose. For Cap-2 formulation, starch is 30% w/w and lactose is 64.67% w/w, whereas, for Cap-3 formulation starch is 64.67% w/w and lactose is 30% w/w, which indicates that higher proportion of starch can result in greater RRT 7.6 minutes' degradation product. Cap-5 (starch-lactose BIC) containing HPBCD was also found to unstable. Cap-6 (mannitol BIC) containing PVP-K30 was also found to less stable compared to mannitol BIC formulation without PVP-K30 indicating PVP-K30 induced instability.

The stability rank order for formulations exhibiting increase in 7.6 minutes' degradation product is as follows: Capsule-9 & 11>Cap-12>Cap-10>Cap-8>Cap-4>Cap-6>Cap-1>Cap-5>Cap-2>Cap-7>Cap-3.

In all, mannitol based BIC formulations containing fumaric acid were found to be more stable.

RRT 7.1 minutes: Capsule-3 (starch-lactose BIC) containing crospovidone was found to be least stable. Capsule-1 (starch-lactose BIC) without crospovidone was found to have considerably better stability profile. Capsule-7 (mannitol BIC) containing HPMC-E3 was also found to be unstable, followed by Cap-6 (mannitol BIC) containing PVP-K30 and Cap-5 (starch-lactose BIC) containing HPBCD. The RRT 7.1 minutes' degradation impurity was increasing with increase in temperature (70° C.) at 0% RH.

The stability rank order for formulations showing increase in RRT 7.1 minutes' degradation product is as follows: Capsule-11>Cap-10>Cap-12>Cap-1>Cap-4>Cap-9>Cap-8>Cap-5>Cap-6>Cap-7>Cap-2 & Cap-3.

RRT 11.3 minutes: Capsule-9 (mannitol BIC) containing SLS was found to be least stable. In general, all mannitol based formulations with Aerosil R972 or with Aerosil 300 Pharma were found to be least stable. Of the starch-lactose based formulations, Cap-3 with crospovidone was found to be least stable. On contrary, starch-lactose BIC based formulations without crospovidone were found to have considerably better stability profile (Cap-1), however, mannitol based BIC formulations showed higher degradation.

The stability rank order for formulations showing increase in RRT 11.3 minutes' degradation product is as follows: Capsule-6>Cap-1>Cap-8>Cap-5>Cap-4>Cap-2>Cap-7>Cap-3>Cap-12>Cap-11>Cap-10>Cap-9.

Loss of Chiral Purity: From the FIG. 6, Cap-9 (mannitol BIC) containing SLS was found to enhance the conversion to R-isomer. Overall, starch-lactose based BIC formulations with or without crospovidone and fumaric acid were also found to enhance the conversion to R-isomer (Capsule-1, 2, 3, & 4). In general, Mannitol based BIC formulations with PVP-K30 (Cap-6) and HPBCD (Cap-8) were found to be most stable. Also, mannitol based BIC formulations with HPMC-E3 and starch-lactose containing HPBCD was also found to more stable than those without the polymers or complexing agents. Increase in temperature and reduction in humidity were also found to be favoring loss of chiral purity.

The stability rank order for formulations showing increase in loss of chirality purity is as follows: Capsule 6>Cap-8>Cap-12>Cap-5>Cap-7>Cap-10>Cap-11>Cap-4>Cap-2>Cap-3>Cap-1 & Cap-9.

In summary, mannitol based BIC formulations containing fumaric acid were found to exhibit best overall stability profiles. Although, inclusion of polymers or complexing agents were found to enhance degradation products, however, they were found to prevent loss of chiral purity. Starch-lactose based BIC formulations without fumaric acid (Cap-1, Cap-2, and Cap-3) was found to be unstable (chiral and related impurities) versus formulations with fumaric acid (Cap-4 and Cap-5). Hence, fumaric acid was selected as an acidifier to enhance drug product stability. Also, the stability profile of the drug product was found to be improving with higher drug loading as evident from Cap-10 (0.13% w/w Compound 1) versus Cap-12 (0.5% w/w Compound 1) mannitol based BIC formulations stability results. The ratio of starch-lactose was optimized by evaluating their stability profiles at 1:2 w/w versus 2:1 w/w. Formulations with higher portion of lactose (2 parts) were found to be more stable, than formulations containing higher portion of starch (2 parts) as evident from Cap-1 to Cap-4 starch-lactose based BIC formulations stability results.

6.6 Precipitation Risk Assessment of Prototype BIC Formulations

The precipitation risk of prototype BIC formulations were studied by a two-stage method (Stage 1 under sink condition and Stage 2 under non-sink condition) for high strength (2 mg). The formulation compositions are shown in the following table.

TABLE 6

Prototype Formulation Batches to evaluate precipitation risk by two-stage dissolution of 2 mg BIC

| Objective | 2 mg BIC precipitation inhibition Screening | | | |
|---|---|---|---|---|
| Batch Number | Cap19 | Cap20 | Cap21 | Cap22 |
| Ingredients | % w/w | % w/w | % w/w | % w/w |
| Compound 1 | 0.5 | 0.5 | 0.5 | 0.5 |
| Silica Dimethyl Silylate (Aerosil R972) | 2.0 | 2.0 | 2.0 | 2.0 |
| Mannitol (Pearlitol 200 SD) | | | 91.5 | 77.55 |
| Partially pregelatinized Maize Starch (Starch 1500) | 29.9 | 23.9 | | |
| Anhydrous Lactose (Supertab 24 AN) | 61.6 | 53.65 | | |
| Polyvinyl pyrrolidone (PVP-K30) HPBCD, 97% | | 13.95 | | 13.95 |
| Fumaric Acid Pharmaceutical grade (Powder) | 3.0 | 3.0 | 3.0 | 3.0 |
| Stearic Acid (Hystrene 5016 Veg) | 3.0 | 3.0 | 3.0 | 3.0 |
| Total (% w/w) | 100.0 | 100.0 | 100.0 | 100.0 |
| Total Capsule Fill Wt (mg) | 400.0 | 400.0 | 400.0 | 400.0 |

A two-stage dissolution study was carried out on prototype formulations, wherein the dissolution medium for Stage 1 was 0.01N HCl. From the two-stage dissolution studies, no precipitation was observed at pH 6.8 (90-150 mins) for any mannitol based and starch based BIC (FIG. 7). Based on the two-stage dissolution findings the precipitation risk is considered low for Compound 1.

The dissolution release profiles of starch-lactose based batches (Cap-19 & Cap-20) are observed to be slower than that of mannitol based batches (Cap-21 & Cap-22) with and without HPBCD. The slowdown of the dissolution was believed to be due to the following: the plug formation (gelation) inside the HPMC capsule, and the level of hydrophobic silica Aerosil R972 at 2% w/w. Therefore, the optimization of R972 was explored and 0.5% w/w Aerosil R972 level in starch-lactose BIC formulation was found to achieve comparable dissolution profile as that of mannitol based BIC formulation.

When combinations of mannitol with HPBCD (Cap-22), and starch-lactose with HPBCD (Cap-20) were evaluated against formulations without HPBCD (Cap-19 & Cap-21), the dissolution release profiles of formulations without HPBCD (Cap-19 & Cap-21) were found to be faster than their combinations (Cap-20 & Cap-22). In summary, based on two-stage dissolution results no precipitation was observed for BIC formulation without any precipitation inhibitor or solubilizer. Hence, it was determined that there is no need to incorporate precipitation inhibitor or solubilizer in the capsule formulation and that precipitation risk is considered low for Compound 1.

6.7 Prototype Formulations Screening to Achieve Fast Dissolution Release Rate from Starch-Lactose Based BIC Formulations Due to the plug formation the dissolution release profile from 2 mg starch-lactose BIC batch (Cap-19) was found to be slower than that of mannitol based BIC batch (Cap-21) as shown in FIG. 7. A formulation optimization was conducted to achieve fast release rate using different disintegrants as shown in the following table (Cap-24, Cap-25, & Cap-26). The dissolution release profiles of these formulations were compared with Cap-13, 0.1 mg BIC (same formulation as 2.0 mg Cap-19 BIC) formulation and Cap-27 (2 mg Binary BIC).

TABLE 7

Starch-lactose based prototype formulation batches to optimize dissolution rate by assessing different grades of disintegrants

| Objective | Dissolution Screening of 0.1 mg Starch-lactose based BIC | | | | 2.0 mg Binary BIC |
|---|---|---|---|---|---|
| Batch Number | Cap13 | Cap24 | Cap25 | Cap26 | Cap27 |
| Ingredients | % w/w | % w/w | % w/w | % w/w | %w/w |
| Compound 1 | 0.13 | 0.13 | 0.13 | 0.13 | 90.09 |
| Silica Dimethyl Silylate (Aerosil R972) | 2.0 | 2.0 | 2.0 | 2.0 | 9.91 |
| Partially pregelatinized Maize Starch (Starch 1500) | 30.0 | 28.0 | 27.0 | 27.0 | |
| Anhydrous Lactose (Supertab 24 AN) | 61.87 | 62.87 | 62.87 | 62.87 | |
| Crospovidone (Kollidon CL) | | 2.0 | | | |
| Sodium Starch Glycolate (Explotab) | | | 2.0 | | |
| Croscarmellose Sodium (Ac-di-Sol SD-711) | | | | 2.0 | |
| Fumaric Acid Pharmaceutical grade (Powder) | 3.0 | 3.0 | 4.0 | 4.0 | |
| Stearic Acid (Hystrene 5016 Veg) | 3.0 | 2.0 | 2.0 | 2.0 | |
| Total (% w/w) | 100.0 | 100.0 | 100.0 | 100.0 | 100.0 |

The dissolution release profiles using different disintegrants were not found to be significantly different (Cap-24, Cap-25, & Cap-26). The Cap-25 (2% w/w sodium starch glycolate) BIC formulation exhibited slightly better dissolution release profile versus Cap-24 (2% w/w crospovidone), and Cap-26 (2% w/w croscarmellose sodium), respectively. The disintegration time profiles for Cap-24, Cap-25, and Cap-26 were not found to be significantly different but were nevertheless better and consistent for Cap-25 containing 2% w/w SSG versus Cap-24 and Cap-26. The apparent role of hydrophobic Aerosil R972 over the formulations with disintegrants is evident by the 2 mg binary BIC with 10% w/w Aerosil R972 (Cap-27) dissolution profile, which demonstrated the slowest dissolution release profile among the five formulations. The control mannitol formulation (Cap-13 without disintegrant) exhibited slightly better overall dissolution release profile which also had 2% Aerosil R972, which indicates the impact of hydrophobic Aerosil R972 on retardation of dissolution release profile is more significant for starch-lactose based BIC formulations. Overall, no significant difference was observed in disintegration or dissolution by inclusion of SSG, croscarmellose sodium, or crospovidone disintegrant. The inclusion of SSG resulted in consistent dissolution profile.

Further dissolution exploratory studies were conducted to resolve the slower dissolution release profile for starch-lactose BIC with sodium starch glycolate selected as disintegrating agent of choice due to better stability of binary mixture and no negative effect on dissolution. Varying the levels of hydrophobic silica (Aerosil R972) and dissolution speeds (50 rpm vs 75 rpm) were assessed to resolve the slower dissolution release profile associated with starch-lactose based formulation as shown in the following table (Cap-29, 33, & 34).

TABLE 8

Starch-Lactose based prototype Formulation Batches to optimize dissolution rate varying the levels of Aerosil R972, and various levels of Sodium Starch Glycolate

| Objective | Dissolution Screening of 0.1 mg Starch-lactose based BIC | | | |
|---|---|---|---|---|
| Batch Number | Cap25 | Cap29 | Cap33 | Cap34 |
| Ingredients | % w/w | % w/w | % w/w | % w/w |
| Compound 1 | 0.13 | 0.13 | 0.13 | 0.13 |
| Silica Dimethyl Silylate (Aerosil R972) | 2.0 | 1.0 | 1.0 | 0.5 |
| Partially pregelatinized Maize Starch (Starch 1500) | 27.0 | 24.0 | 22.0 | 22.0 |
| Anhydrous Lactose (Supertab 24 AN) | 62.87 | 65.87 | 60.87 | 61.37 |
| Sodium Starch Glycolate (Explotab) | 2.0 | 2.0 | 10.0 | 10.0 |
| Fumaric Acid Pharmaceutical grade (Powder) | 4.0 | 5.0 | 4.0 | 4.0 |
| Stearic Acid (Hystrene 5016 Veg) | 2.0 | 2.0 | 2.0 | 2.0 |
| Total (% w/w) | 100.0 | 100.0 | 100.0 | 100.0 |

As shown in FIG. 8, the dissolution release profile of Cap-34 is significantly superior (~80% drug release in 30 minutes) when compared with Cap-25 (control—~30% drug release in 30 minutes). Although the drug release is still not 100%, it can be inferred that reducing the levels of Aerosil R972 from 2% to 0.5% levels, increasing the levels of sodium starch glycolate from 2% to 10% and increasing the dissolution speed from 50 rpm to 75 rpm had a synergistic effect on the overall dissolution performance of Cap-34.

Based on the dissolution findings the level of Aerosil R972 was reduced to 0.5% w/w for 0.1 mg starch-lactose based BIC formulations.

6.8 Evaluation of Different Acidifiers and their Levels for Mannitol and Starch-Lactose Based BIC Formulations Since Compound 1 degrades above pH 5, low pH environment of the drug product is desired. In order to achieve low micro-environmental pH environment of the drug product, an acidifier was incorporated in BIC formulation.

Three acidifiers namely: fumaric acid (pKa—3.0), maleic acid (pKa—1.91), and succinic acid (pKa—4.18) were evaluated to achieve low pH environment of the starch-lactose, and mannitol based BIC formulations. Of these acids, fumaric acid and maleic acid were evaluated further based on their lower pKa's, whereas, succinic acid was found to be less compatible with the drug substance.

The pH of the formulation blends with and without acidifiers was measured by slurry method. About 200 to 400 mg starch-lactose based BIC and mannitol based BIC blends were weighed and diluted with 0.5 mL distilled water. The dispersion was vortexed for 2 minutes to obtain homogeneous slurry to measure its pH.

Based on the evaluated data as shown in the following tables, starch-lactose based BIC formulation without any acidifier has a pH of 6.3. This high pH environment may prove to be detrimental for the drug product stability. To lower the pH, addition of fumaric acid and maleic acid at 2%, 3%, and 5% levels were evaluated for starch-lactose based BIC batches. Since minor adjustments in the levels of stronger acidifier (maleic acid) brought the pH down significantly which could also have a detrimental effect on stability of the formulation, fumaric acid was selected as the acidifier of choice. However, due to the slower dissolution of Starch-lactose based formulation, incorporation of disintegrants was essential. To optimize the pH of starch-lactose based BIC formulations containing fumaric acid in presence of different disintegrants, further pH assessments were carried out. The pH of mannitol based BIC formulation with 3% fumaric acid was found to be 2.2, which was in the desired pH range of 2-3.

TABLE 9

Evaluation of type and level of Acidifiers for optimizing Starch-lactose and Mannitol based BIC formulations

| Composition Type | Acidifier/Level | pH |
|---|---|---|
| Starch-Lactose | NA | 6.3 |
| Starch-Lactose | Fumaric Acid-2% | 2.3 |
| Starch-Lactose | Fumaric Acid-3% | 2.2 |
| Starch-Lactose | Fumaric Acid-5% | 2.1 |
| Starch-Lactose | Maleic Acid-2% | 1.7 |
| Starch-Lactose | Maleic Acid-3% | 1.4 |
| Starch-Lactose | Maleic Acid-5% | 1.2 |
| Mannitol | Fumaric Acid-3% | 2.2 |

TABLE 10

Evaluation of Fumaric Acid level for optimizing Starch-lactose based formulations with or without disintegrants

| Composition Type | Disintegrant/Level | Acidifier/Level | pH |
|---|---|---|---|
| Starch-Lactose | | Fumaric Acid-3% | 3.2 |
| Starch-Lactose | Crospovidone-2% | Fumaric Acid-3% | 3.4 |
| Starch-Lactose | SSG-2% | Fumaric Acid-3% | 3.9 |
| Starch-Lactose | Croscarmellose Na-2% | Fumaric Acid-3% | 4.4 |
| Starch-Lactose | SSG-2% | Fumaric Acid-4% | 2.8 |

TABLE 10-continued

Evaluation of Fumaric Acid level for optimizing Starch-
lactose based formulations with or without disintegrants

| Composition Type | Disintegrant/Level | Acidifier/Level | pH |
|---|---|---|---|
| Starch-Lactose | Croscarmellose Na-2% | Fumaric Acid-4% | 2.9 |
| Starch-Lactose | SSG-10% | Fumaric Acid-5% | 2.9 |

Based on these pH studies, fumaric acid level of %3 w/w was selected for mannitol based BIC formulations, whereas, for starch-lactose based BIC formulations containing 1000 w/w sodium starch glycolate, 400 fumaric acid level was selected to maintain the micro-environmental pH of the blend between 2-3.

6.9 Comparative Evaluations of Direct Blend (Low Shear) and High Shear Mixing Processes on BIC Formulations to Achieve Acceptable Content Uniformity Mannitol and starch-lactose based formulations were assessed for content uniformity by Low Shear and High shear mixing processes. Capsules were collected throughout the encapsulation run and content uniformity was assessed by stratified CU sampling. All the prototype formulations with their compositions and manufacturing processes are listed in the following table.

TABLE 11

Prototype Formulations with their Manufacturing Processes for Mannitol, and Starch-Lactose based 0.1 mg BIC to achieve Acceptable Content uniformity

| Manufacturing Process | High Shear Mixing with Co-Milling Process | | | | Dry Blending with Co-Milling | HSM with Co-Milling |
|---|---|---|---|---|---|---|
| Batch Number | Cap 13 | Cap 15 | Cap 16 | Cap 18 | Cap28 | Cap31 |
| Ingredients | % w/w | % w/w | % w/w | % w/w | % w/w | % w/w |
| Compound 1 | 0.13 | 0.13 | 0.13 | 0.133 | 0.13 | 0.13 |
| Silica Dimethyl Silylate (Aerosil R972) | 2.0 | 2.0 | 2.0 | 2.0 | 1.0 | 1.0 |
| Mannitol (Pearlitol 200 SD) | | | 91.87 | 77.87 | 91.87 | 91.87 |
| Partially pregelatinized Maize Starch (Starch 1500) | 30.0 | 24.0 | | | | |
| Anhydrous Lactose (Supertab 24 AN) | 61.87 | 53.87 | | | | |
| HPBCD, 97% | | 14.0 | | 14.0 | | |
| Fumaric Acid Pharmaceutical grade (Powder) | 3.0 | 3.0 | 3.0 | 3.0 | 5.0 | 5.0 |
| Stearic Acid (Hystrene 5016 Veg) | 3.0 | 3.0 | 3.0 | 3.0 | 2.0 | 2.0 |
| Total (% w/w) | 100.0 | 100.0 | 100.0 | 100.0 | 100.0 | 100.0 |
| Total Capsule Fill Weight (mg) | 75.0 | 75.0 | 75.0 | 75.0 | 75.0 | 75.0 |

Overall, starch-lactose based BIC batches were found to be superior in achieving potency distribution with High Shear Mixing process and co-milling, whereas, mannitol based batches were found to have relatively poor potency distributions when processed either with High Shear Mixing process and co-milling or direct blending process and co-milling respectively. This could be attributed to sticking of material to the processing equipment's and tamping pins during manufacturing. The preliminary Content uniformity studies indicated Cap-15 (Starch-Lactose) containing HPBCD manufactured by High Shear Mixing with Co-milling was found to have best potency distribution (Mean—99.1%, RSD—1.9%) with an acceptability value (AV) of 4.4. However, the chemical degradation profile in the presence of HPBCD showed an increase in the degradant levels.

The Content uniformity rank order for the assessed BIC formulations is as follows: Capsule-15>Capsule-13>Capsule-18>Capsule-28>Capsule-16>Capsule-31. The rank order was based on potency distribution (% RSD), mean assay (%), and increase in Acceptance Values (AV), as provided in the following table.

TABLE 12

Content uniformity Rank Order based on potency
distribution (% RSD), mean assay (%), and Acceptance Values (AV)

| Batch | Formulation | Manufacturing Process | Mean Assay (%) | % RSD | Acceptance Value (AV) |
|---|---|---|---|---|---|
| Capsule-15 | Starch-lactose | High Shear Mixing with Co-Milling | 99.1 | 1.9 | 4.4 |
| Capsule-13 | Starch-lactose | High Shear Mixing with Co-Milling | 97.4 | 1.7 | 5.1 |
| Capsule-18 | Mannitol | High Shear Mixing with Co-Milling | 97.6 | 3.9 | 8.2 |
| Capsule-28 | Mannitol | Dry Blending with Co-Milling | 94.4 | 2.4 | 9.8 |
| Capsule-16 | Mannitol | High Shear Mixing with Co-Milling | 86.0 | 1.8 | 17 |
| Capsule-31 | Mannitol | High Shear Mixing with Co-Milling | 88.3 | 9.6 | 33.3 |

The relatively poor assay recovery for mannitol based formulations could be attributed to the high shear mixing resulting in adhesion of the blend to the processing surfaces. Therefore, the direct blending process (Low Shear) was selected as the method of choice for further development.

6.10 Starch-Lactose BIC Vs. Mannitol BIC—Accelerated Stability Assessment

Accelerated stability evaluations were performed on starch-lactose based BIC and mannitol based BIC formulations at the following storage conditions: 50° C./50% RH for T=3 days, 60° C./30% RH for T=3 days, 70° C./0% RH for T=3 days, and 70° C./50% RH for T=3 days. The data was compared with samples stored at 5° C. (control).

From the accelerated stability studies (FIG. 9), inclusion of HPBCD (Cap-15) for starch-lactose based formulations has helped retain the chiral purity when compared to formulations without the stabilizer (Cap-13). For Mannitol based formulations too, HPBCD (Cap-18) has helped maintain the chiral purity when compared to formulations without HPBCD (Cap-28 and Cap-31). High levels of fumaric Acid (5% w/w) for Cap-28 & Cap-31 also had negative impact on chiral purity when compared with (3% w/w) fumaric acid for Cap-16 mannitol based formulations. Overall, loss of chiral purity for Starch-lactose based formulations without HPBCD (Cap-13) was found to be lower than mannitol based formulations without HPBCD (Cap-16).

Incorporation of stronger acid (maleic acid) was also evaluated to assess its effect on stability profile of BIC formulations as shown in the following table.

TABLE 13

Comparative Accelerated stability evaluation of mannitol based BIC with Fumaric Acid and Maleic Acid

| Manufacturing Process | Direct Blending with Co-Milling | HSM with Co-Milling | HSM with Co-Milling |
|---|---|---|---|
| Batch Number | Cap28 | Cap31 | Cap32 |
| Ingredients | % w/w | % w/w | % w/w |
| Compound 1 | 0.13 | 0.13 | 0.13 |
| Silica Dimethyl Silylate (Aerosil R972) | 1.0 | 1.0 | 1.0 |
| Mannitol (Pearlitol 200 SD) | 91.87 | 91.87 | 91.87 |
| Maleic Acid Pharmaceutical grade | | | 5.0 |
| Fumaric Acid Pharmaceutical grade (Powder) | 5.0 | 5.0 | |
| Stearic Acid (Hystrene 5016 Veg) | 2.0 | 2.0 | 2.0 |
| Total (% w/w) | 100.0 | 100.0 | 100.0 |
| Total Capsule Fill Weight (mg) | 75.0 | 75.0 | 75.0 |

FIG. 10 shows inclusion of maleic acid in the formulation (Cap-32) resulted in better chiral stability, but resulted in an increase in chemical degradants as shown in FIG. 11 when compared to formulations containing fumaric acid (Cap-28 & Cap-31). In summary, fumaric acid was selected as acidifier of choice at 3% w/w levels for mannitol based BIC formulations, and 4% w/w levels for starch-lactose based BIC formulations with 10% sodium starch glycolate as a disintegrant.

In order to assess the effect on drug product stability by incorporation of disintegrant (crospovidone, SSG or croscarmellose sodium) for starch-lactose based BIC formulations comparative accelerated stability screening studies were carried out on 0.1 mg starch-lactose BIC formulations with (Cap-24, Cap-25, Cap-26) and without disintegrant (Cap-13) versus 0.1 mg mannitol based BIC formulation (Cap-16).

From FIG. 12, Cap-25 containing starch-lactose based BIC with SSG is found to be less prone to oxidation (oxidation degradant 1, RRT 0.66) except at very high temperature and humidity (70° C./50% RH). Formulation containing crospovidone (Cap-24) undergoes significant oxidation at higher temperature. The stability of profile of starch-lactose BIC without any disintegrant (Cap-13) is found to be most stable. Mannitol based formulation (Cap-16) undergoes oxidation primarily at elevated temperature and low humidity conditions (60° C./30% RH and 70° C.).

Similarly, Cap-26 containing croscarmellose sodium is found to be prone to oxidation (oxidation degradant 2), however, the level is consistent at all storage conditions (FIG. 13). Cap-24 containing crospovidone is found to have similar stability profile as that of Cap-25 containing SSG, however, Cap-25 is superior due to its better tolerability for oxidative degradant 1. Overall, formulations containing starch-lactose without disintegrants (Cap-13) exhibit better tolerability towards oxidative degradants versus formulations with disintegrants (Cap-24, Cap-25, & Cap-26) or with those based on mannitol (Cap-16).

Incorporation of disintegrants have helped reduce hydrolytic impurity (FIG. 14 and FIG. 15) and from the assessed disintegrants, Cap-25 containing SSG was found to be most stable.

From FIG. 16 it can be seen that incorporation of disintegrants into the formulation have helped retain chiral purity. Of the evaluated disintegrants, Cap-24 containing crospovidone and Cap-25 containing SSG were found to have better stability.

The shelf-life prediction for mannitol based BIC formulation was assessed by Accelerated Stability Assessment Program (ASAP) for chiral purity and degradants. Based on the ASAP study for 0.1 mg mannitol based BIC formulation (Cap-16), the predicted shelf-life of 0.1 mg mannitol BIC based formulation on loss of chiral purity (Spec—3%) is 3+ years at room temperature storage without desiccant.

Based on the predictive ASAP modeling for 0.1 mg mannitol based BIC formulation (Cap-16), the predicted shelf-life of 0.1 mg mannitol BIC is 3+ years at room temperature storage without desiccant for oxidation degradant.

Based on the predictive ASAP modeling for 0.1 mg mannitol based BIC formulations, the shelf-life of 0.1 mg mannitol BIC at room temperature storage without desiccant is predicted to be 1.5+ years for primary hydrolysis degradant.

Based on the predictive ASAP modeling for mannitol based BIC formulations, the shelf-life of 0.1 mg mannitol BIC at room temperature storage without desiccant is predicted to be 3+ years for secondary hydrolysis degradant.

Since hydrolysis was found to be major shelf-life limiting, addition of 0.5 g silica to the HDPE bottles predicted to retard hydrolysis and enhance the shelf-life from earlier predicted shelf-life of 1.5+ years to 2.9+ years respectively.

In summary, from the preliminary ASAP study the predicted shelf-life at room temperature storage for mannitol based BIC formulation without silica gel is about 1.5+ years, whereas, with 0.5 g silica gel at RT is about 2.9+ years.

Similarly, shelf-life prediction for starch-lactose based BIC formulation was also assessed by Accelerated Stability Assessment Program (ASAP) for chiral purity and related impurities. Based on the ASAP study for 0.1 mg starch-lactose based BIC formulation (Cap-34), the predicted shelf-life of 0.1 mg starch-lactose based BIC formulation on loss of chiral purity is 3+ years at room temperature storage without silica gel desiccant.

Based on the predictive ASAP modeling for 0.1 mg starch-lactose BIC formulations, the shelf-life of 0.1 mg starch-lactose BIC at room temperature storage without desiccant is predicted to be 2.5+ years for primary hydrolysis degradant.

Likewise, based on the predictive ASAP modeling for 0.1 mg starch-lactose BIC formulations, the shelf-life of 0.1 mg starch-lactose BIC at room temperature storage without desiccant is predicted to be 3+ years for secondary hydrolysis degradant.

Based on the predictive ASAP modeling for starch-lactose based BIC formulation (Cap-34), the predicted shelf-life of 0.1 mg starch-lactose BIC is 3+ years at room temperature storage without desiccant for oxidation degradant.

In summary the shelf-life limiting degradation pathway for 0.1 mg starch-lactose based BIC formulation (Cap-34) could be hydrolysis without silica gel desiccant. The predicted shelf-life is 2.5+ years at room temperature storage.

Overall, the predicted shelf-life for the both the formulations is 1.5-2+ years at room temperature storage and shelf-life limiting pathway is hydrolysis.

6.11 Assessment of Hydrophobic and Hydrophilic Silica on the 0.1 mg Formulations Agglomeration and surface adhesion of cohesive APIs present challenges for solid dosage formulation development, especially for low strength formulations. The morphology of Compound 1 crystals is hydrophobic agglomerated clusters, which was wet milled at the seeding stage. Compound 1 has sticking tendency, and poor flow and adhesion onto the surface during processing were observed.

Scanning electron microscope (SEM) images of Compound 1 crystal not coated and coated with Aerosil R-972 are shown in FIG. 17A and FIG. 17B, respectively. The images show that pre-dispersion of the Compound 1 crystals with hydrophobic silica Aerosil R-972 (coating Compound 1 with Aerosil R-972) overcame the agglomeration and adhesion issue.

The effectiveness in dealing with the agglomeration and cohesiveness by hydrophobic silica is manifested in comparison of hydrophilic silicas (Aerosil 200 and Aerosil 300), as shown in the SEMs images in FIG. 18A to FIG. 18D.

The stickiness of Compound 1 to the process containers was further alleviated with pretreatment of the containers with lubricant mixture.

6.12 Assessment of Alternate Silica Grades on the Dissolution Release Profile of 2 mg BIC Formulations Due to constraints on global regulatory acceptability of silica dimethyl silylate (Aerosil R972) along with low maximum allowable limit (0.5 mg w/w per Unit for IR Capsules) per USFDA's inactive ingredients database (IIG), alternate grades of silica for higher dose strengths (0.5 mg and 2 mg BIC) were evaluated. The drug-excipient compatibility results from FIG. 19 show that Aerosil R972 due to its hydrophobicity was found to be preventing the drug degradation when compared with either Aerosil 200 Pharma or Aerosil 300 Pharma. The rank order of stability was follows: Aerosil R972>Aerosil 200>Aerosil 300.

Aerosil 200 was not only found to be relatively more compatible than Aerosil 300, but also offers less surface area 200 $m^2/g$ when compared to 300 $m^2/g$ offered by Aerosil 300, the overall silica-drug substance interaction can be minimized thus reducing the degradation products and preventing loss of chiral purity. The stability of low capsule strength (0.1 mg) was very challenging and acceptable stability could be achieved by coating the API with hydrophobic silica (Aerosil R972) hence for 0.1 mg strength the Aerosil R 972 was selected as glidant/de-agglomerating/stabilizing agent. For higher strengths (0.5 and 2 mg) since stability challenge was less stringent the use of hydrophilic silica (Aerosil 200) was evaluated.

In order to assess the effect of replacing Aerosil R972 with Aerosil 200 Pharma on the drug product properties, dissolution studies were performed. Since starch-lactose based batches were found to have slower dissolution profiles than mannitol based batches, prototype starch-lactose 2 mg BIC batches containing 0.5%, 1% and 2% Aerosil 200 as provided in the following table were assessed.

TABLE 14

Comparative evaluation of varying levels of Aerosil 200 Pharma on Dissolution release profile of 2 mg Starch-Lactose BIC.

| Manufacturing Process<br>Batch Number<br>Ingredients | Dry Blend with Manual Filling<br>Cap38<br>% w/w | Dry Blend with Manual Filling<br>Cap39<br>% w/w | Dry Blend with Manual Filling<br>Cap40<br>% w/w |
|---|---|---|---|
| Compound 1 | 1.0 | 1.0 | 1.0 |
| Colloidal Silicon dioxide (Aerosil 200 Pharma) | 2.0 | 1.0 | 0.5 |
| Partially pregelatinized Maize Starch (Starch 1500) | 20.0 | 20.0 | 20.0 |
| Anhydrous Lactose (Supertab 24 AN) | 59.0 | 60.0 | 60.5 |
| Fumaric Acid Pharmaceutical grade (Powder) | 4.0 | 4.0 | 4.0 |
| Stearic Acid (Hystrene 5016 Veg) | 4.0 | 4.0 | 4.0 |
| Total (% w/w) | 100.0 | 100.0 | 100.0 |
| Total Capsule Fill Weight (mg) | 200 | 200 | 200 |

As shown in FIG. 20, the in vitro dissolution studies indicate no effect on the dissolution release profiles with varying the levels of Aerosil 200 from 0.5% w/w, 1% w/w, and 2% w/w, however, the release rates at 75 rpm were faster when compared to the release rates at 50 rpm paddle speed.

6.13 Manufacturing of Mannitol and Starch-Lactose 0.1, 0.5, & 2 mg BIC Batches The theoretical unit formulae for mannitol and starch-lactose 0.1, 0.5, and 2 mg BIC batches are provided in the following table.

TABLE 15

Theoretical Unit formulae of 0.1 mg, 0.5 mg, and 2 mg Mannitol and Starch-Lactose based BIC formulations

| | Direct Blending with Co-milling | | | | | |
|---|---|---|---|---|---|---|
| Manufacturing Process | 0.1 mg BIC | | 0.5 mg BIC | | 2 mg BIC | |
| Batch Number<br>Ingredients | Cap-37<br>% w/w | Cap-41<br>% w/w | Cap-42<br>% w/w | Cap-43<br>% w/w | Cap-45<br>% w/w | Cap-46<br>% w/w |
| Compound 1 | 0.133 | 0.13 | 0.50 | 0.50 | 1.00 | 1.00 |
| Silica Dimethyl Silylate (Aerosil R972) | 0.50 | 0.50 | | | | |
| Colloidal Silicon dioxide (Aerosil 200 Pharma) | | | 1.00 | 1.00 | 2.00 | 1.00 |
| Mannitol (Pearlitol 200 SD) | 92.37 | | 91.5 | | 90.00 | |
| Partially pregelatinized Maize Starch (Starch 1500) | | 20.00 | | 19.50 | | 19.00 |

TABLE 15-continued

Theoretical Unit formulae of 0.1 mg, 0.5 mg, and 2 mg Mannitol and Starch-Lactose based BIC formulations

| | Direct Blending with Co-milling | | | | | |
|---|---|---|---|---|---|---|
| Manufacturing Process | 0.1 mg BIC | | 0.5 mg BIC | | 2 mg BIC | |
| Batch Number | Cap-37 | Cap-41 | Cap-42 | Cap-43 | Cap-45 | Cap-46 |
| Ingredients | % w/w | % w/w | % w/w | % w/w | % w/w | % w/w |
| Anhydrous Lactose (Supertab 24 AN) | | 61.37 | | 61.00 | | 61.00 |
| Sodium Starch Glycolate (Explotab) | | 10.0 | | 10.0 | | 10.0 |
| Fumaric Acid Pharmaceutical grade (Powder) | 3.00 | 4.00 | 3.00 | 4.00 | 3.00 | 4.00 |
| Stearic Acid (Hystrene 5016 Veg) | 4.00 | 4.00 | 4.00 | 4.00 | 4.00 | 4.00 |
| Total (% w/w) | 100.0 | 100.0 | 100.0 | 100.0 | 100.0 | 100.0 |
| Total Capsule Fill weight (mg) | 75.0 | 75.0 | 100.0 | 100.0 | 200.0 | 200.0 |
| HPMC Vcaps Plus Capsule Shell | Size 4 Opaque White V Cap Plus | | Size 3 Yellow Ivory Opaque V Cap Plus | | Size 2 Swedish Orange V Cap Plus | |

(a) Manufacturing Process for Mannitol Based 0.1 mg BIC

In one example, 0.1 mg mannitol based BIC was prepared according to the development process described below.

Preparation of Pre-treatment Mixture: Compound 1 has sticking tendency hence to minimize sticking to the equipment surfaces a pre-treatment mixture was prepared by mixing a portion of mannitol and stearic acid in turbula blender. All the equipment used in the manufacture were pre-treated using pre-treatment mixture.

Blending 1: Weighed amount of Compound 1 and Aerosil R972 were added to pre-treated turbula blender and blended for 170 revolutions.

Blending 2: Weighed fumaric acid was added to turbula blender and blended for 170 revolutions.

Blending 3: Mannitol and blend 2 were loaded into the surface treated 4 L turbula blender and blended for 340 revolutions.

Delumping 1: Blend 3 was passed through surface pre-treated Co-mil fitted with 457 m round screen at 1600 rpm. Co-mil was rinsed with a portion of pre-treatment mixture.

Blending 4: Portion of pre-treatment mixture, co-milled blend, and portion of mannitol were added to V-blender and the powder was blended for 300 revolutions.

Delumping 2: Blend 4 and remaining pre-treatment mixture were passed through co-mil fitted with 457 m round screen at 1600 rpm. Remaining mannitol was passed through co-mil to rinse the co-mil.

Sifting: The rest of the stearic acid was hand screened through Sieve #25.

Blending 5 (Lubrication): The blend from delumping 2 and sifted stearic acid were loaded into a V-blender and blended for 300 revolutions. The final lubricated blend was discharged into one of the two tared surface treated collection bags (1 or 2).

Encapsulation: The final blend was loaded in the hopper of Bosch encapsulator. The 75 mg blend was filled in size #4 HPMC Vcap plus capsule using size #4 disc at 75_85 capsules per minute speed. Average weight and weight variation were checked during encapsulation every 15 minutes and capsules were collected for stratified CU testing.

(b) Manufacturing Processes for 0.5 mg and 2 mg Mannitol BIC

In one example, 0.5 and 2 mg mannitol based BIC were prepared according to the development process described below.

Preparation of Pre-treatment Mixture: Compound 1 has sticking tendency hence to minimize sticking to the equipment surfaces a pre-treatment mixture was prepared by mixing a portion of mannitol and stearic acid in turbula blender. All the equipment used in the manufacture were pre-treated using pre-treatment mixture.

Blending 1: Weighed amount of Compound 1, a portion of mannitol, and fumaric acid were added to pre-treated turbula blender and blended for 340 revolutions.

Delumping 1: Blend 1 and a portion of mannitol were passed through surface pre-treated Co-mil fitted with 457 m round screen at 1600 rpm. Co-mil was rinsed with a portion of pre-treatment mixture.

Blending 2: Portion of pre-treatment mixture, the blend from delumping 1, and a portion of mannitol were added to V-blender and the powder was blended for 300 revolutions.

Delumping 2: Blend 2 and a portion of mannitol were passed through co-mil fitted with 457 m round screen at 1600 rpm. Remaining mannitol was passed through co-mil to rinse the co-mil.

Sifting: Colloidal silicon dioxide (Aerosil 200) and stearic acid were hand screened through Sieve #25.

Blending 3 (Lubrication): The blend from delumping 2 and sifted colloidal silicon dioxide stearic acid were loaded into a V-blender and blended for 300 revolutions. The final lubricated blend was discharged into one of the two tared surface treated collection bags (1 or 2).

Encapsulation: The final blend was loaded in the hopper of Bosch encapsulator. For 0.5 mg BIC, 100 mg blend was filled in size #3 HPMC Vcap plus capsule using size #3 disc at 75-85 capsules per minute speed. For 2 mg BIC, 200 mg blend was filled in size #2 HPMC Vcap plus capsule using size #2 disc at 75-85 capsules per minute speed. Average weight and weight variation were checked during encapsulation every 15 minutes and capsules were collected for stratified CU testing.

(c) Manufacturing Process for Starch-Lactose Based 0.1 mg BIC

In one example, 0.1 mg starch-lactose based BIC was prepared according to the development process described below.

Preparation of Pre-treatment Mixture: Compound 1 has sticking tendency hence to minimize sticking to the equipment surfaces a pre-treatment mixture was prepared by mixing a portion of anhydrous lactose and stearic acid in turbula blender. All the equipment used in the manufacture were pre-treated using pre-treatment mixture.

Blending 1: Weighed amount of Compound 1 and Aerosil R972 were added to pre-treated turbula blender and blended for 170 revolutions.

Blending 2: Weighed fumaric acid was added to turbula blender and blended for 170 revolutions.

Blending 3: A portion of anhydrous lactose, blend 2, and a portion of partially pregelatinized maize starch were loaded into the surface treated 4 L turbula blender and blended for 340 revolutions.

Delumping 1: Blend 3 was passed through surface pre-treated Co-mil fitted with 457 m round screen at 1600 rpm. Co-mil was rinsed with a portion of pre-treatment mixture.

Blending 4: Portion of anhydrous lactose, co-milled blend, portion of pregelatinized maize starch, and sodium starch glycolate were added to V-blender and the powder was blended for 300 revolutions.

Delumping 2: Blend 4 and remaining pre-treatment mixture were passed through co-mil fitted with 457 m round screen at 1600 rpm.

Sifting: The rest of the stearic acid was hand screened through Sieve #25.

Blending 5 (Lubrication): The blend from delumping 2 and sifted stearic acid were loaded into a V-blender and blended for 300 revolutions. The final lubricated blend was discharged into one of the two tared surface treated collection bags (1 or 2).

Encapsulation: The final blend was loaded in the hopper of Bosch encapsulator. The 75 mg blend was filled in size #4 HPMC Vcap plus capsule using size #4 disc at 75-85 capsules per minute speed. Average weight and weight variation were checked during encapsulation every 15 minutes and capsules were collected for stratified CU testing.

(d) Manufacturing Process for Starch-Lactose Based 0.5 and 2 mg BIC

In one example, 0.5 and 2 mg starch-lactose based BIC were prepared according to the development process described below.

Preparation of Pre-treatment Mixture: Compound 1 has sticking tendency hence to minimize sticking to the equipment surfaces a pre-treatment mixture was prepared by mixing a portion of anhydrous lactose and stearic acid in turbula blender. All the equipment used in the manufacture were pre-treated using pre-treatment mixture.

Blending 1: Weighed amount of Compound 1, a portion of anhydrous lactose, a portion of pregelatinized maize starch, and fumaric acid were added to pre-treated turbula blender and blended for 340 revolutions.

Delumping 1: Blend 1 and a portion of pregelatinized maize starch were passed through surface pre-treated Co-mil fitted with 457 m round screen at 1600 rpm. Co-mil was rinsed with a portion of pre-treatment mixture.

Blending 2: Portion of pre-treatment mixture, the blend from delumping 1, and a portion of anhydrous lactose were added to V-blender and the powder was blended for 300 revolutions.

Delumping 2: Blend 2 was passed through co-mil fitted with 457 m round screen at 1600 rpm. Sodium starch glycolate was passed through co-mil to rinse the co-mil.

Sifting: Colloidal silicon dioxide (Aerosil 200) and stearic acid were hand screened through Sieve #25.

Blending 3 (Lubrication): The blend from delumping 2 and sifted colloidal silicon dioxide stearic acid were loaded into a V-blender and blended for 300 revolutions. The final lubricated blend was discharged into one of the two tared surface treated collection bags (1 or 2).

Encapsulation: The final blend was loaded in the hopper of Bosch encapsulator. For 0.5 mg BIC, 100 mg blend was filled in size #3 HPMC Vcap plus capsule using size #3 disc at 75-85 capsules per minute speed. For 2 mg BIC, 200 mg blend was filled in size #2 HPMC Vcap plus capsule using size #2 disc at 75-85 capsules per minute speed. Average weight and weight variation were checked during encapsulation every 15 minutes and capsules were collected for stratified CU testing.

6.14 Characterization of Mannitol and Starch-Lactose 0.1, 0.5, & 2 mg BIC Batches (a) Flowability Assessment To assess the flowability of the powder blend, Dietmar-Schulze Ring Shear Tester (RST) was used. The samples were prepared using Shear Cell #1 and standard loads of 400 Pa to 3600 Pa were applied. The flow function co-efficient (ffc) values were determined from the obtained Major Consolidation Stress, ($\sigma 1$) Pa and its corresponding Unconfined Yield Strength, ($f_c$) Pa using the following equation:

$$ffc = \sigma 1 / fc$$

Flow behavior of a powder can be categorized numerically based on the obtained ffc value: ffc<1 (Not Flowing); 1<ffc<2 (Very Cohesive); 2<ffc<4 (Cohesive); 4<ffc<10 (Easy Flowing); ffc>10 (Free Flowing).

The flowability rank order for the analyzed BIC blends are as follows: Cap-37>Cap-41>Cap-42>Cap-43>Cap-45>Cap-46>Cap-44. From the flowability plots shown in FIG. 21, 0.1 mg mannitol (Cap 37) and starch-lactose BIC (Cap 41) batches were found to have best overall flowability and can be attributed to low drug loading in the presence of 0.5% Aerosil R972. The 0.5 mg mannitol BIC (Cap 42) and starch-lactose BIC (Cap 43) batches also exhibited good flowability profiles. 2 mg Mannitol BIC (Cap 45) containing 2% Aerosil 200 was found to have acceptable flowability (borderline "Free Flowing"). 2 mg Starch-lactose BIC with 2% Aerosil 200 (Cap44) blend was found to be "Easy Flowing".

It can be noted that the flow propensity is reducing with an increase in the levels of Aerosil 200-1% for 0.5 mg BIC batches, 2% for mannitol BIC batch and starch-lactose BIC batch. The flowability for 2 mg starch-lactose BIC (Cap44) blend had impact during the encapsulation process where high weight variability was encountered. This high weight variability resulted in wider potency distribution as shown in FIG. 22. To overcome this the levels of Aerosil 200 were reduced to 1% from the earlier 2% levels (Cap44), the flow behavior for 2 mg starch-lactose (Cap46) BIC blend with 1% Aerosil 200 was found to be "Freely Flowing" with tighter potency distribution.

(b) Water Activity Testing

Water activity is a measure of how tightly bound the water is within a substance. To measure water activity, a sample is placed in a sealed vessel which is allowed to reach equilibrium. The final relative humidity (RH) in the vessel is reported as a fraction called "Aw". Pure water has an Aw of 1.00. Since Form K of Compound 1 is a channel hydrate which converts to an anhydrous form at RH<20%, the water activity was tested to assess the chance of form conversion. HygroLab 3 Bench Top Indicator was used to determine water activity testing. Before testing the samples, the equipment is calibrated at different relative humidity levels using RH standards (0% RH, 35% RH, and 80% RH) and at different temperatures to ensure accuracy of the probes. A known amount of sample is sealed inside the sample cell by twisting the cap in downward direction. The starting temperature is recorded before beginning the test. When the change in temperature before and after the test is not more than 0.5° C. record $A_w$.

Both filled capsules and final blend show water activity above $A_w$=0.300 for all formulations. Therefore, at standard room RH of 35-40%, it is unlikely that Compound 1 will convert to the anhydrous form.

(c) Dissolution Profiles

For 0.1 mg BIC batches, mannitol based BIC exhibited ~95% drug release in 30 minutes' when compared to ~80% drug release for starch-lactose based batch as shown in FIG. 23. The relative slower drug release for starch-lactose based BIC batches is attributed to the formation of plug retarding the drug release. The drug release profile is slower, but acceptable for starch-lactose based formulation. Overall, close to 100% release is achieved for both formulation by 60 min.

At 0.5 mg strength, both formulations have similar dissolution release profiles as shown in FIG. 24. Overall, close to 100% release is achieved for both formulation by 60 min.

The dissolution release profile in FIG. 25 for 2 mg strength shows that about 90% drug release was observed for mannitol based BIC in 30 minutes, versus ~75% drug release for starch-lactose based BIC formulation. However, by 60 minutes both BIC formulations exhibited 100% drug release and demonstrate acceptable dissolution release profiles.

(d) Stability Profiles

The stability of mannitol BIC capsules in HDPE bottle without desiccant was evaluated at 25° C./60% RH and 40° C./75% RH at 1-month time point as shown in FIG. 26. 0.1 mg BIC was found to be very stable at all studied conditions. Higher dose strengths (0.5 mg and 2 mg) BIC were found to be susceptible to hydrolytic degradant at 40° C./75% RH for 1M. The difference between these strengths is the grade and levels of Silica. For 0.1 mg BIC (Cap-37), Aerosil R972 (hydrophobic silica) coats the API surface well and prevents degradation of API, whereas, hydrophilic silica (Aerosil 200) was employed for 0.5 mg and 2 mg BIC, respectively. The increase in hydrolytic degradant correlates with an increase in levels of hydrophilic Aerosil 200.

The increase in R-Isomer levels for 0.5 mg BIC and 2 mg BIC follows a trend similar to that of increase in the levels of hydrolytic degradant indicating the effect of Aerosil 200 on loss of chiral purity as shown in FIG. 27.

(e) Dissolution Stability

The stability dissolution release profiles for 0.1 mg mannitol based BIC batches at all conditions were found to be reproducible, whereas, the dissolution release profiles of 0.1 mg starch-lactose based BIC batches at 40° C./75% RH at 1M and 25° C./60% RH were found to be slower than at T=0 (initial) as shown in FIG. 28.

From FIG. 29, the dissolution release profiles for 0.5 mg BIC for both mannitol, and starch-lactose were found to be reproducible. A little slowdown was observed in the dissolution release profile for 0.5 mg starch-lactose based BIC at 40° C./75% RH at T=1M at initial time points, but eventually, complete drug release was observed. Overall, both formulations were found to exhibit reproducible dissolution profiles indicating dissolution stability.

Likewise, the dissolution release profiles for 2 mg BIC formulations for both mannitol and starch-lactose based formulations were also found to be reproducible at all tested conditions (FIG. 30).

(f) Particle Size Distribution for Mannitol Based Batches

Particle size distribution using sifting method was performed using Rotap sifter by stacking 6 sieves in the order of decreasing screen opening from top to bottom (coarser on top followed by finer on bottom). A pan was placed at the bottom to collect the fines. The experiment was performed in duplicate using 425 μm screen, 250 μm screen, 180 μm screen, 125 μm screen, 90 μm screen, and 75 μm screen. The D10, D50 and D90 of all the lubricated blends for 0.1 mg, 0.5 mg, and 2 mg mannitol based batches were determined and their values are provided in the following table.

TABLE 16

Particle size distribution of the lubricated blends for 0.1 mg, 0.5 mg, and 2 mg mannitol based batches

| Particle size distribution | 0.1 mg batch (μm) | 0.5 mg batch (μm) | 2 mg batch (μm) |
|---|---|---|---|
| D10 | ~87.5 | ~75 | ~75 |
| D50 | ~137.5 | ~131.25 | ~143.75 |
| D90 | ~193.75 | ~181.25 | ~206.25 |

(g) Comparative Evaluation of Content Uniformity (CU) Between Mannitol BIC and Starch-Lactose BIC Formulations The potency distribution, mean assay recovery and mean CU for mannitol based BIC (Cap-37, Cap-42, and Cap-45) and starch based BIC (Cap-41, Cap-43, and Cap-46) are shown in the following table.

TABLE 17

Summary of Content Uniformity (CU) for 0.1 mg, 0.5 mg, and 2 mg Mannitol and Starch-Lactose BIC formulations

| Batch Number | 0.1 mg Mannitol BIC Cap-37 | 0.1 mg Starch-lactose BIC Cap-41 | 0.5 mg Mannitol BIC Cap-42 | 0.5 mg Starch-lactose BIC Cap-43 | 2 mg Mannitol BIC Cap-45 | 2 mg Starch-lactose BIC Cap-46 |
|---|---|---|---|---|---|---|
| CU Average | 96.13 | 94.16 | 97.0 | 99.9 | 98.89 | 100.61 |
| % RSD | 2.7 | 1.32 | 1.3 | 1.28 | 0.69 | 2.0 |
| Acceptance Value (AV) | 8.6 | 7.5 | 4.6 | 3.0 | 1.67 | 4.86 |
| Mean Assay | 99.7 | 96.1 | 97.7 | 99.4 | 99.0 | 100.5 |
| Avg Cap Weight (mg) | 113.1 | 113.3 | 147.6 | 147.8 | 262.4 | 262.8 |
| Target Cap Weight (mg) | 111.8 | | 146.9 | | 260.6 | |

Due to adhesive nature of blend for mannitol based BIC formulations, variations in the potency distribution had been observed between different formulations manufactured either by Low shear or High shear processes. However, pre-treatment of surfaces prior to batch manufacturing has yielded acceptable data with narrow potency distributions as shown in the table.

From the table, not only the % RSD was tighter for starch-lactose based BIC, but the acceptance values were also lower. Likewise, for 0.5 mg BIC batches the mean assay recovery, mean CU, and AV values for starch-lactose based BIC (Cap-43) were found to be superior to mannitol based BIC (Cap-42), whereas, the % RSD was found to be similar for both the batches. Finally, the mean assay recovery and mean CU were found to be higher for starch-lactose based BIC (Cap-46), however, the % RSD and AV were found to be better for mannitol based BIC (Cap-45). It has also been demonstrated that the mean assay recoveries were getting better with an increase in dose strength, whereas, acceptance values were getting lower with an increase dose strength indicating vulnerability to CU for low dose strengths.

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method of treating multiple myeloma comprising administering a therapeutically effective amount of a pharmaceutical composition to a patient having multiple myeloma, wherein the pharmaceutical composition comprises 1) Compound 1:

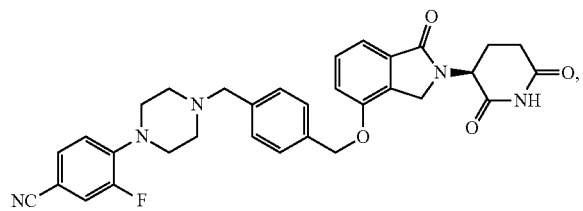

1 or an enantiomer, mixture of enantiomers, tautomer, isotopolog, or pharmaceutically acceptable salt thereof, at an amount of from about 0.05 to about 3% w/w; 2) mannitol at an amount of from about 80 to about 98% w/w; 3) a glidant at an amount of from about 0 to about 10% w/w; 4) an acidifier at an amount of from about 0 to about 6% w/w; and 5) a lubricant at an amount of from about 0 to about 8% w/w.

2. The method of claim 1, wherein Compound 1, or an enantiomer, mixture of enantiomers, tautomer, isotopolog, or pharmaceutically acceptable salt thereof, is free base of Compound 1.

3. The method of claim 2, wherein the free base of Compound 1 is a crystalline free base of Compound 1.

4. The method of claim 2, wherein the crystalline free base of Compound 1 is characterized by an XRPD pattern comprising peaks at approximately 14.6, 18.2, and 18.3° 2θ.

5. The method of claim 1, wherein the amount of Compound 1, or an enantiomer, mixture of enantiomers, tautomer, isotopolog, or pharmaceutically acceptable salt thereof, is from about 0.1 to about 1.5% w/w.

6. The method of claim 1, wherein the amount of mannitol is from about 85 to about 95% w/w.

7. The method of claim 1, wherein the glidant is silica dimethyl silylate or colloidal silicon dioxide.

8. The method of claim 1, wherein the amount of the glidant is from about 0.25 to about 3% w/w.

9. The method of claim 1, wherein the acidifier is fumaric acid.

10. The method of claim 1, wherein the amount of the acidifier is from about 2 to about 5% w/w.

11. The method of claim 1, wherein the lubricant is stearic acid.

12. The method of claim 1, wherein the amount of the lubricant is from about 2 to about 6% w/w.

13. The method of claim 1, wherein the pharmaceutical composition comprises: 1) Compound 1 at an amount of about 0.13% w/w; 2) mannitol at an amount of about 92.37% w/w; 3) silica dimethyl silylate at an amount of about 0.5% w/w; 4) fumaric acid at an amount of about 3% w/w; and 5) stearic acid at an amount of about 4% w/w.

14. The method of claim 1, wherein the pharmaceutical composition comprises: 1) Compound 1 at an amount of about 0.5% w/w; 2) mannitol at an amount of about 91.5% w/w; 3) colloidal silicon dioxide at an amount of about 1% w/w; 4) fumaric acid at an amount of about 3% w/w; and 5) stearic acid at an amount of about 4% w/w.

15. The method of claim 1, wherein the pharmaceutical composition comprises: 1) Compound 1 at an amount of about 1% w/w; 2) mannitol at an amount of about 90% w/w; 3) colloidal silicon dioxide at an amount of about 2% w/w; 4) fumaric acid at an amount of about 3% w/w; and 5) stearic acid at an amount of about 4% w/w.

16. The method of claim 1, wherein the multiple myeloma is newly diagnosed multiple myeloma.

17. The method of claim 1, wherein the multiple myeloma is relapsed or refractory multiple myeloma.

18. The method of claim 17, wherein the multiple myeloma is relapsed or refractory to one, two, or three previous treatments.

19. The method of claim 1, wherein the method comprises administering the pharmaceutical composition in combination with one or more second active agents.

20. The method of claim 19, wherein the one or more second active agents are one or more of dexamethasone, daratumumab, a proteasome inhibitor, a histone deacetylase inhibitors, a chemotherapy agent, a BCL-2 inhibitor, an MCL-1 inhibitor, a BET inhibitor, or an LSD-1 inhibitor, or a combination thereof.

21. The method of claim 20, wherein the proteasome inhibitor is bortezomib or carfilzomib.

22. The method of claim 19, wherein the one or more second active agents are one or more of ACY241, AMG176, birabresib, 4-[2-(cyclopropylmethoxy)-5-(methanesulfonyl)phenyl]-2-methylisoquinolin-1(2H)-one, 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile, cyclophosphamide, dexamethasone, doxorubicin, etoposide, GSK525762A, MIK665, panobinostat, venetoclax, or vincristine.

23. The method of claim 19, wherein the one or more second active agents include dexamethasone.

* * * * *